US012626778B2

(12) United States Patent
Noto et al.

(10) Patent No.: US 12,626,778 B2
(45) Date of Patent: May 12, 2026

(54) ACCELERATED HIDDEN MARKOV MODELS FOR GENOTYPE ANALYSIS

(71) Applicant: Ancestry.com DNA, LLC, Lehi, UT (US)

(72) Inventors: Keith Daniel Noto, San Francisco, CA (US); James Parker Ferry, Cedar Hills, UT (US); Bryan Joseph Johnson, American Fork, UT (US); Alisa Sedghifar, San Francisco, CA (US); Yong Wang, San Mateo, CA (US); Shiya Song, San Mateo, CA (US); Jeffrey Adrion, Salt Lake City, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 521 days.

(21) Appl. No.: 18/134,472

(22) Filed: Apr. 13, 2023

(65) Prior Publication Data

US 2023/0335217 A1      Oct. 19, 2023

Related U.S. Application Data

(60) Provisional application No. 63/330,538, filed on Apr. 13, 2022.

(51) Int. Cl.
*G16B 20/00*      (2019.01)
*G06N 7/01*       (2023.01)
(Continued)

(52) U.S. Cl.
CPC .............. *G16B 20/00* (2019.02); *G06N 7/01* (2023.01); *G16B 20/40* (2019.02); *G16B 40/20* (2019.02)

(58) Field of Classification Search
CPC ........ G16B 20/00; G16B 20/40; G16B 40/20; G06N 7/01
See application file for complete search history.

(56) References Cited

U.S. PATENT DOCUMENTS 8,510,057 B1      8/2013  Avey et al.
9,213,944 B1     12/2015  Do et al.
(Continued)

FOREIGN PATENT DOCUMENTS

CN        106846029 A    6/2017
WO    WO 2014/151088 A2  9/2014
(Continued)

OTHER PUBLICATIONS

23andMe. "Ancestry Composition: 23andMe's State-of-the-Art Geographic Ancestry Analysis." 23andme.com, Sep. 5, 2015, 10 pages, [Online] [Retrieved Jan. 26, 2024], Retrieved from the Internet Archive <URL:https://web.archive.org/web/20150905120544/https://www.23andme.com/ancestry_composition_guide/>.
(Continued)

*Primary Examiner* — Kenneth B Lee, Jr.
(74) *Attorney, Agent, or Firm* — Fenwick & West LLP

(57)      ABSTRACT

Disclosed is a configuration for determining a genotyping label composition of a target individual using direct acyclic paths. The configuration includes receiving a phased genotype of the target individual, including a first haplotype and a second haplotype. The configuration initiates a full-ethnicity hidden Markov model (HMM) including nodes with a set of ethnicity labels. The first haplotype is input to determine a first subset of ethnicity labels that match the first haplotype. The second haplotype is input to determine a second subset of ethnicity labels that match the second haplotype. The first and second subsets of ethnicity labels are combined to create a candidate subset of ethnicity labels for the target individual. The configuration initiates a sim- (Continued)

100

Client Device
110

User Interface
115

Genetic Data
Extraction Service
Server
125

Client Device
110

User Interface
115

Network
120

Client Device
110

User Interface
115

Computing
Server
130 plified HMM with nodes from the candidate subset of ethnicity labels. The phased genotype of the target individual is input to the simplified HMM to determine genotyping label composition of the target individual.

20 Claims, 18 Drawing Sheets

(51) Int. Cl.
G16B 20/40       (2019.01)
G16B 40/20       (2019.01)

(56) References Cited

U.S. PATENT DOCUMENTS

| | | | |
|---|---|---|---|
| 9,213,947 B1 | 12/2015 | Do et al. | |
| 9,367,800 B1 | 6/2016 | Do et al. | |
| 9,836,576 B1 | 12/2017 | Do et al. | |
| 9,910,962 B1 | 3/2018 | Fakhrai-Rad et al. | |
| 9,940,433 B2 | 4/2018 | Han et al. | |
| 9,977,708 B1 * | 5/2018 | Do | G06F 3/04812 |
| 10,114,922 B2 | 10/2018 | Byrnes et al. | |
| 10,223,498 B2 | 3/2019 | Han et al. | |
| 10,558,930 B2 | 2/2020 | Noto et al. | |
| 10,692,587 B2 | 6/2020 | Song et al. | |
| 10,720,229 B2 | 7/2020 | Barber et al. | |
| 11,211,149 B2 | 12/2021 | Curtis et al. | |
| 11,232,854 B2 | 1/2022 | Anderson et al. | |
| 2002/0143578 A1 | 10/2002 | Cole et al. | |
| 2002/0156596 A1 | 10/2002 | Caruso et al. | |
| 2003/0113727 A1 | 6/2003 | Girn et al. | |
| 2004/0267458 A1 | 12/2004 | Judson et al. | |
| 2005/0025508 A1 | 2/2005 | Karakama et al. | |
| 2005/0255508 A1 | 11/2005 | Casey et al. | |
| 2008/0154566 A1 | 6/2008 | Myres et al. | |
| 2008/0228043 A1 | 9/2008 | Kenedy et al. | |
| 2008/0255768 A1 * | 10/2008 | Martin | G16B 40/00 |
| | | | 702/20 |
| 2010/0256917 A1 | 10/2010 | McVean et al. | |
| 2013/0085728 A1 * | 4/2013 | Tang | G16B 40/00 |
| | | | 703/2 |
| 2013/0149707 A1 | 6/2013 | Sorenson et al. | |
| 2013/0163860 A1 | 6/2013 | Suzuki et al. | |
| 2013/0297221 A1 | 11/2013 | Johnson et al. | |
| 2014/0045705 A1 * | 2/2014 | Bustamante | G16B 20/20 |
| | | | 506/2 |
| 2014/0045708 A1 | 2/2014 | Feng et al. | |
| 2014/0067355 A1 | 3/2014 | Noto et al. | |
| 2014/0108527 A1 | 4/2014 | Aravanis et al. | |
| 2014/0194300 A1 | 7/2014 | Song et al. | |
| 2015/0106115 A1 | 4/2015 | Hu et al. | |
| 2016/0350479 A1 | 12/2016 | Han et al. | |
| 2017/0017752 A1 | 1/2017 | Noto et al. | |
| 2017/0062577 A1 | 3/2017 | Brewer et al. | |
| 2017/0220738 A1 | 8/2017 | Barber et al. | |
| 2017/0262577 A1 | 9/2017 | Ball et al. | |
| 2017/0329904 A1 | 11/2017 | Naughton et al. | |
| 2018/0329033 A1 | 11/2018 | Pratt et al. | |
| 2018/0330824 A1 | 11/2018 | Athey et al. | |
| 2019/0114219 A1 | 4/2019 | Do et al. | |
| 2020/0005899 A1 | 1/2020 | Nicula et al. | |
| 2020/0082909 A1 * | 3/2020 | Wang | G16B 50/10 |
| 2020/0160202 A1 | 5/2020 | Noto et al. | |
| 2020/0286579 A1 | 9/2020 | Song et al. | |
| 2021/0134387 A1 | 5/2021 | McMaster-Schraiber et al. | |
| 2022/0051751 A1 * | 2/2022 | Wilton | G16B 40/00 |

FOREIGN PATENT DOCUMENTS

| | | |
|---|---|---|
| WO | WO 2015/051006 A2 | 4/2015 |
| WO | WO 2016/061568 A1 | 4/2016 |
| WO | WO 2018/129413 A1 | 7/2018 |
| WO | WO 2020/053789 A1 | 3/2020 |

OTHER PUBLICATIONS

Alexander, D. H. et al. "Fast Model-Based Estimation of Ancestry in Unrelated Individuals." Genome Research, vol. 19, Jul. 31, 2009, pp. 1655-1664.

Ball, C. A. et al. "AncestryDNA Matching White Paper: Discovering Genetic Matches Across a Massive, Expanding Genetic Database." AncestryDNA, Mar. 31, 2016, pp. 1-46.

Baran, Y. et al. "Fast and Accurate Inference of Local Ancestry in Latino Populations." Bioinformatics, vol. 28, No. 10, May 2012, pp. 1359-1367.

Bastian, M. et al. "Gephi: An Open Source Software for Exploring and Manipulating Networks." Proceedings of the Third International AAAI Conference on Weblogs and Social Media, vol. 3, No. 1, Mar. 19, 2009, pp. 361-362.

Bercovici, S. et al. "Ancestry Inference in Complex Admixtures via Variable-Length Markov Chain Linkage Models." Proceedings of the 16th Annual International Conference on Research in Computational Molecular Biology, Apr. 2012, pp. 12-28.

Brisbin, A. et al. "PCAdmix: Principal Components-Based Assignment of Ancestry along Each Chromosome in Individuals with Admixed Ancestry from Two or More Populations." Human Biology, vol. 84, No. 4, Aug. 2012, pp. 343-364.

Brooks, R. R. et al. "Behavior Detection Using Confidence Intervals of Hidden Markov Models." IEEE Transactions on Systems, Man, and Cybernetics—Part B: Cybernetics, vol. 39, No. 6, Dec. 2009, pp. 1484-1492.

Browning, B. L. et al. "A Fast, Powerful Method for Detecting Identity by Descent," The American Journal of Human Genetics, Feb. 11, 2011, vol. 88, No. 2, pp. 173-182.

Browning, B. L. et al. "A Unified Approach to Genotype Imputation and Haplotype Phase Inference for Large Data sets of Trios and Unrelated Individuals," The American Journal of Human Genetics, Feb. 13, 2009, pp. 210-223, vol. 84.

Browning, B. L. et al. "Detecting Identity by Descent and Estimating Genotype Error Rates in Sequence Data." The American Journal of Human Genetics, vol. 93, Nov. 7, 2013, pp. 840-851.

Browning, B. L. et al. "Efficient Multilocus Association Testing for Whole Genome Association Studies Using Localized Haplotype Clustering." Genetic Epidemiology, vol. 31, Feb. 26, 2007, pp. 365-375.

Browning, B. L. et al. "Genotype Imputation with Millions of Reference Samples." The American Journal of Human Genetics, vol. 98, Jan. 7, 2016, pp. 116-126.

Browning, S. R. "Multilocus Association Mapping Using Variable-Length Markov Chains." American Journal of Human Genetics, Jun. 2006, pp. 903-913, vol. 78, No. 6.

Browning, S. R. et al. "Haplotype Phasing: Existing Methods and New Developments." Nature Reviews Genetics, Author Manuscript, vol. 12, No. 10, Oct. 2011, pp. 703-714.

Browning, S. R. et al. "Rapid and Accurate Haplotype Phasing and Missing-Data Inference for Whole-Genome Association Studies by Use of Localized Haplotype Clustering." American Journal of Human Genetics, vol. 81, Nov. 2007, pp. 1084-1096.

Cann, H. M. et al. "A Human Genome Diversity Cell Line Panel." Science, vol. 296, No. 5566, Apr. 12, 2002, pp. 261-262.

Cavalli-Sforza, L. L. "The Human Genome Diversity Project: Past, Present and Future." Nature Reviews Genetics, vol. 6, Apr. 1, 2005, pp. 333-340.

De Roos, A. P. W. "Genomic Selection in Dairy Cattle." Dissertation, Wageningen University, Jan. 21, 2011, pp. 1-185.

Dilthey, A. et al. "Multi-Population Classical HLA Type Imputation." PLoS Computational Biology, vol. 9, No. 2, Feb. 2013, pp. 1-13.

Dilthey, A. et al. "Multi-Population Classical HLA Type Imputation." Supporting Text S1, PLoS Computational Biology, vol. 9, No. 2, Feb. 2013, pp. 1-17.

Durand, E. Y. et al. "Reducing Pervasive False-Positive Identical-by-Descent Segments Detected by Large-Scale Pedigree Analysis." Molecular Biology and Evolution, vol. 31, No. 8, Aug. 2014, pp. 2212-2222.

(56)                    References Cited

OTHER PUBLICATIONS

Eronen, L. et al. "A Markov Chain Approach to Reconstruction of Long Haplotypes." Pacific Symposium on Biocomputing, Jan. 1, 2004, pp. 1-12.

Falush, D. et al., "Inference of Population Structure Using Multilocus Genotype Data: Linked Loci and Correlated Allele Frequencies," Genetics, vol. 164, Aug. 2003, pp. 1567-1587.

Ghahramani, Z. "An Introduction to Hidden Markov Models and Bayesian Networks." International Journal of Pattern Recognition and Artificial Intelligence, vol. 15, No. 1, Jun. 2001, pp. 9-42.

Gravel, S. "Population Genetics Models of Local Ancestry." Genetics, vol. 191, No. 2, Jun. 1, 2012, pp. 607-619.

Guan, Y. "Detecting Structure of Haplotypes and Local Ancestry." Genetics, vol. 196, No. 3, Mar. 1, 2014, pp. 625-642.

Halperin, E. et al. "Haplotype Reconstruction from Genotype Data Using Imperfect Phylogeny." Bioinformatics, vol. 20, No. 12, Aug. 2004, pp. 1842-1849.

Han, E. et al. "Clustering of 770,000 Genomes Reveals Post-Colonial Population Structure of North America." Nature Communications, vol. 8, Feb. 7, 2017, pp. 1-12.

Harvard. "Plink . . . Whole Genome Association Analysis Toolset." Harvard.edu, Sep. 9, 2019, 4 pages, [Online] [Retrieved Jan. 29, 2024], Retrieved from the Internet Archive <URL:https://web.archive.org/web/20190909194835/zzz.bwh.harvard.edu/plink/>.

Hellenthal, G. et al. "A Genetic Atlas of Human Admixture History." Science, vol. 343, No. 6172, Feb. 14, 2014, pp. 747-751.

Hoggart, C. J. et al. "Design and Analysis of Admixture Mapping Studies." The American Journal of Human Genetics, vol. 74, No. 5, May 2004, pp. 965-978.

Horton, R. et al. "Variation Analysis and Gene Annotation of Eight MHC Haplotypes: The MHC Haplotype Project." vol. 60, Jan. 10, 2008, pp. 1-18.

Howie, B. N. et al. "A Flexible and Accurate Genotype Imputation Method for the Next Generation of Genome-Wide Association Studies." PLoS Genetics, vol. 5, No. 6, Jun. 2009, pp. 1-15.

Hug, N. "Surprise: A Python Scikit for Recommender Systems." Surpriselib.com, Overview, Sep. 2019, 6 pages, [Online] [Retrieved Jan. 31, 2024], Retrieved from the Internet <URL:https://surpriselib.com/>.

Itan, Y. et al. "The Origins of Lactase Persistence in Europe." PLoS Computational Biology, vol. 5, No. 8, Aug. 2009, pp. 1-13.

Jarvis, J.P. et al., "Patterns of Ancestry of Natural Selection and Genetic Association with Stature in Western African Pygmies," PLoS Genetics, vol. 8, Iss. 4, Apr. 26, 2012, pp. 1-15.

Joshi, S. et al. "Identifiable Phenotyping using Constrained Non-Negative Matrix Factorization." Proceedings of Machine Learning for Healthcare, vol. 56, Aug. 19-20, 2016, pp. 1-24.

Ke, X. et al. "Singleton SNPs in the Human Genome and Implications for Genome-Wide Association Studies." European Journal of Human Genetics, vol. 16, Jan. 16, 2008, pp. 506-515.

Khodabandelou, G. et al. "Genome Functional Annotation Across Species Using Deep Convolutional Neural Networks." bioRxiv: The Preprint Server for Biology, Jun. 7, 2019, pp. 1-11.

Krogh, A. S. "Hidden Markov Models for Labeled Sequences." Proceedings of the 12th IAPR International Conference on Pattern Recognition, vol. 3, Oct. 9-13, 1994, pp. 140-144.

Lawson, D. J. et al. "Inference of Population Structure Using Dense Haplotype Data." PLoS Genetics, vol. 8, No. 1, Jan. 2012, pp. 1-16.

Li, J. et al. "Towards Unsupervised Gene Selection: A Matrix Factorization Framework." IEEE/ACM Transactions on Computational Biology and Bioinformatics, vol. 14, No. 3, May-Jun. 2017, pp. 514-521.

Li, N. et al. "Modeling Linkage Disequilibrium and Identifying Recombination Hotspots Using Single-Nucleotide Polymorphism Data." Genetics, vol. 165, No. 4, Dec. 1, 2003, pp. 2213-2233.

Li, Y. et al. "Genotype Imputation." Annual Review of Genomics and Human Genetics, vol. 10, Sep. 2009, pp. 387-406.

Li, Y. et al. "MaCH: Using Sequence and Genotype Data to Estimate Haplotypes and Unobserved Genotypes." Genetic Epidemiology, vol. 34, No. 8, Dec. 2010, pp. 816-834.

Liu, E. Y. et al. "MaCH-Admix: Genotype Imputation for Admixed Populations." Genetic Epidemiology, vol. 37, No. 1, Jan. 2013, pp. 25-37.

Loh, P-R. et al. "Inferring Admixture Histories of Human Populations Using Linkage Disequilibrium." Genetics, vol. 193, No. 4, Apr. 1, 2013, pp. 1233-1254.

Lu, C. et al. "A Normalized Statistical Metric Space for Hidden Markov Models." IEEE Transactions on Cybernetics, vol. 43, No. 3, Jun. 2013, pp. 806-819.

Ma, P. et al. "Comparison of Different Methods for Imputing Genome-Wide Marker Genotypes in Swedish and Finnish Red Cattle." Journal of Dairy Science, vol. 96, No. 7, Jul. 2013, pp. 4666-4677.

Ma, Y. et al. "Accurate Inference of Local Phased Ancestry of Modern Admixed Populations." Scientific Reports, vol. 4, Jul. 23, 2014, pp. 1-5.

Maples, B. K. et al. "RFMix: A Discriminative Modeling Approach for Rapid and Robust Local-Ancestry Inference." The American Journal of Human Genetics, vol. 93, Aug. 8, 2013, pp. 278-288.

McPeek, M. S. et al. "Assessment of Linkage Disequilibrium by the Decay of Haplotype Sharing, with Application to Fine-Scale Genetic Mapping." American Journal of Human Genetics, vol. 65, No. 3, Sep. 1, 1999, pp. 858-875.

Montesinos-López, O. A. et al. "Prediction of Multiple-Trait and Multiple-Environment Genomic Data Using Recommender Systems." G3 Genes/Genomes/Genetics, vol. 8, No. 1, Jan. 1, 2018, pp. 131-147.

Moreno-Estrada, A. et al. "Reconstructing the Population Genetic History of the Caribbean." PLoS Genetics, vol. 9, No. 11, Nov. 2013, pp. 1-19.

Morrison, A.C. et al., "Prediction of Coronary Heart Disease Risk using a Genetic Risk Score: The Atherosclerosis Risk in Communities Study," American Journal of Epidemiology, vol. 166, No. 1, Apr. 18, 2007, pp. 28-35.

Noto, K. et al. "Polly: A Novel Approach for Estimating Local and Global Admixture Proportion Based on Rich Haplotype Models." ASHG 2015 Abstracts, Abstract 322, The American Society of Human Genetics 65th Annual Meeting, Oct. 6-10, 2015, pp. 1-2.

Noto, K. et al. "Polly: A Novel Approach for Estimating Local and Global Admixture Proportion Based on Rich Haplotype Models." Invited Talk at the American Society of Human Genetics (ASHG) Annual Meeting, Baltimore, MD, Oct. 6-10, 2015, pp. 1-6.

Noto, K. et al. "Underdog: A Fully-Supervised Phasing Algorithm that Learns from Hundreds of Thousands of Samples and Phases in Minutes." ASHG 2014 Abstracts, Abstract 155, The American Society of Human Genetics 64th Annual Meeting, Oct. 18-22, 2014, pp. 1-2.

Pașaniuc, B et al. "Imputation-Based Local Ancestry Inference in Admixed Populations." International Symposium on Bioinformatics Research and Applications, May 13-16, 2009, pp. 1-13.

Pașaniuc, B. et al. "Inference of Locus-Specific Ancestry in Closely Related Populations." Bioinformatics, vol. 25, No. 12, Jun. 2009, pp. i213-i221.

Patterson, N. et al. "Population Structure and Eigenanalysis." PLoS Genetics, vol. 2, No. 12, Dec. 2006, pp. 2074-2093.

PCT International Search Report and Written Opinion, PCT Application No. PCT/US2023/018531, Jul. 21, 2023, 16 pages.

Peck, R. et al. "Introduction to Statistics and Data Analysis." Section 7.4, 3rd Edition, Nov. 11, 2008, pp. 372-377.

Peck, R. et al. "Introduction to Statistics and Data Analysis." Sections 9.2-9.3, 3rd Edition, Nov. 11, 2008, pp. 482-508.

Platt, J.C., "Probabilistic Outputs for Support Vector Machines and Comparisons to Regularized Likelihood Methods," Mar. 26, 1999, pp. 1-11.

Price, A.L. et al., "Sensitive Detection of Chromosomal Segments of Distinct Ancestry in Admixed Populations," PLoS Genetics, vol. 5, No. 6, Jun. 2009, pp. 1-18.

Pritchard, J. K. et al. "Inference of Population Structure Using Multilocus Genotype Data." Genetics, vol. 155, No. 2, Jun. 1, 2000, pp. 945-959.

Purcell, S. et al., "PLINK: A tool set for whole-genome association and population-based linkage analyses," The American Journal of Human Genetics, vol. 81, Sep. 2007, pp. 559-575.

(56)                References Cited

OTHER PUBLICATIONS

Qian, Y. et al., "Efficient clustering of identity-by-descent between multiple individuals," Bioinformatics, vol. 30, No. 7, Dec. 19, 2013, pp. 915-922.

Rabiner, L.R., "A Tutorial on Hidden Markov Models and Selected Applications in Speech Recognition," Proceedings of the IEEE, vol. 77, No. 2, Feb. 1989, pp. 257-286.

Ranciaro, A. et al. "Genetic Origins of Lactase Persistence and the Spread of Pastoralism in Africa." The American Journal of Human Genetics, vol. 94, Apr. 3, 2014, pp. 496-510.

Roach, J. C. et al. "Analysis of Genetic Inheritance in a Family Quartet by Whole-Genome Sequencing." Science, vol. 328, No. 5978, Apr. 30, 2010, pp. 636-639.

Ron, D. et al., "On the Learnability and Usage of Acyclic Probabilistic Finite Automata," Journal of Computer and System Sciences, vol. 56, 1998, pp. 133-152.

Sankararaman, S. et al. "Estimating Local Ancestry in Admixed Populations." The American Journal of Human Genetics, vol. 82, Feb. 2008, pp. 290-303.

Scheet, P. et al., "A Fast and Flexible Statistical Model for Large-Scale Population Genotype Data: Applications to Inferring Missing Genotypes and Haplotypic Phase," The American Journal of Human Genetics, vol. 78, Feb. 17, 2006, pp. 629-644.

Seligsohn, U. et al., "Genetic Susceptibility to Venous Thrombosis," The New England Journal of Medicine, vol. 344, No. 16, Apr. 19, 2001, pp. 1222-1231.

Silva, M. C. F. et al. "Development of Two Multiplex Mini-Sequencing Panels of Ancestry Informative SNPs for Studies in Latin Americans: An Application to Populations of the State of Minas Gerais (Brazil)." Genetics and Molecular Research, vol. 9, No. 4, Oct. 19, 2010, pp. 2069-2085.

Staples, J. et al., "PRIMUS: Rapid Reconstruction of Pedigrees from Genome-wide Estimates of Identity by Descent," The American Journal of Human Genetics, vol. 95, Nov. 6, 2014, pp. 553-564.

Stephens, M. et al. "Accounting for Decay of Linkage Disequilibrium in Haplotype Inference and Missing-Data Imputation." The American Journal of Human Genetics, vol. 76, No. 3, Mar. 2005, pp. 449-462.

Sturm, R. A. et al. "A Single SNP in an Evolutionary Conserved Region within Intron 86 of the HERC2 Gene Determines Human Blue-Brown Eye Color." The American Journal of Human Genetics, vol. 82, Feb. 2008, pp. 424-431.

Sundquist, A. et al., "Effect of Genetic Divergence in Identifying Ancestral Origin using HAPAA," Genome Res., vol. 18, Mar. 18, 2008, pp. 676-682.

Tang, H. et al. "Reconstructing Genetic Ancestry Blocks in Admixed Individuals." The American Journal of Human Genetics, vol. 79, Jul. 2006, pp. 1-12.

Ter Braak, C. J. F. et al. "Identity-by-Descent Matrix Decomposition Using Latent Ancestral Allele Models." Genetics, vol. 185, No. 3, Jul. 1, 2010, pp. 1045-1057.

THE 1000 Genomes Project Consortium. "A Global Reference for Human Genetic Variation." Nature, vol. 526, No. 7571, Oct. 1, 2015, pp. 68-74.

The International Hapmap 3 Consortium, "Integrating common and rare genetic variation in diverse human populations," Nature, vol. 467, Sep. 2, 2010, pp. 52-58.

The International Hapmap Consortium. "A Second Generation Human Haplotype Map of Over 3.1 Million SNPs." Nature, Author Manuscript, Oct. 18, 2007, vol. 449, No. 7164, pp. 1-30.

The International Hapmap Consortium. "A Haplotype Map of the Human Genome." Nature, vol. 437, Oct. 27, 2005, pp. 1299-1320.

Tipping, M.E., "Sparse Bayesian Learning and the Relevance Vector Machine," Journal of Machine Learning Research, Jun. 2001, pp. 211-244.

Wang, Y. et al. "Ancestry Inference Using Reference Labeled Clusters of Haplotypes." BMC Bioinformatics, vol. 22, Sep. 25, 2021, pp. 1-14.

Weedon, M.N. et al., "Combining Information from Common Type 2 Diabetes Risk Polymorphisms Improves Disease Prediction," PLoS Med., vol. 3, Iss. 10, Oct. 2006, pp. 1877-1882.

Wikipedia. "Ethnicity." Wikipedia: The Free Encyclopedia, Jul. 30, 2022, 12 pages, [Online] [Retrieved Sep. 27, 2023], Retrieved from the Internet <URL:https://en.wikipedia.org/wiki/Ethnicity>.

Wikipedia. "Inverse Distance Weighting." Wikipedia: The Free Encyclopedia, Dec. 6, 2023, 4 pages, [Online] [Retrieved Jan. 30, 2024], Retrieved from the Internet <URL:https://en.wikipedia.org/wiki/Inverse_distance_weighting>.

Williams, A. L. et al. "Phasing of Many Thousands of Genotyped Samples." The American Journal of Human Genetics, vol. 91, Aug. 10, 2012, pp. 238-251.

Yang, Q. et al., "Improving the Prediction of Complex Diseases by Testing for Multiple Disease-Susceptibility Genes," American Journal of Human Genetics, vol. 72, Feb. 14, 2003, pp. 636-649.

Yoon, B.-J., "Hidden Markov Models and their Applications in Biological Sequence Analysis," Current Genomics, vol. 10, Sep. 2009, pp. 402-415.

Zeng, X. et al. "Probability-Based Collaborative Filtering Model for Predicting Gene-Disease Associations." BMC Medical Genomics, vol. 10, No. 76, Dec. 28, 2017, pp. 45-53.

Zhao, H. et al. "Haplotype Analysis in Population Genetics and Association Studies." Pharmacogenomics, vol. 4, No. 2, Mar. 1, 2003, pp. 171-178.

* cited by examiner

FIG. 3G

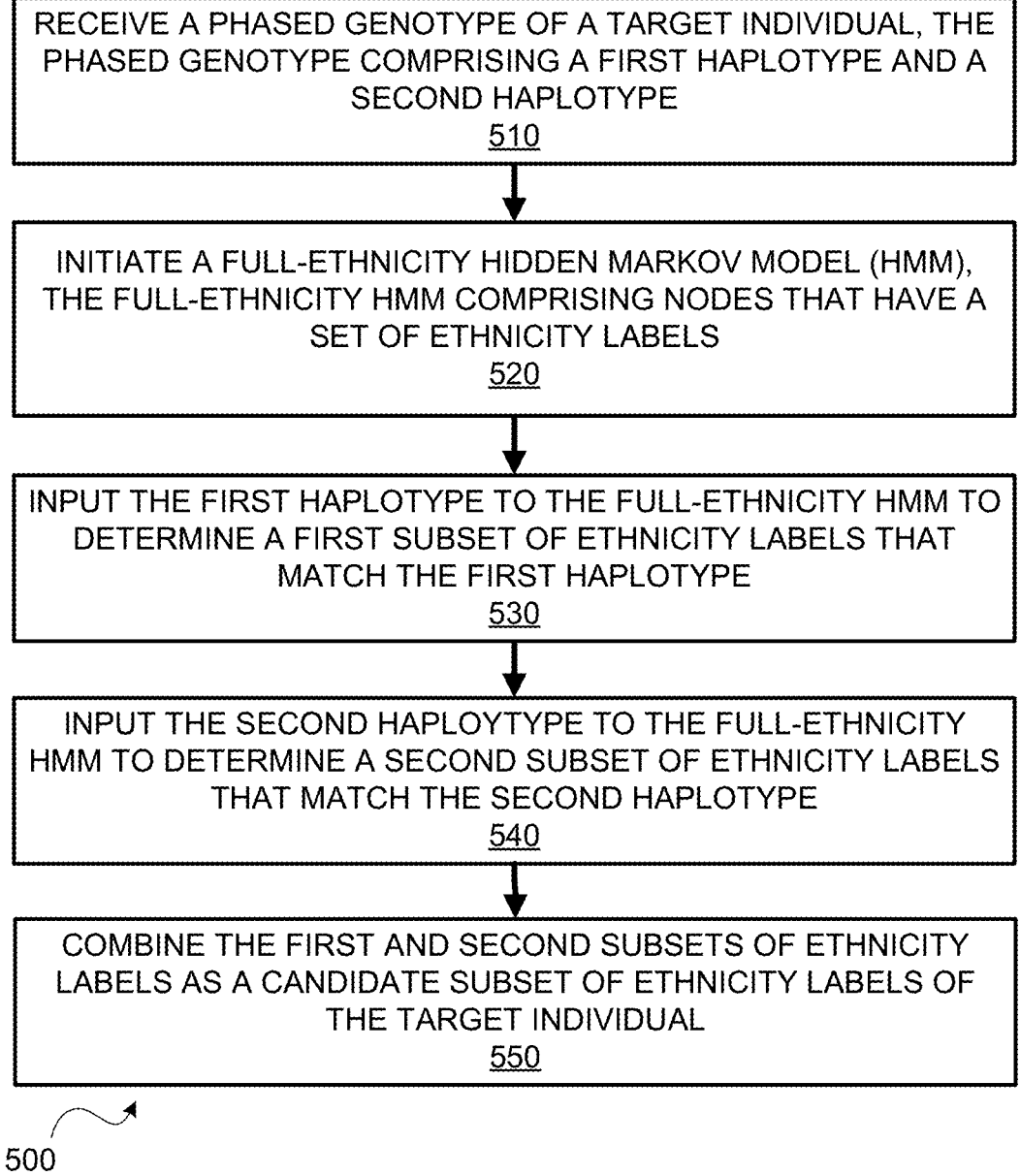

RECEIVE A PHASED GENOTYPE OF A TARGET INDIVIDUAL, THE PHASED GENOTYPE COMPRISING A FIRST HAPLOTYPE AND A SECOND HAPLOTYPE
510

INITIATE A FULL-ETHNICITY HIDDEN MARKOV MODEL (HMM), THE FULL-ETHNICITY HMM COMPRISING NODES THAT HAVE A SET OF ETHNICITY LABELS
520

INPUT THE FIRST HAPLOTYPE TO THE FULL-ETHNICITY HMM TO DETERMINE A FIRST SUBSET OF ETHNICITY LABELS THAT MATCH THE FIRST HAPLOTYPE
530

INPUT THE SECOND HAPLOYTYPE TO THE FULL-ETHNICITY HMM TO DETERMINE A SECOND SUBSET OF ETHNICITY LABELS THAT MATCH THE SECOND HAPLOTYPE
540

COMBINE THE FIRST AND SECOND SUBSETS OF ETHNICITY LABELS AS A CANDIDATE SUBSET OF ETHNICITY LABELS OF THE TARGET INDIVIDUAL
550

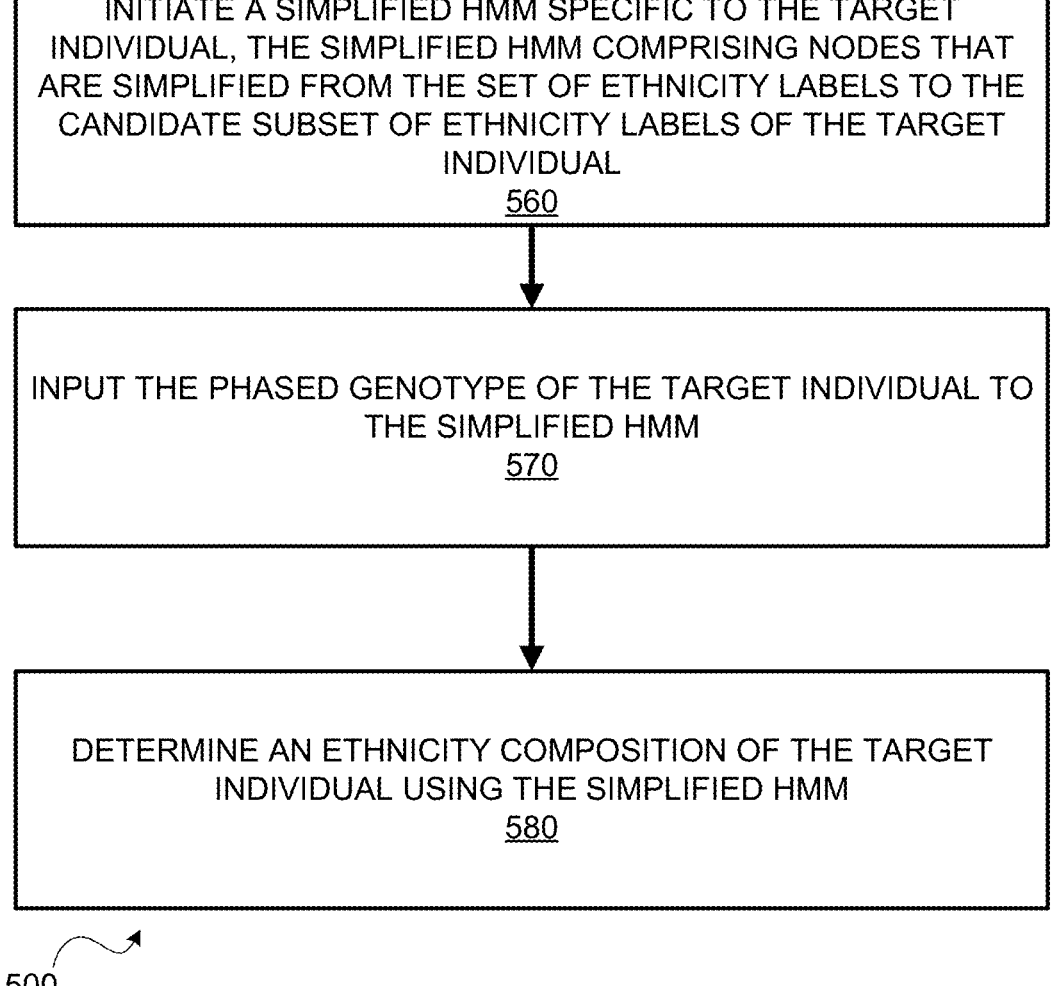

INITIATE A SIMPLIFIED HMM SPECIFIC TO THE TARGET INDIVIDUAL, THE SIMPLIFIED HMM COMPRISING NODES THAT ARE SIMPLIFIED FROM THE SET OF ETHNICITY LABELS TO THE CANDIDATE SUBSET OF ETHNICITY LABELS OF THE TARGET INDIVIDUAL
560

INPUT THE PHASED GENOTYPE OF THE TARGET INDIVIDUAL TO THE SIMPLIFIED HMM
570

DETERMINE AN ETHNICITY COMPOSITION OF THE TARGET INDIVIDUAL USING THE SIMPLIFIED HMM
580

First Haplotype
610

Second Haplotype
620

Detailed comparison

Same data, more detail. This chart shows the percentages of each ethnicity you inherited from your parents. Added together, the percents from each parent for a region equals your percent for that region.

| Region | Parent 1 | Parent 2 | You |
|--------|----------|----------|-----|
| S | 50% | 50% | 100% |
| Japan | 0% | 49% | 49% |
| England & Northwestern Europe | 37% | 0% | 37% |
| Scotland | 10% | 0% | 10% |
| Wales | 3% | 0% | 3% |
| Southern Japanese Islands | 0% | 1% | 1% |

ACCELERATED HIDDEN MARKOV MODELS FOR GENOTYPE ANALYSIS

CROSS-REFERENCE TO RELATED APPLICATION

The present application claims the benefit of U.S. Provisional Patent Application No. 63/330,538 filed on Apr. 13, 2022, which is hereby incorporated by reference in its entirety.

FIELD

The disclosed embodiments relate to systems, methods, and/or computer-program products configured for determining parental ethnicity.

BACKGROUND

Although humans are, genetically speaking, almost entirely identical, small differences in human DNA are responsible for much of the variation between individuals. For example, a sequence variation at one position in DNA between individuals is known as a single-nucleotide polymorphism (SNP). Stretches of DNA inherited together from a single parent are referred to as haplotypes (e.g., one haplotype inherited from the mother and another haplotype inherited from the father).

A subset of the SNPs in an individual's genome may be detected with SNP genotyping. Through SNP genotyping, the pair of alleles for a SNP at a given location in each haplotype may be identified. For example, an SNP may be identified as heterozygous (i.e., one allele of each type), homozygous (i.e., both alleles of the same type), or unknown. SNP genotyping identifies the pair of alleles for a given genotype, but does not identify which allele corresponds to which haplotype, i.e., SNP genotyping does not identify the homomorphic chromosome (of the homomorphic pair) to which each allele corresponds. This is partially due to current physical sequencing techniques will typically generate two signals at a heterozygous position. Thus, successful SNP genotyping produces an unordered pair of alleles, where each allele corresponds to one of two haplotypes.

In general, most of the SNPs of a haplotype that correspond to a particular chromosome are sourced from a single chromosome from a parent. However, some of the SNPs from the haplotype may correspond to the parent's other homomorphic chromosome due to chromosomal crossover. Because the genetic information in a particular chromosome of an individual mostly corresponds to a single chromosome of a parent, sequences of SNPs tend to stay relatively intact across generations.

Efforts to predict an individual's ethnicity have been limited by an inability to determine which allele corresponds to which haplotype (e.g., the homomorphic chromosome to which each allele corresponds). Genotyping is performed by physical sequencing that is unable to distinguish the order of a pair of alleles at a given SNP position. As such, there is currently no way to determine with confidence one or both parents' ethnicity, community, traits, etc. from an individual's genome without the parents' DNA.

SUMMARY

Disclosed herein relates to example embodiments that determine an ethnicity composition of a target individual. In one embodiment, the computer-implemented method receives a phased genotype of a target individual. The phased genotype includes a first haplotype and a second haplotype. The computer-implemented method may initiate a full-ethnicity hidden Markov model (HMM) including nodes that have a set of ethnicity labels. Each ethnicity label may represent a different ethnic origin. The computer-implemented method may input the first haplotype to the full-ethnicity HMM to determine a first subset of ethnicity labels that match the first haplotype. The computer-implemented method may input the second haplotype to the full-ethnicity HMM to determine a second subset of ethnicity labels that match the second haplotype. The computer-implemented method may combine the first and second subsets of ethnicity labels to create a candidate subset of ethnicity labels of the target individual. The computer-implemented method may initiate a simplified HMM specific to the target individual. The simplified HMM may include nodes that are simplified from the set of ethnicity labels to the candidate subset of ethnicity labels of the target individual. The computer-implemented method may input the phased genotype of the target individual to the simplified HMM. The computer implemented method may determine an ethnicity composition of the target individual using the simplified HMM.

In yet another embodiment, a non-transitory computer-readable medium that is configured to store instructions is described. The instructions, when executed by one or more processors, cause the one or more processors to perform a process that includes steps described in the above computer-implemented methods or described in any embodiments of this disclosure. In yet another embodiment, a system may include one or more processors and a storage medium that is configured to store instructions. The instructions, when executed by one or more processors, cause the one or more processors to perform a process that includes steps described in the above computer-implemented methods or described in any embodiments of this disclosure.

BRIEF DESCRIPTION OF THE DRAWINGS

FIGS. 3C, 3D, 3E, 3F, and 3G are conceptual diagrams explaining the pipeline of a jig phasing algorithm that produces a higher confidence of long distance phasing accuracy, in accordance with some embodiments.

FIG. 5A and FIG. 5B are flowcharts depicting an example method for determining the ethnicity composition of a target individual, in accordance with some embodiments.

Figure 1:
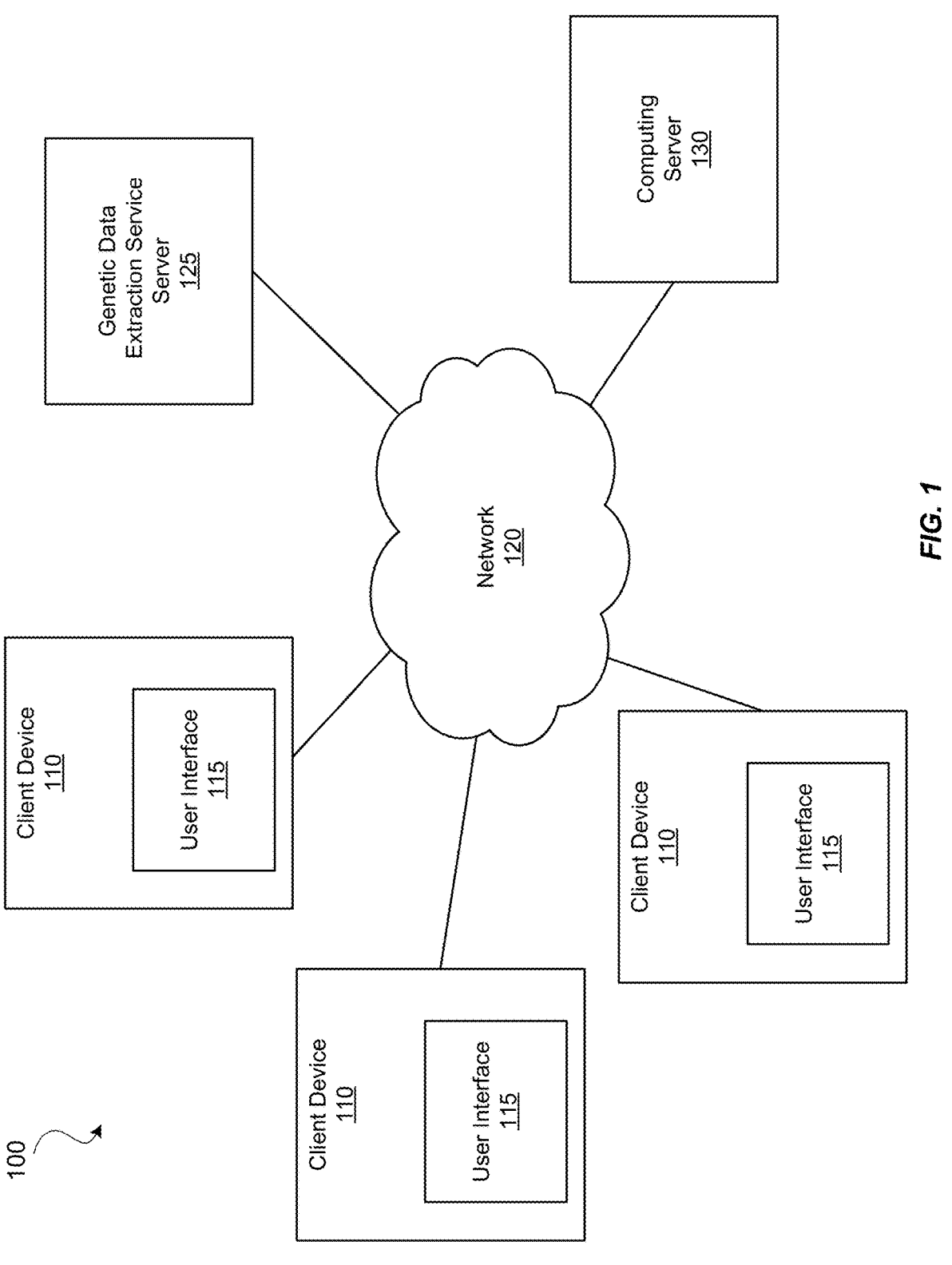
FIG. 1 illustrates a diagram of a system environment of an example computing system, in accordance with some embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures (FIGS.) and the following description relate to preferred embodiments by way of illustration only. One of skill in the art may recognize alternative embodiments of the structures and methods disclosed herein as viable alternatives that may be employed without departing from the principles of what is disclosed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Process Overview

A system architecture is described to increase the efficiency of determining an ethnicity composition of a target individual. Embodiments of parental ethnicity determination systems, methods, and non-transitory computer-readable mediums disclosed herein address shortcomings in the art by facilitating the determination of an individual's ethnicity according to one or both of the individual's parents. Individuals, who may be customers of a company operating the computing server, provide a genetic sample for analysis. The individual's genotype may be phased into two distinct haplotypes, each corresponding to one parent of the individual.

The computing server determines the ethnicity compositions for each haplotype using directed acyclic graphs. For example, hidden Markov models are examples of directed acyclic graphs that may be used to determine an ethnicity composition for each haplotype. The computing server may determine the haplotypes of a genotype of a target individual with a long-distance (e.g., cross-chromosome) confidence of accuracy of separation between two haplotypes. Each node in a hidden Markov model is labeled with an ethnicity label. The computing server identifies a set of ethnicity labels that match each haplotype. A full-ethnicity HMM is initiated with each ethnicity label from the set of ethnicity labels. The computing server determines a candidate subset of ethnicity labels that match one or both of the haplotypes. The computing server initiates a simplified HMM with only the ethnicity labels from the candidate subset. Each node in the simplified HMM may include three labels, one for a first parent ethnicity, one for a second parent ethnicity, and one switch label. The switch label accounts for a phasing error of switching the first and second parent ethnicity labels from one node group to the next node group. The computing server uses the simplified HMM to determine the ethnicity composition of the target individual. Rather than running the simplified HMM with three labels per node for every ethnicity possible in the computing server, only the ethnicities determined to be relevant to the two haplotypes are used in the simplified HMM. By limiting the number of ethnicity labels used for the simplified HMM, the computing server makes the process of determining the haplotype ethnicity compositions more efficient.

Genetic Data Overview

Individuals may provide deoxyribonucleic acid (DNA) samples (e.g., saliva, skin cells, blood, or other biological matter) for analysis of their genetic data. In one embodiment, an individual uses a sample collection kit to provide a sample from which genetic data can be reliably extracted according to conventional methods. A DNA extraction service can receive the sample, for example by extracting the DNA from the sample and identifying values of SNPs present within the DNA. The DNA extraction service may perform genotyping of the DNA sample such as by performing amplification and physical sequencing (e.g., SNP assays or NextGen sequencing). The result may be referred to as a genotype dataset of the individual. In this disclosure, the result may be an input genotype dataset for further processing based on various processes described in further detail below. The genotype dataset is often a diploid genotype. A DNA quality control and matching preparation service may assess the data quality of the diploid genotype by checking various attributes such as genotyping call rate, genotyping heterozygosity rate, and agreement between genetic and self-reported gender. The genotype dataset (sometimes also referred to as genotype, or input sample genotype dataset X) is sent (e.g., transmitted through a network) to a computing server. The computing server may receive the genotype from the DNA extraction service or from the DNA quality control and matching preparation service and may store the genotype (e.g., in a database).

A genotype dataset of an individual may include a plurality of SNPs (e.g., say L SNPs). The genotype dataset may be analyzed on a set of targeted sites of SNPs (e.g., known variable locations of DNA in the human genome). Since most SNPs manifest as one of two possible allelic variations within a population (e.g., an SNP may be adenine (A) in some individuals, but cytosine (C) in others), an allele for a particular SNP of a genotype may be referenced by either 0 or 1 (e.g., 0 for A and 1 for C) without loss of generality. Furthermore, although described herein are as using biallelic SNPs (e.g., SNPs that can take on two possible alleles), the methods and systems described herein may be generalized to include multiallelic SNPs (e.g., triallelic SNPs). Additionally, instead of using individual alleles as the basic unit of a genotype dataset, the methods and systems herein may use "mini haplotypes" that include multiple alleles as the basic units of data.

A pair of alleles for an SNP in a genotype dataset of an individual may be received without information indicating the homomorphic chromosome to which each allele corresponds. Thus, genotyping data may include a sequence of L SNPs, each of which contains an unordered pair of values: (0,0) (i.e., homozygous 0), (0,1) (i.e., heterozygous), or (1,1)

(i.e., homozygous 1). The first binary value in a pair may be associated with a first parent value and the second binary value may be associated with a second parent value, or vice versa. In some instances, genotyping a particular SNP fails, in which case the alleles for that SNP may be missing. Herein, a genotype dataset may be represented as $G=(G_1, G_2, \ldots, G_L)$, where each $G_i$ (for $i \in \{1, \ldots, L\}$) is an SNP that has a value of either (0,0), (0,1), (1,1), or missing data.

A genotype dataset G may be divided in W windows, where each window w (for $w \in \{1, \ldots, W\}$) is a sequence of SNPs (i.e., a sub-sequence of G). Each window may include a set of sites of SNPs. The sites may correspond to consecutive DNA sequence locations in human chromosomes (e.g., every consecutive location of a DNA sequence is a targeted site), but may also be selected sites in which neighboring sites do not necessarily correspond to neighboring locations in the DNA sequence (e.g., a first SNP site may be at a position A in a DNA sequence while a second SNP site may be at B in the DNA sequence that is hundreds of base pair apart from the position A). In one specific example, each window w includes about 2,000 SNP sites so that the portion of the sequence G corresponding to a window has about 2,000 binary values. The windows may overlap (i.e., share one or more sites of SNPs). For example, a first window may include the first 2,000 sites of SNPs in a chromosome while a second window may include 1,500th to 3,000th sites of SNPs in the chromosome. In one embodiment, a limitation may be imposed such that no window w includes SNPs from more than one chromosome (e.g., from more than one pair of homomorphic chromosomes). For this disclosure, the start point of each window w may be denoted as an SNP index $S_w$ and the length of the window may be denoted as $D_w$. Thus, the sequence of SNPs of the genotype G in window w is $(G_{S_w}, \ldots, G_{(S_w+D_w-)})$.

Using a phasing algorithm, the genotype G can be phased into a pair of phased haplotype datasets H1 and H2 and the entire sequence can be represented as (H11, H12), (H21, H22), (H31, H32), etc., where Hi1 and Hi2 represent i-th SNP. In some embodiments, the phasing algorithm may be a specific algorithm that is capable of yielding long-distance accuracy of haplotype separation. For example, a conventional phasing algorithm may only be able to generate haplotypes that have local separation accuracy. In other words, oftentimes, for conventional phasing algorithms, the confidence of the phasing being correct is only high for a particular segment within a genetic locus or within a short span of the genome. However, oftentimes there could be insufficient confidence that the accuracy of a segment of phasing would extend to another segment that is far away (e.g., two segments being located in different chromosomes). In some embodiments, the computing server uses a novel phasing algorithm that is described in U.S. Patent Application Publication No. US 2701/0034647, entitled "Clustering of Matched Segments to Determine Linkage of Dataset in a Database," published on Feb. 4, 2701. The phasing algorithm may be referred to as a jig phasing that provides a long-distance accuracy of separation for the pair of haplotypes. The jig phasing algorithm may be able to yield phasing accuracy in a global genomic scale. In this disclosure, global and local may refer to the distance and scale within the genomic. For example, a local determination may refer to a determination that is more limited to one or a few genetic loci. A global determination may reference a determination that is cross-chromosome or even close to the entire genome or at least a majority of the genome. For example, using the jig phasing algorithm, the computing server may have increased confidence that a haplotype at a particular genetic locus and the haplotype at another particular genetic locus that is far away (e.g., in a different chromosome) belong to the same parent.

In some embodiments, the genetic composition (e.g., ethnicity composition) of an individual may be determined based on assigning the windows of the individual genetic datasets with different labels, such as ethnicity labels. Labels could be any classification label such as genetic classification labels. In one embodiment, a label corresponds to ancestry from a historical population (e.g., ethnic group). For example, each ethnic group and corresponding label may correspond to a geographic area that the given population historically inhabited. Example areas may be North Africa, Scandinavia, South Asia, etc. For example, a computing system may assign a pair of labels (one being a first parent label such as a patrilineal label and another corresponding to a second parent label such as a matrilineal label) to each window. The labels may be selected from a set of K labels. For example, in the case where the labels are related to ethnic origin, the set of K labels may be African, Asian, European, etc. or be German, Korean, Mexican, etc., depending on the granularity of the classification. A label is an identification of some sequences of haplotypes that are genetically similar. Based on the assigned labels, information on the ethnic origin of the individual may be determined. For example, if 80% of the windows are assigned with a European label, the computing system may provide a statement that the individual is of European origin as an example of information of ethnic origin. The information on ethnic origin may also include statistics on the labels. For example, the computing system may provide a detailed breakdown of the ancestry origins (e.g., 75% European, 20% Asian, and 5% African) of the individual based on the individual's genotype dataset.

The length $D_w$ of each window w may be selected so that each window w likely to corresponds to only a single pair of labels. For example, the length $D_w$ of each window w may be selected so as to have a length of 1-10 centimorgans (cM) or less. The details of labeling of each window w will be discussed in further detail.

Label Assignment Process Overview

In accordance with some embodiments, a process to characterize a genetic dataset of an individual as a composition of different classifications is conducted through a label assignment process that makes use of different directed acyclic graphs (e.g., different HMMs). A specific example of label assignment is the determination of a composition of ethnicity origins of the individual by assigning different first parent and second parent ethnicity labels to the individual. The genotype dataset is divided into a plurality of segments (which may be called windows). Each window corresponds to a DNA locus that includes a set of SNP sites. Based on the pair of first and second parent ethnicity labels associated with each window, the total compositions of labels of the genotype dataset can be counted. For example, if there are 580 European first parent ethnicity labels assigned to a total of 1000 windows of genotype data, the genotype data is determined to have about 58% European origin on the first parent side (e.g., on the father side).

In some embodiments, the assignment of labels to a genetic dataset is conducted through a two-stage process to speed up the entire pipeline. In any stage, a statistically most likely path (commonly referred to as a Viterbi path) of an inter-window Hidden Markov Model (HMM). In some embodiments, the Viterbi path and a selection (e.g., 1000) of other multiple statistically likely paths (but not as likely as the Viterbi path) that traverse the inter-window HMM are sampled and are used to determine the statistical confidence of the Viterbi path and the final label assignments.

An inter-window HMM includes certain components. First, the inter-window HMM includes hidden states and observations. A hidden state in an HMM may be graphically represented by a node.

In an inter-window HMM in accordance with some embodiments, a hidden state may represent a possible condition of the window. Put differently, a window may take one of the multiple possible hidden states while different windows may take different hidden states. In the inter-window HMM in accordance with some embodiments, a state can be defined by up to three labels. However, as discussed further below, the HMMs in the two different stages are simplified in different ways. For example, the HMMs in the first stage may have only a single label in a state.

Disregarding the simplification of the stake of discussion for now, the three labels are two parent labels and a phasing switching label. The first two labels are a first parent label and a second parent label and these two labels are ordered. For example, either the first parent label is consistently first or the second parent label is consistently first among the states. Hence, the first pair of labels of "European, Asian" represents one of the possible states in a window for the first parent and the second parent while a second pair of labels of "Asian, European" represents another possible state that is different from the first pair of labels but corresponds to the same first parent and the same second parent. Each window for a genetic dataset may take a different state (i.e., different DNA segments of an individual are assigned with different states that have different pairs of ethnicity labels).

The third label that defines a hidden state is a switch label, which represents that, for a particular state, the order of the first parent label and second parent label in the HMM is switched compared to the actual labels in the sample. The switch label accounts for a phasing algorithm that switches the phasing compared to the true phasing. Put differently, a switching occurs when the HMM assumes a window having a pair of labels in a particular order, but the ground truth of the parental haplotype assignment is in a reversed order. For example, a label such as "first parent-European, second parent-Asian, switched" means the correct label in the genotype sample is "first parent-Asian, second parent-European." A switch label is used because, in order for first parent label and second parent label to be considered separately, the genotype dataset needs to be phased to generate a pair of haplotype datasets. However, phasing methods, even using jig phasing, are often not perfect. The switch label is used to account for the probability that the phasing is incorrect for a particular window. The switch labels may be binary, either switched or not switched.

An observation associated with a hidden state is a possible observable trait, condition, or value in a sample dataset. In an inter-window HMM in accordance with some embodiments, an observation may be the genotype sequence or phased haplotype sequence pair associated with a window. A hidden state is "hidden" because the state is not immediately apparent given the sample dataset. For example, the label "Asian, European, Not-Switched" for a particular window is not immediately apparent given only the sample genotype dataset or the phased pair of haplotype datasets at the particular window. Simply put, when a sequence of SNPs of a sample is ATGCTATAGC . . . , whether a such sequence is inherited from an Asian ancestor, a European ancestor, or another ancestor is not immediately apparent.

Second, an inter-window HMM includes emission probabilities and transition probabilities. A particular hidden state is related to a particular observation by an emission probability. The relationships between different hidden states and different observations might have different values of emission probabilities. A particular hidden state of one window is related to another hidden state of the next window by a transition probability. Graphically, the hidden states in the HMM are represented by nodes that are arranged in node groups (each node group corresponds to a window and the nodes within a node group represent different possible states). An edge that connects two nodes represents a transition with a transition probability.

An emission probability is a probability of an observation being manifested given a particular hidden state. In the inter-window HMM in accordance with some embodiments, an emission probability may represent a likelihood that a particular pair of phased haplotypes is observed in the sample datasets given a particular pair of labels is assigned to the window. Simply put, an emission probability determines what the likelihood is when the sample has the haplotype sequence pairs, for example, "ATGCTAT-AGC . . . " and "ATGGTATAGC . . . " given the window is assigned with, for example, the labels "Asian, European, not-switched." The emission probability represents how likely the DNA in a window comes from an ethnic origin.

An emission probability is associated with each hidden state and is determined based on genetic datasets of reference panels. A reference panel is a collection of individuals' genetic datasets who are known members of an ethnical population. For example, a Germanic reference panel includes genotype datasets of known Germans. The determination of an emission probability is specific to a particular hidden state with two ethnicity labels and involves a series of training steps of the HMM. Different ways, such as using other Markov models, or using another type of machine learning model such as a convolutional neural network, may be used to determine emission probabilities. Examples of the details in determining emission probabilities are described below, such as in association FIG. 3B and also a section below. At a high level, the determination of an emission probability includes comparing a sample genetic dataset of interest to one or more reference panels to determine the likelihood that the pair of haplotypes presented in each window of the sample genetic dataset comes from the populations of the reference panels.

A transition probability is a probability that a hidden state of a first node group is transitioned to another hidden state of the next node group (the neighboring window). In the inter-window HMM in accordance with some embodiments, a transition probability may represent, when a set of labels (e.g., "Asian, European, Not-Switched") is assigned to a window, the likelihood that another set of labels (e.g., same labels "Asian, European, Not-Switched" or different labels "Asian, Asian, Not-Switched") should be assigned to the next window. Humans often inherit a large chunk of DNA from an ancestor. Hence, changes in ethnicity labels are less likely when two windows are next to each other. The ethnicity labels of a window depending on the ethnicity labels of the previous window. The transition probability represents such dependence.

It should be noted that "transition" and "switch" represent different concepts in this disclosure. A transition may refer to a change of one or more of the three labels in a hidden state from one window to the next window. Graphically, in an HMM, a transition is represented by an edge, which is a path going from one node of a node group to another node of the next node group. In contrast, switching is related to a potential incorrect phasing for the haplotype pair in a particular window. Switching occurs when the HMM assumes that a window is at a state with a pair of labels in a particular order, but the actual genotype sample at that window has the same pair of labels, but in a reversed order. In the HMM, a switch label is one of the label values in a node while a transition is represented by an edge in the HMM.

Transition probabilities associated with different edges are determined based on the training of the inter-window HMM until the HMM converges or after a predetermined number of iterations. The training set of the HMM may be sampled from different reference panels such that the training set includes a mix of different ethnicity. In some cases, when a genotype dataset needs to be analyzed, the genotype dataset can first be used to further train the HMM (e.g., as an additional sample of the training set). Training may be an iterative process using a training set with training samples that have known label assignments (ground truth). The transition probabilities may be iteratively adjusted so that the values of the transition probabilities converge to values that predict labels of the training samples that are closest to the ground truth.

After the emission probabilities and transition probabilities are determined, the label assignment of a genotype dataset is determined by running a Viterbi algorithm known in the art using the genotype dataset to determine the statistically most likely path of the inter-window HMM (the Viterbi path). The path selects one node for each window (meaning a pair of ethnicity labels are assigned to each window).

In some embodiments, the determination of ethnicity labels may be performed in a two-stage process to speed up the overall determination process. In some embodiments, the combined time for performing the two-stage process may be notably reduced compared to performing the determination in a single stage because the complexity of the HMM used in each stage is significantly reduced.

By way of example, a computing server may maintain a list of N possible ethnicity labels. The actual number of possible ethnicity labels maintained by a computing server may depend on the choice of granularity of how ethnicity is defined. In some embodiments, the computing server may maintain about 100 ethnicity labels, but the precise number may vary depending on the embodiments. In some embodiments, in the first stage, the computing server may initiate a full-ethnicity inter-window HMM that has all N possible ethnicity labels. The full-ethnicity HMM is simplified from an inter-window HMM described above in that each node, instead of having three types of labels, has only one type of label, which is an ethnicity label. The full-ethnicity HMM in the first stage may also be referred to as a haploid inter-window HMM because the full-ethnicity HMM takes a single sequence of haplotype (instead of a pair of phased haplotypes or a diploid genotype) as the input. This significantly reduces the complexity of the HMM because in a full HMM that has three labels for each node, the number of possible states in a window is N×N×2 (e.g., 100×100×2). In contrast, for the haploid HMM, the number of possible states in a window is only N (e.g., 100). However, to more accurately determine transition probabilities, a more globally accurate phasing (e.g., haplotype results from jig phasing) may need to be used in the first stage because haplotype is used as an input.

The computing server may input the first haplotype (e.g., determined by a phasing algorithm that has a long-distance accuracy) of a target individual to the haploid full-ethnicity HMM to determine a first subset of ethnicity labels that match the first haplotype. The computing server may re-run the haploid full-ethnicity HMM by inputting the second haplotype of the target individual to determine a second subset of ethnicity labels that match the second haplotype. The computing server may combine the first and second subsets of ethnicity labels as a candidate subset of ethnicity labels of the target individual.

In the second stage, the phased genotype of the target individual may be analyzed fully with both haplotypes and the accounts of potential phasing errors. The computing server may initiate a simplified inter-window HMM that is specific to the target individual. The simplified inter-window HMM may be referred to as a diploid inter-window HMM or phased-accounted inter-window HMM because, in the second stage, the HMM receives both phased haplotypes as the input. However, in contrast to using all N possible ethnicity labels, the computing server only uses the candidate ethnicity labels determined in the first stage. For example, a full HMM may include N×N×2 (e.g., 100×100× 2) possible states in a window. Comparably, in the first stage the computing server may determine that only 10 ethnicity labels are relevant to this particular individual. The determination of relevant candidate ethnicity labels is specific to a particular individual and changes based on different individuals' genetic data. The simplified inter-window HMM may include only 10×10×2 possible states in a window, which results in a 100-fold reduction in complexity for the numbers given in this example. In other cases, the number of possible states may be 11×11×2, 9×9×2, 14×14×2, etc. In any cases, for a vast majority of target individuals, the complexity of the diploid, phased-accounted inter-window HMM is vastly reduced. In some embodiments, the inter-window HMM in the second stage may be diploid but not phased accounted (e.g., switch label is not used). In other embodiments, the inter-window HMM in the second stage may be diploid and phased accounted. Whether switching labels are used may depend on the accuracy of phasing algorithms.

Using the diploid inter-window HMM in the second stage, the Viterbi path corresponding to the target individual may be determined and the ordered set labels each for the first parent and the second parent are determined. In some embodiments, the ethnicity labels for both parents may be combined to provide an overall estimate of the genotype compositions of the target individual. In some embodiments, because the two parent sets are accounted for, the genetic compositions for the target individual may be separately reported for each parent. In some embodiments, whether a particular parent is the father or the mother may be further determined based on genealogy data (e.g., knowing that one parent is Asian based on genealogy data), by further analyzing the genetic data of the parents, or by another suitable process.

Example System Environment

FIG. 1 illustrates a diagram of a system environment 100 of an example computing server 130, in accordance with some embodiments. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more computing devices capable of receiving user input as well as transmitting and/or receiving data via a network 120. Example computing devices include desktop computers, laptop computers, personal digital assistants (PDAs), smartphones, tablets, wearable electronic devices (e.g., smartwatches), smart household appliances (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. In some embodiments, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more subnetworks, which may include any combination of local area and/or wide area networks, using both wired and/or wireless communication systems. In some embodiments, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet switching networks such as the Internet.

Individuals, who may be customers of a company operating the computing server 130, provide biological samples for analysis of their genetic data. Individuals may also be referred to as users. In some embodiments, an individual uses a sample collection kit to provide a biological sample (e.g., saliva, blood, hair, tissue) from which genetic data is extracted and determined according to nucleotide processing techniques such as amplification and sequencing. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. In some embodiments, a set of SNPs (e.g., 300,000) that are shared between different array platforms (e.g., Illumina OmniExpress Platform and Illumina HumanHap 650Y Platform) may be obtained as genetic data. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from coding and/or noncoding regions of DNA.

The genetic data may take different forms and include information regarding various biomarkers of an individual. For example, in some embodiments, the genetic data may be the base pair sequence of an individual. The base pair sequence may include the whole genome or a part of the genome such as certain genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. A SNP site may also be referred to as a SNP loci. A genetic locus is a segment of a genetic sequence. A locus can be a single site or a longer stretch. The segment can be a single base long or multiple bases long. In some embodiments, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual. SNPs, base pair sequence, genotype, haplotype, RNA sequences, protein sequences, and phenotypes are examples of biomarkers. In some embodiments, each SNP site may have two readings that are heterozygous.

The computing server 130 performs various analyses of the genetic data, genealogy data, and users' survey responses to generate results regarding the phenotypes and genealogy of users of computing server 130. Depending on the embodiments, the computing server 130 may also be referred to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnicity compositions of users, paternal and maternal genetic analysis, identification or suggestion of potential family relatives, ancestor information, analyses of DNA data, potential or identified traits such as phenotypes of users (e.g., diseases, appearance traits, other genetic characteristics, and other non-genetic characteristics including social characteristics), etc. The computing server 130 may present or cause the user interface 115 to present the results to the users through a GUI displayed at the client device 110. The results may include graphical elements, textual information, data, charts, and other elements such as family trees.

In some embodiments, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a pedigree chart. In some embodiments, subject to user's privacy setting and authorization, the computing server 130 may allow information generated from the user's genetic dataset to be linked to the user profile and to one or more of the family trees. The users may also authorize the computing server 130 to analyze their genetic dataset and allow their profiles to be discovered by other users.

Example Computing Server Architecture

Figure 2A:
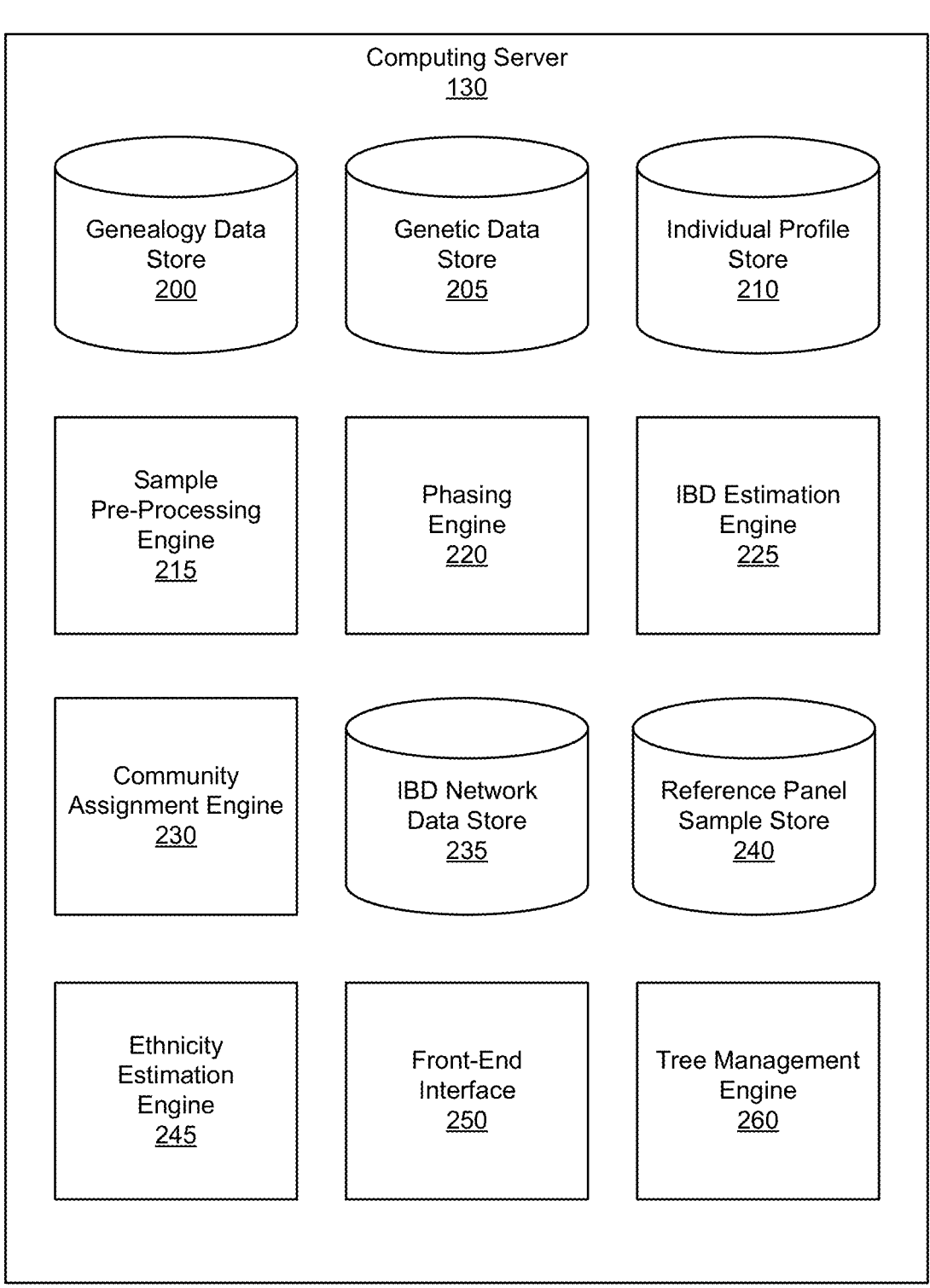
FIG. 2A is a block diagram of an architecture of an example computing system, in accordance with some embodiments, in accordance with some embodiments.

FIG. 2 is a block diagram of an architecture of an example computing server 130, in accordance with some embodiments. In the embodiment shown in FIG. 2, the computing server 130 includes a genealogy data store 200, a genetic data store 205, an individual profile store 210, a sample pre-processing engine 215, a phasing engine 220, an identity by descent (IBD) estimation engine 225, a community assignment engine 230, an IBD network data store 235, a reference panel sample store 240, an ethnicity estimation engine 245, a front-end interface 250, and a tree management engine 260. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogy data, and survey response data. The computing server 130 processes the genetic data of users to identify shared identity-by-descent (IBD) segments between individuals. The genealogy data and survey response data may be part of user profile data. The amount and type of user profile data stored for each user may vary based on the information of a user, which is provided by the user as she creates an account and profile at a system operated by the computing server 130 and continues to build her profile, family tree, and social network at the system and to link her profile with her genetic data. Users may provide data via the user interface 115 of a client device 110. Initially and as a user continues to build her genealogical profile, the user may be prompted to answer questions related to the basic information of the user (e.g., name, date of birth, birthplace, etc.) and later on more advanced questions that may be useful for obtaining additional genealogy data. The computing server 130 may also include survey questions regarding various traits of the users such as the users' phenotypes, characteristics, preferences, habits, lifestyle, environment, etc.

Genealogy data may be stored in the genealogy data store 200 and may include various types of data that are related to tracing family relatives of users. Examples of genealogy data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of an individual (e.g., the recorded relationships in the family). The family tree information associated with an individual may include one or more specified nodes. Each node in the family tree represents the individual, an ancestor of the individual who might have passed down genetic material to the individual, and the individual's other relatives including siblings, cousins, and offspring in some cases. Genealogy data may also include connections and relationships among users of the computing server 130. The information related to the connections among a user and her relatives that may be associated with a family tree may also be referred to as pedigree data or family tree data.

In addition to user-input data, genealogy data may also take other forms that are obtained from various sources such as public records and third-party data collectors. For example, genealogical records from public sources include birth records, marriage records, death records, census records, court records, probate records, adoption records, obituary records, etc. Likewise, genealogy data may include data from one or more family trees of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Furthermore, the genealogy data store 200 may also include relationship information inferred from the genetic data stored in the genetic data store 205 and information received from the individuals. For example, the relationship information may indicate which individuals are genetically related, how they are related, how many generations back they share common ancestors, lengths and locations of IBD segments shared, which genetic communities an individual is a part of, variants carried by the individual, and the like.

The computing server 130 maintains genetic datasets of individuals in the genetic data store 205. A genetic dataset of an individual may be a digital dataset of nucleotide data (e.g., SNP data) and corresponding metadata. A genetic dataset may contain data on the whole or portions of an individual's genome. The genetic data store 205 may store a pointer to a location associated with the genealogy data store 200 associated with the individual. A genetic dataset may take different forms. In some embodiments, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP sites (e.g., allele sites) filtered from the sequencing results. A SNP site that is single base pair long may also be referred to a SNP locus. A SNP site may be associated with a unique identifier. The genetic dataset may be in a form of diploid data that includes a sequencing of genotypes, such as genotypes at the target SNP site, or the whole base pair sequence that includes genotypes at known SNP site and other base pair sites that are not commonly associated with known SNPs. The diploid dataset may be referred to as a genotype dataset or a genotype sequence. Genotype may have a different meaning in various contexts. In one context, an individual's genotype may refer to a collection of diploid alleles of an individual. In other contexts, a genotype may be a pair of alleles present on two chromosomes for an individual at a given genetic marker such as a SNP site.

Genotype data for a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences. Similar to genotype, haplotype may have a different meaning in various contexts. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The individual profile store 210 stores profiles and related metadata associated with various individuals appeared in the computing server 130. A computing server 130 may use unique individual identifiers to identify various users and other non-users that might appear in other data sources such as ancestors or historical persons who appear in any family tree or genealogy database. A unique individual identifier may be a hash of certain identification information of an individual, such as a user's account name, user's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointers associating genetic datasets such as genotype and phased haplotype data of the individual that are saved in the genetic data store 205. The metadata about the individual may also be individual information related to family trees and pedigree datasets that include the individual. The profile data may further include declarative information about the user that was authorized by the user to be shared and may also include information inferred by the computing server 130. Other examples of information stored in a user profile may include biographic, demographic, and other types of descriptive information such as work experience, educational history, gender, hobbies, or preferences, location and the like. In some embodiments, the user profile data may also include one or more photos of the users and photos of relatives (e.g., ancestors) of the users that are uploaded by the users. A user may authorize the computing server 130 to analyze one or more photos to extract information, such as the user's or relative's appearance traits (e.g., blue eyes, curved hair, etc.), from the photos. The appearance traits and other information extracted from the photos may also be saved in the profile store. In some cases, the computing server may allow users to upload many different photos of the users, their relatives, and even friends. User profile data may also be obtained from other suitable sources, including historical records (e.g., records related to an ancestor), medical records, military records, photographs, other records indicating one or more traits, and other suitable recorded data.

For example, the computing server 130 may present various survey questions to its users from time to time. The responses to the survey questions may be stored at individual profile store 210. The survey questions may be related to various aspects of the users and the users' families. Some survey questions may be related to users' phenotypes, while other questions may be related to environmental factors of the users.

Survey questions may concern health or disease-related phenotypes, such as questions related to the presence or absence of genetic diseases or disorders, inheritable diseases or disorders, or other common diseases or disorders that have a family history as one of the risk factors, questions regarding any diagnosis of increased risk of any diseases or disorders, and questions concerning wellness-related issues such as a family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's disease, diabetes, cancer, and obesity. The computing server 130 may obtain data on a user's disease-related phenotypes from survey questions about the health history of the user and her family and also from health records uploaded by the user.

Survey questions also may be related to other types of phenotypes such as appearance traits of the users. A survey regarding appearance traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding other traits also may include questions related to users' taste and smell such as the ability to taste bitterness, asparagus smell, cilantro aversion, etc. A survey regarding traits may further include questions related to users' body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as the ability to sense an asparagus metabolite. Traits may also be collected from historical records, electronic health records and electronic medical records.

The computing server 130 also may present various survey questions related to the environmental factors of users. In this context, an environmental factor may be a factor that is not directly connected to the genetics of the users. Environmental factors may include users' preferences, habits, and lifestyles. For example, a survey regarding users' preferences may include questions related to things and activities that users like or dislike, such as types of music a user enjoys, dancing preference, party-going preference, certain sports that a user plays, video game preferences, etc. Other questions may be related to the users' diet preferences such as like or dislike a certain type of food (e.g., ice cream, egg). A survey related to habits and lifestyle may include questions regarding smoking habits, alcohol consumption and frequency, daily exercise duration, sleeping habits (e.g., morning person versus night person), sleeping cycles and problems, hobbies, and travel preferences. Additional environmental factors may include diet amount (calories, macronutrients), physical fitness abilities (e.g., stretching, flexibility, heart rate recovery), family type (adopted family or not, has siblings or not, lived with extended family during childhood), property and item ownership (has home or rents, has a smartphone or doesn't, has a car or doesn't).

Surveys also may be related to other environmental factors such as geographical, social-economic, or cultural factors. Geographical questions may include questions related to the birth location, family migration history, town, or city of users' current or past residence. Social-economic questions may be related to users' education level, income, occupations, self-identified demographic groups, etc. Questions related to culture may concern users' native language, language spoken at home, customs, dietary practices, etc. Other questions related to users' cultural and behavioral questions are also possible.

For any survey questions asked, the computing server 130 may also ask an individual the same or similar questions regarding the traits and environmental factors of the ancestors, family members, other relatives or friends of the individual. For example, a user may be asked about the native language of the user and the native languages of the user's parents and grandparents. A user may also be asked about the health history of his or her family members.

In addition to storing the survey data in the individual profile store 210, the computing server 130 may store some responses that correspond to data related to genealogical and genetics respectively to genealogy data store 200 and genetic data store 205.

The user profile data, photos of users, survey response data, the genetic data, and the genealogy data may be subject to the privacy and authorization setting of the users to specify any data related to the users that can be accessed, stored, obtained, or otherwise used. For example, when presented with a survey question, a user may select to answer or skip the question. The computing server 130 may present users from time to time information regarding users' selection of the extent of information and data shared. The computing server 130 also may maintain and enforce one or more privacy settings for users in connection with the access of the user profile data, photos, genetic data, and other sensitive data. For example, the user may pre-authorize the access to the data and may change the setting as wished. The privacy settings also may allow a user to specify (e.g., by opting out, by not opting in) whether the computing server 130 may receive, collect, log, or store particular data associated with the user for any purpose. A user may restrict her data at various levels. For example, on one level, the data may not be accessed by the computing server 130 for purposes other than displaying the data in the user's own profile. On another level, the user may authorize anonymization of her data and participate in studies and research conducted by the computing server 130 such as a large-scale genetic study. On yet another level, the user may turn some portions of her genealogy data public to allow the user to be discovered by other users (e.g., potential relatives) and be connected to one or more family trees. Access or sharing of any information or data in the computing server 130 may also be subject to one or more similar privacy policies. A user's data and content objects in the computing server 130 may also be associated with different levels of restriction.

The computing server 130 may also provide various notification features to inform and remind users of their privacy and access settings. For example, when privacy settings for a data entry allow a particular user or other entities to access the data, the data may be described as being "visible," "public," or other suitable labels, contrary to a "private" label.

In some cases, the computing server 130 may have a heightened privacy protection on certain types of data and data related to certain vulnerable groups. In some cases, the heightened privacy settings may strictly prohibit the use, analysis, and sharing of data related to a certain vulnerable group. In other cases, the heightened privacy settings may specify that data subject to those settings require prior approval for access, publication, or other use. In some cases, the computing server 130 may provide the heightened privacy as a default setting for certain types of data, such as genetic data or any data that the user marks as sensitive. The user may opt in to sharing of those data or change the default privacy settings. In other cases, the heightened privacy settings may apply across the board for all data of certain groups of users. For example, if computing server 130 determines that the user is a minor or has recognized that a picture of a minor is uploaded, the computing server 130 may designate all profile data associated with the minor as sensitive. In those cases, the computing server 130 may have one or more extra steps in seeking and confirming any sharing or use of the sensitive data.

The sample pre-processing engine 215 receives and pre-processes data received from various sources to change the data into a format used by the computing server 130. For genealogy data, the sample pre-processing engine 215 may receive data from an individual via the user interface 115 of the client device 110. To collect the user data (e.g., genealogical and survey data), the computing server 130 may cause an interactive user interface on the client device 110 to display interface elements in which users can provide genealogy data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's genetic dataset. In some embodiments, the SNPs may be autosomal SNPs. In some embodiments, 700,000 SNPs may be identified in an individual's data and may be stored in genetic data store 205. Alternatively, in some embodiments, a genetic dataset may include at least 10,000 SNP sites. In another embodiment, a genetic dataset may include at least 100,000 SNP sites. In yet another embodiment, a genetic dataset may include at least 300,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases diploid genetic dataset into a pair of haploid genetic datasets and may perform imputation of SNP values at certain sites whose alleles are missing. An individual's haplotype may refer to a collection of alleles (e.g., a sequence of alleles) that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP locus of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's genetic datasets. The haplotype-cluster model may be generated iteratively along with the phasing process with a large number of unphased genotype datasets. The haplotype-cluster model may also be used to impute one or more missing data.

By way of example, the phasing engine 220 may use a directed acyclic graph model such as a hidden Markov model (HMM) to perform the phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. Pat. No.

10,679,729, entitled "Haplotype Phasing Models," granted on Jun. 9, 2700, describes example embodiments of haplotype phasing.

A phasing algorithm may also generate phasing result that has a long-distance accuracy in terms of haplotype separation. For example, in some embodiments, a jig phasing algorithm may be used, which is described in further detail in U.S. Patent Application Publication No. US 2701/0034647, entitled "Clustering of Matched Segments to Determine Linkage of Dataset in a Database," published on Feb. 4, 2701. For example, the computing server 130 may receive a target individual genotype dataset and a plurality of additional individual genotype datasets that include haplotypes of additional individuals. For example, the additional individuals may be reference panels or individuals who are linked (e.g., in a family tree) to the target individual. The computing server 130 may generate a plurality of sub-cluster pairs of first parental groups and second parental groups. Each sub-cluster pair may be in a window. The window may correspond to a genomic segment and has a similar concept of window used in the ethnicity estimation engine 245 and the rest of the disclosure related to HMMs, but how windows are precisely divided and defined may be the same or different in the phasing engine 220 and in an HMM. Each sub-cluster pair may correspond to a genetic locus. In some embodiments, each sub-cluster pair may have a first parental group that includes a first set of matched haplotype segments selected from the plurality of additional individual datasets and a second parental group that includes a second set of matched haplotype segments selected from the plurality of additional individual datasets. The computing server 130 may generate a super-cluster of a parental side by linking the first parental groups and the second parental groups across a plurality of genetic loci (across a plurality of sub-cluster pairs). Generating the super-cluster of the parental side may include generating a candidate parental side assignment of parental groups across a set of sub-cluster pairs that represent a set of genetic loci in the plurality of genetic loci. The computing server 130 may determine a number of common additional individual genotype datasets that are classified in the candidate parental side assignment. The computing server 130 may determine the candidate parental side assignment to be part of the super-cluster based on the number of common additional individual genotype datasets. Any suitable algorithms may be used to generate the super-cluster, such as a heuristic scoring approach, a bipartite graph approach, or another suitable approach. The computing server 130 may generate a haplotype phasing of the target individual from the super-cluster of the parental side. Detail of this phasing approach is further discussed in FIG. 3C through FIG. 3G.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicates the mismatch is not attributable to potential errors in phasing or imputation. The IBD estimation engine 225 determines the total length of matched segments, which may also be referred to as IBD segments. The length may be measured in the genetic distance in the unit of centimorgans (cM). A unit of centimorgan may be a genetic length. For example, two genomic positions that are one cM apart may have a 1% chance during each meiosis of experiencing a recombination event between the two positions. The computing server 130 may save data regarding individual pairs who share a length of IBD segments exceeding a predetermined threshold (e.g., 6 cM), in a suitable data store such as in the genealogy data store 200. U.S. Pat. No. 10,114,922, entitled "Identifying Ancestral Relationships Using a Continuous stream of Input," granted on Oct. 30, 2018, and U.S. Pat. No. 10,720, 229, entitled "Reducing Error in Predicted Genetic Relationships," granted on Jul. 21, 2700, describe example embodiments of IBD estimation.

Typically, individuals who are closely related share a relatively large number of IBD segments, and the IBD segments tend to have longer lengths (individually or in aggregate across one or more chromosomes). In contrast, individuals who are more distantly related share relatively fewer IBD segments, and these segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments shared between two individuals.

Community assignment engine 230 assigns individuals to one or more genetic communities based on the genetic data of the individuals. A genetic community may correspond to an ethnic origin or a group of people descended from a common ancestor. The granularity of genetic community classification may vary depending on embodiments and methods used to assign communities. For example, in some embodiments, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., the Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. Pat. No. 10,223,498, entitled "Discovering Population Structure from Patterns of Identity-By-Descent," granted on Mar. 5, 2019, describes example embodiments of community detection and assignment.

The community assignment engine 230 may also assign communities using supervised techniques. For example, genetic datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. A reference panel sample is a genetic data of an individual whose genetic data is the most representative of a genetic community. The genetic data of individuals with the typical alleles of a genetic community may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belongs to a community, determining the ethnic composition of an individual, and determining the accuracy of any genetic data analysis, such as by computing a posterior probability of a classification result from a classifier.

A reference panel sample may be identified in different ways. In some embodiments, an unsupervised approach in community detection may apply the clustering algorithm recursively for each identified cluster until the sub-clusters contain a number of nodes that are smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of the times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected. For example, a candidate reference panel sample may be selected from an individual whose recent ancestors are born at a certain birthplace. The computing server 130 may also draw sequence data from the Human Genome Diversity Project (HGDP). Various candidates may be manually screened based on their family trees, relatives' birth location, and other quality control. Principal component analysis may be used to create clusters of genetic data of the candidates. Each cluster may represent an ethnicity. The predictions of the ethnicity of those candidates may be compared to the ethnicity information provided by the candidates to perform further screening.

The ethnicity estimation engine 245 estimates the ethnicity composition of a genetic dataset of a target individual. The genetic datasets used by the ethnicity estimation engine 245 may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In some embodiments, the ethnicity estimation engine 245 divides a target genetic dataset into a plurality of windows (e.g., about 1000 windows). Each window includes a small number of SNPs (e.g., 300 SNPs). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of node groups. Each node group, representing a window, includes a plurality of nodes. The nodes represent different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNPs belongs to a second ethnicity. Each level includes multiple nodes so that there are many possible paths to traverse the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNPs in the window. The ethnicity estimation engine 245 determines the emission probabilities by comparing SNPs in the window corresponding to the target genetic dataset to corresponding SNPs in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. Pat. No. 10,558,930, entitled "Local Genetic Ethnicity Determination System," granted on Feb. 11, 2700 and U.S. Pat. No. 10,692,587, granted on Jun. 23, 2700, entitled "Global Ancestry Determination System" describe different example embodiments of ethnicity estimation. Further detail of an example ethnicity estimation engine 245 that uses a two-stage pipeline to speed up label assignment is discussed below in FIGS. 4A and 4B.

The front-end interface 250 displays various results determined by the computing server 130. The results and data may include the IBD affinity between a user and another individual, the community assignment of the user, the ethnicity estimation of the user, phenotype prediction and evaluation, genealogy data search, family tree and pedigree, relative profile and other information. The front-end interface 250 may allow users to manage their profile and data trees (e.g., family trees). The users may view various public family trees stored in the computing server 130 and search for individuals and their genealogy data via the front-end interface 250. The computing server 130 may suggest or allow the user to manually review and select potentially related individuals (e.g., relatives, ancestors, close family members) to add to the user's data tree. The front-end interface 250 may be a graphical user interface (GUI) that displays various information and graphical elements. The front-end interface 250 may take different forms. In one case, the front-end interface 250 may be a software application that can be displayed on an electronic device such as a computer or a smartphone. The software application may be developed by the entity controlling the computing server 130 and be downloaded and installed on the client device 110. In another case, the front-end interface 250 may take the form of a webpage interface of the computing server 130 that allows users to access their family tree and genetic analysis results through web browsers. In yet another case, the front-end interface 250 may provide an application program interface (API).

The tree management engine 260 performs computations and other processes related to users' management of their data trees such as family trees. The tree management engine 260 may allow a user to build a data tree from scratch or to link the user to existing data trees. In some embodiments, the tree management engine 260 may suggest a connection between a target individual and a family tree that exists in the family tree database by identifying potential family trees for the target individual and identifying one or more most probable positions in a potential family tree. A user (target individual) may wish to identify family trees to which he or she may potentially belong. Linking a user to a family tree or building a family may be performed automatically, manually, or using techniques with a combination of both. In an embodiment of an automatic tree matching, the tree management engine 260 may receive a genetic dataset from the target individual as input and search related individuals that are IBD-related to the target individual. The tree management engine 260 may identify common ancestors. Each common ancestor may be common to the target individual and one of the related individuals. The tree management engine 260 may in turn output potential family trees to which the target individual may belong by retrieving family trees that include a common ancestor and an individual who is IBD-related to the target individual. The tree management engine 260 may further identify one or more probable positions in one of the potential family trees based on information associated with matched genetic data between the target individual and those in the potential family trees through one or more machine learning models or other heuristic algorithms. For example, the tree management engine 260 may try putting the target individual in various possible locations in the family tree and determine the highest probability position(s) based on the genetic dataset of the target individual and genetic datasets available for others in the family tree and based on genealogy data available to the tree management engine 260. The tree management engine 260 may provide one or more family trees from which the target individual may select. For a suggested family tree, the tree management engine 260 may also provide information on how the target individual is related to other individuals in the tree. In a manual tree building, a user may browse through public family trees and public individual entries in the genealogy data store 200 and individual profile store 210 to look for potential relatives that can be added to the user's family tree. The tree management engine 260 may automatically search, rank, and suggest individuals for the user conduct manual reviews as the user makes progress in the front-end interface 250 in building the family tree.

As used herein, "pedigree" and "family tree" may be interchangeable and may refer to a family tree chart or pedigree chart that shows, diagrammatically, family information, such as family history information, including parentage, offspring, spouses, siblings, or otherwise for any suitable number of generations and/or people, and/or data pertaining to persons represented in the chart. U.S. Pat. No. 11,429,615, entitled "Linking Individual Datasets to a Database," granted on Aug. 30, 2022, describes example embodiments of how an individual may be linked to existing family trees.

Example Label Determination System

Figure 2B:
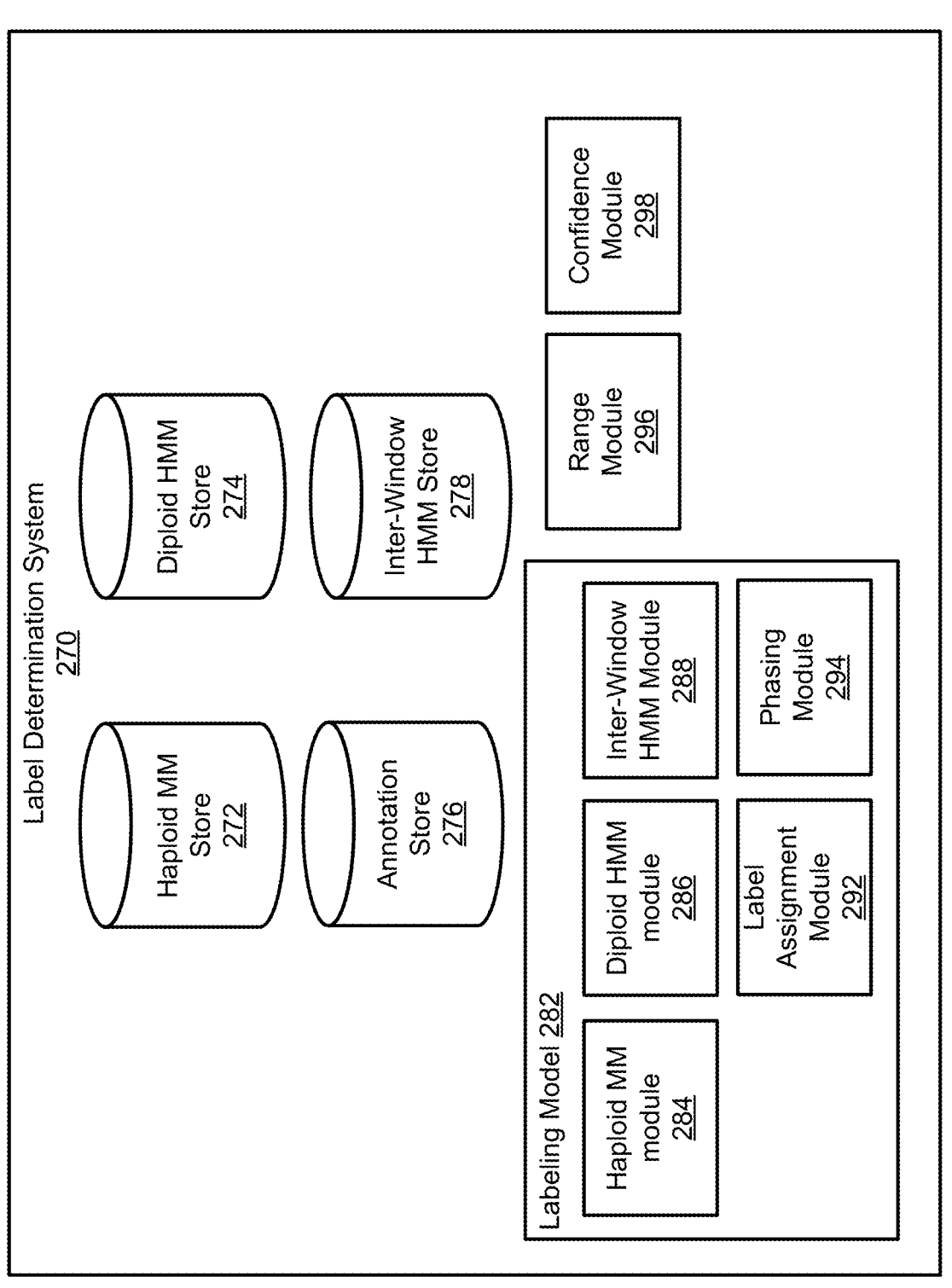
FIG. 2B is a block diagram of an architecture of an example label determination system, in accordance with some embodiments.

FIG. 2B is a block diagram of a label determination system 270 for training and utilizing a model to assign labels to a genetic dataset, according to some embodiments. The label determination system 270 (or some components of the label determination system 270) may be an example of the ethnicity estimation engine 245. The label determination system 270 trains and uses models to probabilistically determine the labels to which an input genotype sample corresponds. The label determination system 270 may be a computing system including one or more processors, one or more computer memories, and an interface for communicating through a network. In one example embodiment, the label determination system 270 includes a haploid Markov model (MM) store 272, a diploid HMM store 274, an annotation store 276, an inter-window HMM store 278, a range module 296, and a confidence module 298. The label determination system 270 can build and train a labeling model 282. The labeling model 282 includes various components (which may also be referred to as sub-models or modules) such as a haploid MM module 284, a diploid HMM module 286, an inter-window HMM module 288, a label assignment module 292, and a phasing module 294. In various embodiments, the labeling model 282 may include additional or fewer modules.

Genetic data store 205 maintains genetic datasets of individuals. Genetic data may contain whole or portions of individual's genome and corresponding metadata. The data stored in the genetic data store 205 may store one or more genetic datasets linked to a user. In various embodiments, the genetic data store 205 stores a pointer to a location associated with the genealogy data store 200 associated with the individual. A genetic dataset may take different forms. In one embodiment, a genetic dataset may take the form of base pair sequence of the DNA sequence of an individual. A genetic dataset may include a whole genome of the individual (e.g., obtained from a whole-genome sequencing) or some parts of genetic loci. In another embodiment, a genetic dataset may take the form of sequences of target SNP sites and allele sites. The genetic dataset may be in the form of a diploid data and may be phased into two sets of haploid data. The diploid data may also be referred to as genotype data while the phased haploid data may be referred to as haplotype data.

In some embodiments, the label determination system 270 may operate in a training stage and a label assignment stage. The training stage may be performed once to train the labeling model 282 that includes sub-models. For example, a haploid MM for each window w stored in the haploid MM store 272 may be trained to calculate the annotations stored in the annotation store 276 for each label k and window w. The training stage is often based on more than a single particular input sample genotype dataset. For example, a collection of training samples may be used. A particular training sample may be assigned with known labels in different windows of the training sample. The assigned labels may serve as ground truth for training. The label determination system 270 may adjust the parameters of the models used (e.g., the transition probabilities in an HMM) so that the models reduce the prediction errors in label assignments when compared to the ground truth of the labels. Multiple iterations of training may be performed until the parameter converge.

After the training stage, the label determination system 270 may assign labels to an input sample genotype dataset X during the label assignment stage. Assigning labels to the sample genotype dataset X uses the haploid MMs and the annotations initialized during the training phase. In some embodiments, after the training stage for the labeling model 282 has been performed once, labels may be continuously assigned to different input genotype datasets. In other embodiments, after the labeling model 282 is initially trained, the label determination system 270 may continuously improve and update various components of the labeling model 282 by treating previously labeled input genotype datasets that were themselves labeled by the labeling model 282 as additional training samples.

The phasing module 294 phases diploid genetic dataset into a pair of haploid genetic datasets and may be an example of the phasing engine 220. An individual's haplotype may refer to a collection of alleles (e.g., a sequence of alleles) that are inherited from a parent. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The phasing module 294 may probabilistically separate the input sample genotype X into its constituent haplotypes based on the assigned labels. In one embodiment, a pair of labels for each window w is assigned based on the Viterbi path through the inter-window HMM. Phasing (i.e., separating the input sample genotype X into haplotypes) may be performed based on diploid HMMs 302 for each window w modified by the annotations $A_w$ for the assigned labels. For example, the diploid HMM for the input sample genotype X may be modified so that the probability of the diploid state $(u_1, u_2)$ in the window w is given by $A_w(u_1, p) \times A_w(u_2, q)$. The SNPs in the window w may be phased into the constituent haplotypes by determining the Viterbi path through the modified diploid HMM. In this way, the genome X may be phased so as to maximize the agreement with the label assignment. The haplotypes may also be combined across windows. For example, if the labels (p,q) were assigned to window w and the labels (p,q') were assigned to window w+1, then the sequence of alleles in the phased haplotype corresponding to label p in window w may be combined with the sequence of alleles in the phased haplotype corresponding to label p in window w+1. Similarly, the sequence of alleles in the phased haplotype corresponding to label q in window w may be combined with those of label q' in window w+1.

Figure 3A:
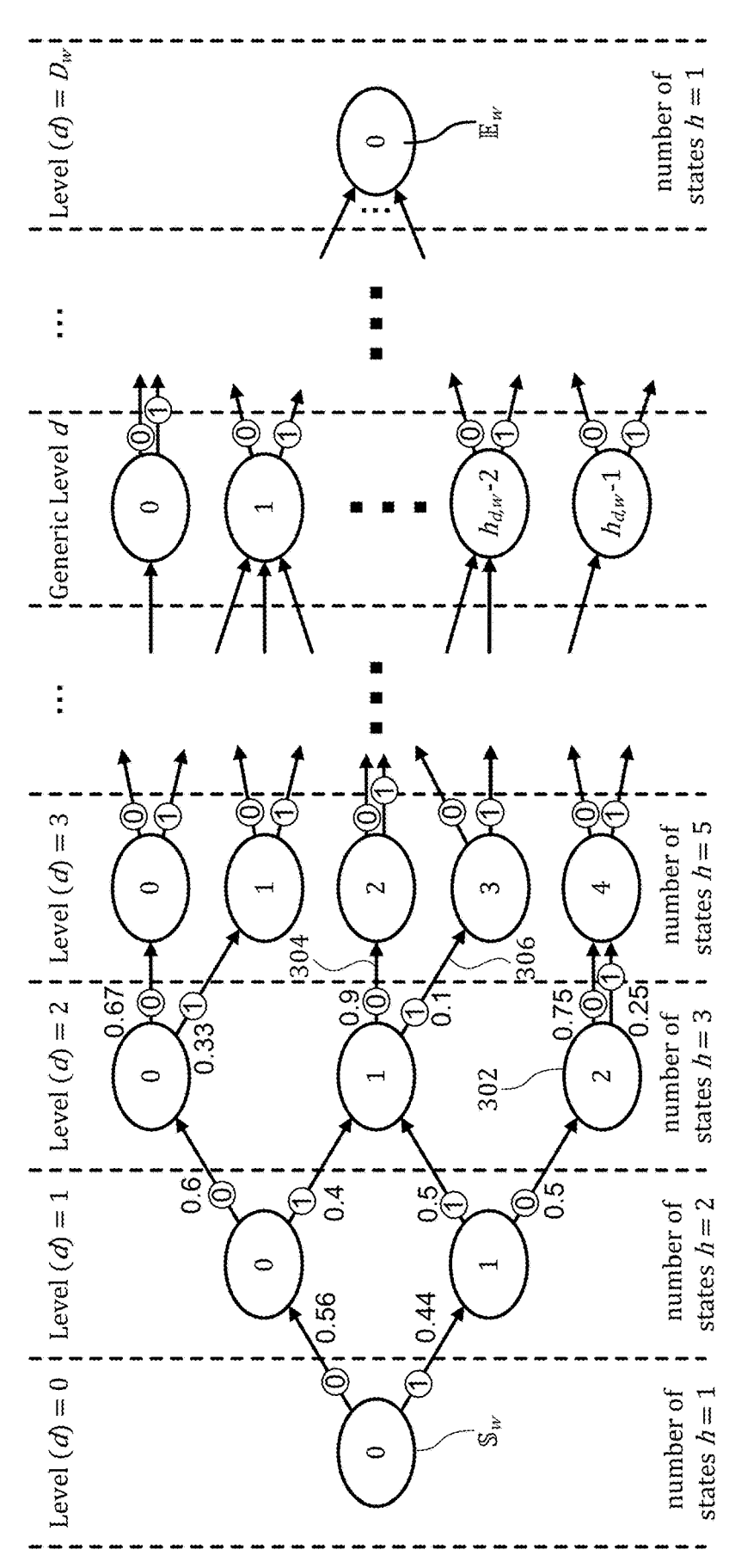
FIG. 3A is a diagram illustrating relationships between nodes in a window of a haploid Markov model, in accordance with some embodiments.

FIG. 3A illustrates an example of a haploid single-window MM 301 for a window w, according to some embodiments. This single-window MM 301 is not to be confused with the haploid full-ethnicity inter-window HMM 400 described in FIG. 4A. The entire MM 301 corresponds to a single window of the inter-window HMM 400. FIG. 3A illustrates the haploid MM for window w as a directed graph, where circles represent nodes with each node corresponding to a state, and arrows represent edges with each edge corresponding to a transition between a first state in a d–1th level to a second state in a d-th level. Each node in the diploid HMM 302 may represent a single SNP site. The haploid MM is divided into $D_w+1$ levels (i.e., the haploid MM includes one more level than the number $D_w$ of SNPs in the window w). Each state in the model corresponds to some level $d \in \{0, \ldots, D_w+1\}$. Each level d in the window w includes h states. Each state u in the haploid MM may be referenced by the combination of its level d and an index n (for $n \in \{0, \ldots, h-1\}$), although states may be references with an alternate referencing scheme. In FIG. 3A, the index n of each state u is the integer with which the state is labeled. Herein, u(w,d,n) references the nth state at level d in window w. Thus, the start state is $\mathbb{S}_w=u(w,0,0)$, state 303 is u(w,3,3), and the end state is $\mathbb{E}_w=u(w,D_w,0)$.

A haploid MM 301 includes one start state $\mathbb{S}_w$ at level 0 and one end state $\mathbb{E}_w$ at level D. Besides the end state $\mathbb{E}_w$ at level $D_w$ which is a terminal node, each state at level d can include outgoing transitions to either one or two states at level d+1. The transition between a state at level d–1 to a second state in level d corresponds to the dth allele in window w of a haplotype. In FIG. 3A, the allele value of a haplotype corresponding to the transition between two states is illustrated by the number (either 0 or 1) on the arrow between the states. For example, the transition from the start state SSW to u(w,1,0) (i.e., the state at level 1 with index number n=0) corresponds to an allele of 0 at the first SNP position in window w and the transition from the start state $\mathbb{S}_w$ to u(w,1,1) (i.e., the state at level 1 with index number n=1) may correspond to an allele of 1 at that SNP position. As indicated by FIG. 3A, in this example, the transition probability between the start state SSW and u(w,1,0) is 0.56 and the transition probability between $\mathbb{S}_w$ and u(w,1,1) is 1–0.56=0.44.

In the haploid MM 301, the transition function t(u,a) describes the transition of a haploid state u in a d–1th level to an allele value a in the d-th level, where the allele value a may take a binary value (e.g., $a \in \{0,1\}$). For example, in FIG. 3A, t(u(w,3,0),0) describes the transition from u(w,3,0) to u(w,3,0) because u(w,3,0) is the next state that has the allele value 0. Likewise, t(u(w,3,0),1) describes the transition to haploid state u(w,3,1) because u(w,3,1) is the next state that has the allele value 1. When a haploid state u at level d–1 transitions to two distinct states (i.e., when t(u,0) ≠t(u,1)), each of the transitions is mapped to the dth allele in the window w. Herein, $\rho(u,a)$ refers to the transition probability that state u at level d–1 transition to next state at the d-th SNP that has an allele that takes the value of a. For example, an edge 304, which represents u(w,3,1) transitioning to the next state that has an allele value of 0, corresponds to the transition probability $\rho(u(w,3,1),0)=0.9$. Likewise, an edge 306 corresponds to the transitional probability $\rho(u(w,3,1),1)=0.1$. If the state u transitions to only one state v at level d, then the haploid MM may still include a probability distribution for the d-th allele even though the state transition is deterministic. For example, as illustrated in FIG. 3A, the transition from state u(w,3,3) to state u(w,3,4) may associate a probability of 0.75 with allele 0 at the third SNP in the window w and a probability of 0.35 for allele 1 at the third SNP in the window w.

Each path through the haploid MM 301 corresponds to one or more possible sequences of alleles (for example, that may occur in the input sample genotype dataset X). The probability of a sequence of alleles is given by the product of the corresponding allele probabilities in the corresponding path. For example, a path that includes the sequence of state ($\mathbb{S}_w$, u(w,1,1), u(w,3,1), u(w,3,3)) corresponds to the sequence of alleles (1,1,1) which has a probability of $\rho(\mathbb{S}_w,1) \times \rho(u(w,1,1),1) \times \rho(u(w,3,1),1)=0.033$. The possible haplotypes (or, equivalently, every possible sequence of alleles) correspond to different paths in the haploid MM. Each path corresponding to a possible haplotype begins at the start state $\mathbb{S}_w$, includes exactly one state for each level d, and ends at the end state $\mathbb{E}_w$.

Figure 3B:
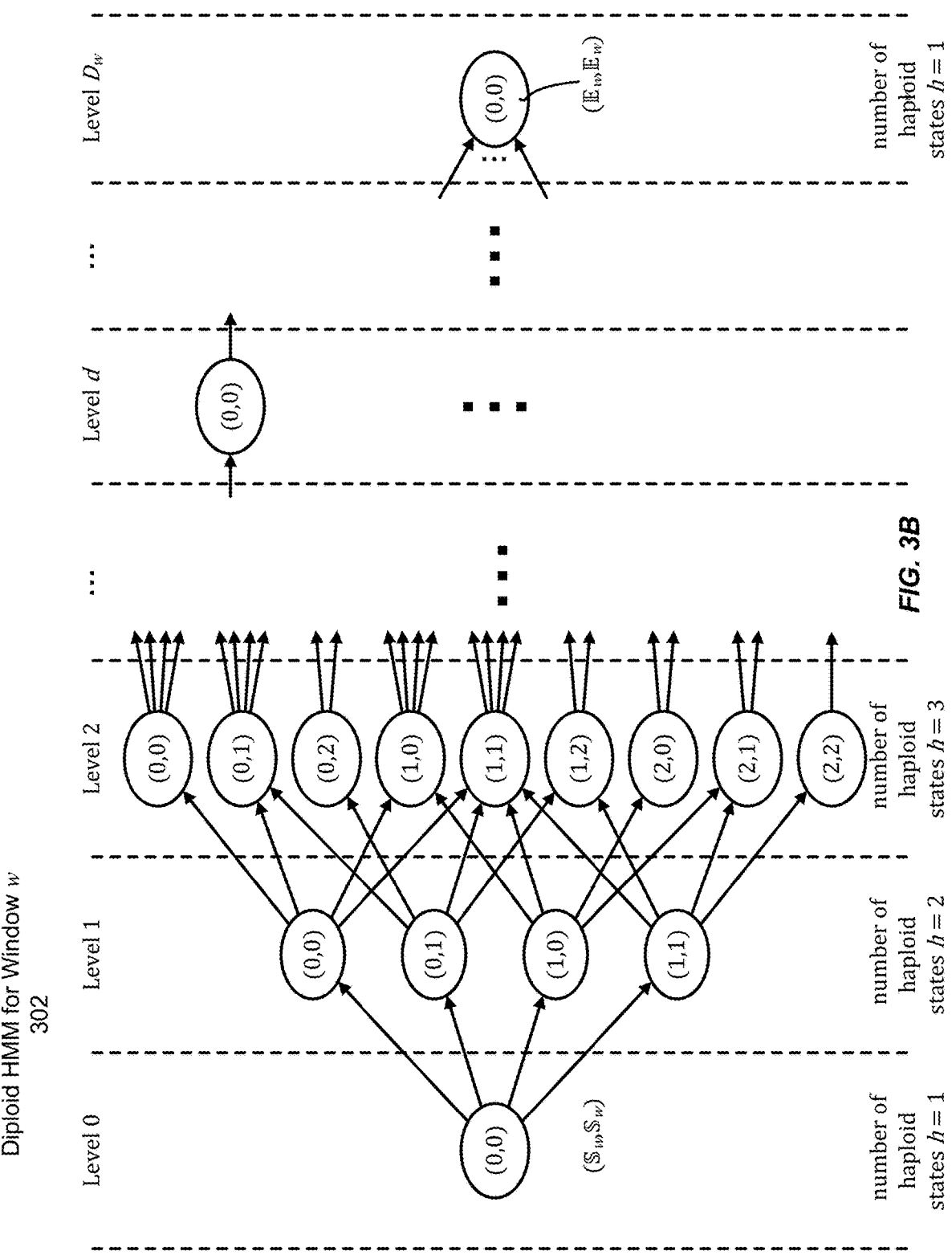
FIG. 3B is a diagram illustrating nodes illustrating relationships between nodes in a window of a diploid hidden Markov model, in accordance with some embodiments.

FIG. 3B is an example of a diploid single-window HMM 302 for a window w, according to some embodiments. This single-window MM 302 is not to be confused with the diploid inter-window HMM 410 described in FIG. 4B. The entire single-window HMM 302 corresponds to a single window of an inter-window HMM.

The diploid HMM illustrated in FIG. 3B is a fully-instantiated diploid HMM. For this reason, the number of diploid states at each level d for window w is equal to the square of the number of states in the corresponding haploid MM 301 at level d (i.e., $h^2$). For a genotype sequence made up of haplotypes that correspond to a diploid state $(u_1,u_2)$ at level d–1, the probability that the d-th alleles in the window w is the ordered pair $(a_1,a_2)$ equals $\rho(u_1,a_1) \times \rho(u_2,a_2)$. The number of possible transitions from a diploid state $(u_1,u_2)$ to another state is equal to the number of possible transitions from $u_1$ in the haploid MM to a next state multiplied by the number of possible transitions from $u_2$ to a next state.

FIG. 3B depicts an example diploid HMM 302 that corresponds to the example haploid MM 301 depicted in FIG. 3A. In FIG. 3B, each node represents a diploid state in the diploid HMM that is labeled with a pair of index numbers (n,m) corresponding to the indices of the corresponding pair of haploid states in the haploid MM 301. For example, the diploid state labeled (1,2) at level 2 in FIG. 3B represents the diploid state (u(w,2,1),u(w,2,2)) where haploid states u(w,2,1) and u(w,2,2) are from the haploid MM

301 of FIG. 3A. In some embodiments, the diploid states are phased so that the order of the two haploid states in a pair of diploid state represents the phase of the haploid states. For example, the diploid state labeled (1,2) represents that the first parent state is in the haploid state 1 while the second parent state is in the haploid state 2 while the diploid state labeled (2,1) represents that the first parent state is in the haploid state 2 while the second parent state is in the haploid state 1, or vice versa if the first state is denoted as the maternal state.

Because every genotype dataset corresponds to two haplotypes, each phased genotype dataset corresponds to a single path through the diploid HMM 302 for window w. However, because the SNPs in unphased genotype datasets do not associate alleles with particular haplotypes, the exact path through the diploid HMM that a genotype dataset traverses may be ambiguous as the genotype dataset will likely include a number of heterozygous SNPs and possibly missing data for SNPs as well. For example, the sequence of unordered allele pairs ((0,1),(0,1)) corresponds to four distinct paths through the first three levels of the example diploid HMM for window w such as the sequence of diploid states ( $\mathbb{S}_w$, $\mathbb{S}_w$),(u(w,1,0),u(w,1,1)),(u(w,2,1),u(w,2,2))). In addition, chromosome crossover may occur during meiosis. For various reasons, the phasing of a genotype dataset is not a deterministic process and, thus, there may be errors in phasing and determining a pair of haplotype sequence datasets from a genotype dataset.

The diploid HMM 302 may be used to generate a pair of phased haplotype datasets of an input genotype dataset for each window w. The input genotype dataset can be used with other training datasets to iteratively build the diploid HMM 302 for a predetermined number of iterations or until the diploid HMM 302 converges. For example, the diploid HMM 302 is initially trained with the reference panel samples obtained from the reference panel store 240. The reference panel samples may be unadmixed datasets or synthetic datasets for admixed populations. A different diploid HMM 302 may be computed and trained for each pair of labels using the reference panels associated with the pair of labels. The input genotype dataset may then be used as an input of the trained diploid HMM 302 to determine the Viterbi path of the diploid HMM 302. The Viterbi path may represent a likely outcome of a pair of phased haplotype datasets. The phased haplotype dataset may then be used as one of the training samples to improve the diploid HMM 302. This iteration may be repeated multiple times to improve the Viterbi path calculation and the phasing of the input genotype dataset. For more information on the phasing of an input genotype dataset to generate a pair of phased haplotype datasets, U.S. Patent Application Publication No. 2017/0262577 published Sep. 14, 2017, entitled "Haplotype Phasing Models," is incorporated by reference herein for all purposes. The diploid HMM 302 may also be used to determine label pair probability distributions and emission probabilities.

The diploid HMM 301 in FIG. 3A may represent an example of a phasing pipeline. FIG. 3C through FIG. 3G illustrate a jig phasing algorithm that represents another example of a phasing pipeline.

Example Jig Phasing Algorithm

FIGS. 3C, 3D, 3E, 3F, and 3G are conceptual diagrams explaining the pipeline of a jig phasing algorithm that produces a higher confidence of long distance phasing accuracy, in accordance with some embodiments.

In some embodiments, the computing server 130 may phase genotype dataset of a target individual to a first parental side (a first haplotype) and a second parental side (a first haplotype) of the target individual by comparing the genotype datasets of the individuals and of the target individual. Based on the classification, the computing server 130 may identify which of the first parental side or the second parental side is the paternal side or the maternal side. The computing server 130 may add metadata to datasets corresponding to individuals to identify the connection between the individuals and the target individual. In some embodiments, the process described may classify potential relatives to one of the parental sides without the DNA dataset of either parent of the target individual. In other words, in some embodiments, the DNA datasets of other individuals may be directly compared to the DNA dataset of the target individual in classifying whether those individuals belong to a first or second parental side.

By way of example, the computing server 130 may receive a target individual DNA dataset and additional individual DNA datasets, such as by retrieving the DNA datasets from a genetic data store 205. The DNA dataset of the target individual may be unphased genotype. The target individual DNA dataset may include data of a plurality of allele sites of interests such as SNP sites of interest. Some of the allele sites may be homozygous while others may be heterozygous. The computing server 130 also may identify a number of additional individuals who may be related to the target individuals by identity by descent (IBD). The computing server 130 may receive a plurality of DNA datasets of those individuals (referred to as additional individual DNA datasets, in contrast to the target individual DNA dataset).

By way of example, the computing server 130 may retrieve a target genotype sequence in the DNA dataset of the target individual. The target genotype sequence may be biallelic. The computing server 130 may also retrieve a plurality of genotype sequences of the DNA datasets of additional individuals. Each site in various sequences may be homozygous for major alleles, heterozygous, or homozygous for the minor allele, and in some cases can be missing—not called by the lab, not otherwise imputed by the computing server 130. In some cases, the major allele is whichever is more common in a population. In other cases, the designation of major or minor can be arbitrary. Any genotype sequence may be referred to as a DNA dataset.

After receiving the target individual DNA dataset, the computing server 130 may divide the target individual DNA dataset into a plurality of genetic loci. For a genetic locus, the computing server 130 may scan through different additional individual DNA datasets to see if there are DNA datasets that have a matched segment. The computing server 130 may set a predetermined number as a threshold for considering whether a segment is a match. For example, in order to qualify as a match, a DNA dataset may need to include a sequence of alleles at multiple consecutive SNP sites that overlap with some portion of the target individual DNA dataset at the genetic locus.

The computing server 130 may classify more than one additional individual DNA dataset that has a matched segment that overlaps the target individual DNA dataset at the genetic locus as matches to the target individual. Those classified DNA datasets collectively may be referred to a sub-cluster pair because the computing server 130 may further classify those classified DNA datasets to a first parental group and a second parental group (e.g., a pair of a first group of DNA datasets classified to the first parental side and a second group of DNA datasets classified to the second parental side). A sub-cluster pair of parental groups may simply be referred to as a sub-cluster. A parental group in a sub-cluster may be referred to as a sub-parent group, or simply a sub-parent.

Figures 3C, 3D:
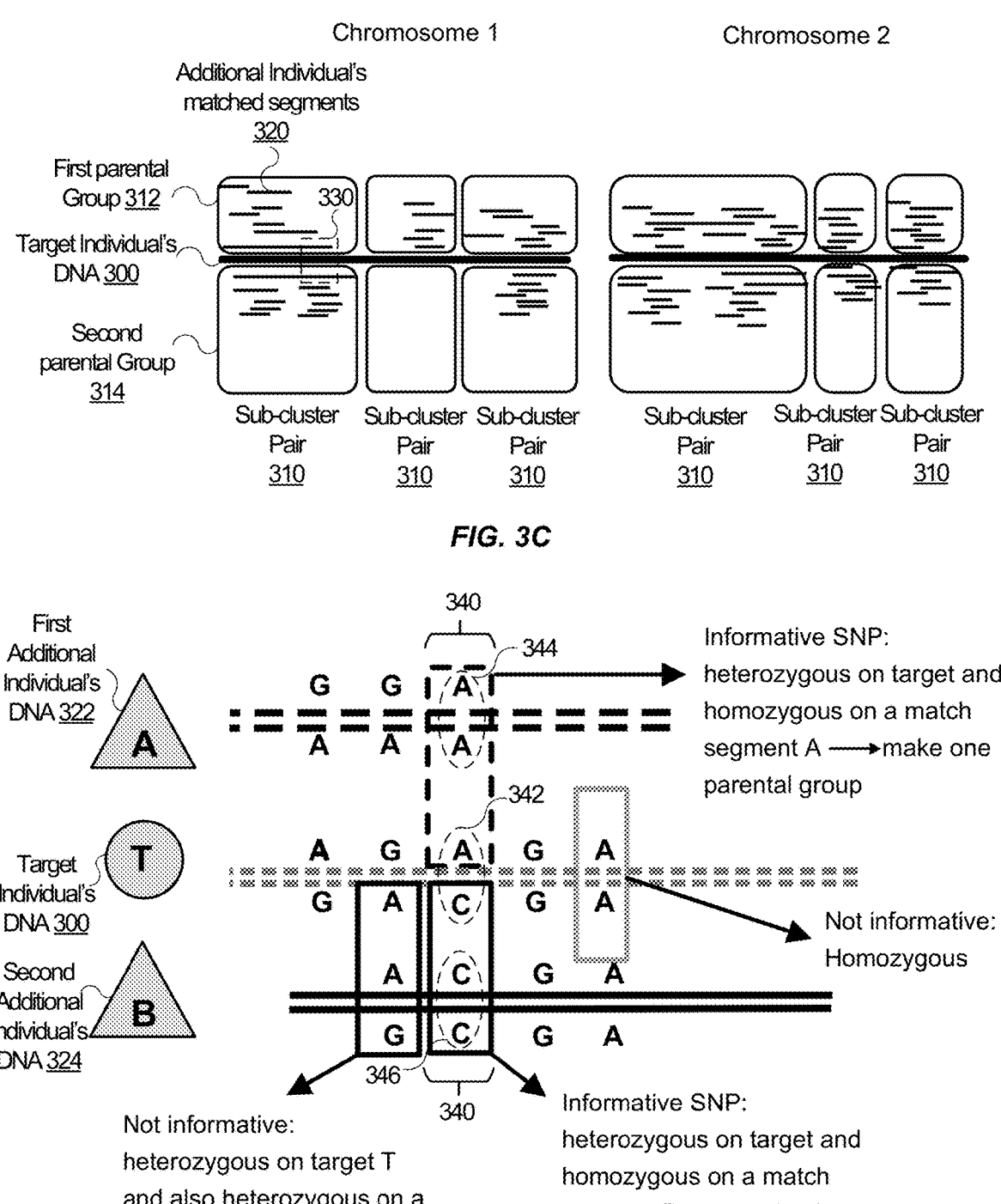

The computing server may generate a plurality of sub-cluster pairs, each pair including a first parental group and a second parental group. FIG. 3C illustrates a conceptual diagram for multiple sub-cluster pairs 310. Thick horizontal lines in FIG. 3C represent the target individual's DNA 300. Thin and shorter horizontal lines represent additional individuals' matched segments 320. Horizontal lines 320 at the same vertical level represent different matched segments of the same additional individual. Each sub-cluster pair 310 may correspond to a segment of the target individual's DNA 300. The segment may correspond to one or more genetic loci. Each sub-cluster pair 310 has a first parental group 312 and a second parental group 314. For each segment that corresponds to a sub-cluster pair 310, the computing server 130 may identify additional individuals' matched segments 320 that match (e.g., matched by IBD) the target individual's DNA 300 and classify the matched segments to one of the two parental groups 312 or 314.

FIG. 3D illustrates an example process of classifying matched segments of additional individuals to one of the two parental groups 312 or 314, in accordance with some embodiments. FIG. 3D is a conceptual diagram illustrating an enlarged view of a region 330 in FIG. 3C, which includes the target individual's DNA 300, a first additional individual's DNA 322 (a first matched segment), and a second additional individual's DNA 324 (a second matched segment). In some embodiments, the computing server 130 may use one or more heterozygous allele sites of the target individual DNA dataset to classify different matched segments into two different parental groups 312 and 314. For example, the computing server 130 may identify a particular heterozygous allele site (e.g., 342) of the target individual DNA dataset at a genetic locus. The heterozygous allele site 342 includes a first allele (e.g., A) and a second allele (e.g., C) that is different from the first allele. The computing server 130 may assign the first allele as the first parental side and the second allele as the second parental side.

The computing server 130 may use an informative SNP site to for the classification of two parental sides. In some embodiments, to separate two parental sides, the computing server 130 may identify an allele site that has a heterozygous allele for the target individual and homozygous alleles at the same site of one or more matched individuals. Taking the third site 340 in FIG. 3D as an example, the computing server 130 may start with a heterozygous allele site 342 (A-C) of the target individual DNA. The computing server 130 identifies that a first matched segment of a first additional individual has homozygous (A-A) alleles 344 at the allele site 340 and classifies the matched dataset to the first parental side. Likewise, the computing server 130 identifies that a second matched segment of a second additional individual has homozygous (C-C) alleles 346 at the allele site 340 and classifies the second matched segment to the second parental side. In some embodiments, an informative SNP site may be a heterozygous allele site of the target individual DNA dataset that has at least two corresponding additional DNA datasets of two potential relatives who each has homozygous alleles at the site. While for the particular case shown in FIG. 3D that the homozygous alleles of the two matched individuals are different (e.g., one with A-A and another with C-C), in some cases, the homozygous alleles of the two matched individuals may be the same (e.g., both with A-A or both with C-C). If the computing server 130 identifies a second matched individual whose DNA dataset also has a homozygous allele at the target allele site but the allele is different from the first matched individual (e.g., the first matched individual is A-A and the second matched individual is C-C), then those two match individuals may correspond to two parental sides of the target individual. If the computing server 130 identifies a second matched individual whose DNA dataset also has a homozygous allele at the target allele site and the allele is the same as the first matched individual (e.g., both individuals have A-A), then those two match individuals may correspond to the same parental side of the target individual.

In classifying one or more candidate additional DNA datasets to either parental group of the target individual, the computing server 130 may break those one or more candidate additional DNA datasets into segments if matching fails (e.g., a candidate matched segment 320 fails to match the haplotype of the target individual) as the computing server 130 continues to examine the sequences. By way of example, the computing server 130 may retrieve a plurality of candidate additional DNA datasets of other individuals that are contiguous subsets of SNPs corresponding to the target individual's sequence 300. A candidate matched segment 320 (a sequence from DNA dataset of an additional individual) may share the same haplotype on the same parental side with the target genotype sequence for a length that exceeds a predetermined threshold. For example, the computing server 130 may begin at the informative heterozygous site A-C 342 of the target individual's sequence 300. The computing server 130 may classify candidate matched segments 320 that have A-A at the target site 340 and identify this group of candidate matched segments 320 as the first parental side. The computing server 130 may also classify other candidate matched segments 320 that have C-C at the target site 340 to the second parental side. At this point, in some cases, not all retrieved candidate matched segments 320 are grouped yet because some candidate matched segments 320 have heterozygous alleles at the target site 340 or have missing data at the target site 340. The computing server 130 may move along the target individual's sequence 300 to identify another heterozygous site (e.g., a site having alleles C-T, not shown in FIG. 3D). At this second heterozygous site, additional candidate matched segments 320 that were not classified at the first heterozygous site 340 (due to the candidate's site being heterozygous or due to missing data) may be classified. Also, the computing server 130 determines classified candidate matched segments 320 that are contradicting each other. For example, two candidate matched segments 320 may be classified to the same parental side due to both having A-A at the first site 340. Yet, at the site that corresponds to the second heterozygous site of the target individual, the two candidate matched segments 320 have contradicting homozygous alleles (e.g., one having C-C and another having T-T). In such a case, the computing server 130 breaks one of the two candidate matched segments 320 into segments that separate the conflicting sites. As a result, an additional individual's matched segments 320 at the same vertical level (i.e., representing the same individual) may be broken into various segments.

The contradiction in various sites among different candidate matched segments 320 may be attributable to various reasons. For example, the target or candidate sequences may be wrong due to genotyping error or imputation error. A candidate matched segment 320 may have incorrect endpoints (e.g., the sequence extends beyond where the haplotype sharing really stops). The candidate sequences may share the alleles with the target individual's sequence with both parents but the candidate matched segments 320 switch at some point because of a recombination event in the family history. The last case may occur relatively frequently among matches between the target individual and other descendants of the target's parents (e.g., her siblings, nephews, children, etc.). Hence, the computing server 130 may break up a candidate matched segment 320 by inserting breakpoints to create two matched segments. In some cases, after inserting breakpoints, small segments that are shorter than a predetermined threshold may be discarded.

Put differently, each segment of the target individual's DNA dataset may include a number of informative SNPs. In some cases, not all alleles on the same matched segment 320 have the same parental group. For example, the first 30 SNPs might belong to the first parental group, but the next 20 SNPs might belong to the second parental group. There could be a number of reasons for this phenomenon: (1) the matched segment is from a descendent of the target individual and therefore, the match could be on both sides of the family and (2) the matched segment might be extended erroneously due to the IBD matching process, which allows match extension until a homozygous mismatch happens. In the second case, the part of the match that is wrong may not belong to either parent. The issue may be resolved by breaking up the matches at positions. These positions are selected by considering the evidence presented other matched segments overlapping the target individual at the loci of question. After matches are broken into segments that are consistently on only one parental side, only segments with length over a certain threshold (e.g., 5 cM) are kept for further clustering into pairs of parental groups.

In choosing to add breakpoints to segments, the computing server 130 may try to reduce or minimize the number of segments that are broken at places where the segment really shares a haplotype with the target individual. Given the choice between breaking many matches and breaking a few, the computing server 130 may choose to break a few. The computing server 130 may also consider the confidence that a matched segment shares a haplotype with the target individual, which is lower near the endpoints (beginning and end) of the segment because the matched segments are generally estimated in a way that allows them to be too long on either or both side.

In some embodiments, after the candidate matched segments 320 are broken, there are no more conflicts. That means any pair of matches will either have the exact same homozygous genotype or the exact opposite homozygous genotype (i.e., homozygous for different alleles than each other) at the informative sites. The process of detecting conflicts may classify matches into two parental groups 312 and 314. In some embodiments, the matches in the same parental group share the same alleles at the sites within a segment that is between two breakpoints. Two matches in the opposite parental groups 312 and 314 have opposite alleles (as reflected in the heterozygous alleles in the target individual) within the segment between the two breakpoints.

The two opposite groups may constitute a sub-cluster pair 310. The first group of the sub-cluster pair 310 may be referred to as a first parental group 312 because the classified matches share the same haplotype with the target individual. The computing server 130 may carry out the classification process simultaneously for the second allele of the heterozygous allele sites within two breakpoints of the target individual's segment to classify other matches to a second parental group 314. The classified matches in the second parental group 314 may share the same haplotype with the target individual but have the opposite haplotype of the first parental group 312. The first parental group 312 and the second parental group 314, both related to one or more heterozygous allele sites of the target individual, may be referred to as a pair of parental groups.

The group assignments in different sub-cluster pairs 310 do not always need to be unique. Each "side" (top vs. bottom in FIG. 3C) of a sub-cluster pair (sometimes these sides may be referred to "sub-groups" or "sub-parents") shares a haplotype inherited from one particular parent. However, in some embodiments, which haplotype belongs to father or mother may be undetermined at this point. For example, the top parental group 312 of the first sub-cluster 310 may belong to the father side while the top parental group 312 of the second sub-cluster 310 may belong to the mother side. When two sub-clusters 310 do not contain matches that overlap each other significantly, which sub-parent of a sub-cluster 310 corresponds to the same parent of the other sub-clusters may be difficult to determine. If two sub-clusters only overlap by a small amount (i.e., one or a few matches from either sub-clusters overlap with each other by a small number of SNPs), the matches may extend beyond the point where the two genotypes truly share a haplotype, so inference could be error-prone. As such, in some embodiments, a threshold may be set for defining a sub-cluster 310. For example, sub-clusters 310 may be a set of matched segments such that each overlaps another by a significant number of informative sites. The minimum number of overlap informative sites may correspond to a predetermined threshold (e.g., 30). The threshold may also be in the range of 5, 10, 20, 30, 50, 100, 150, 200, 500, 1000, etc. To build or expand one or more sub-clusters 310, the computing server 130 may start with each matched segment in its own sub-cluster and go through other matches. If the matches overlap by more than a threshold number of informative sites, the computing server 130 may join both of their entire sub-clusters into one.

The computing server 130 may further repeat the breaking of candidate matched segments 320, identification of matches, and building and expanding of sub-clusters for other genetic loci. As such, the computing server 130 may generate a plurality of pairs of parental groups across different genetic loci. Each pair may become a sub-cluster pair 310. For example, FIG. 3C illustrates a plurality of sub-cluster pairs 310. Each chromosome may be divided into a plurality of intervals. In the particular example shown in FIG. 3C, for illustration, each chromosome is divided into three intervals, but a chromosome may be divided into many more intervals. In some embodiments, the division may correspond to known genetic loci. In other embodiments, other ways to divide the chromosome are also suitable. In the particular embodiment shown in FIG. 3C, the computing server 130 generates six sub-cluster pairs 310 of parental groups for two chromosomes.

Figure 3E:
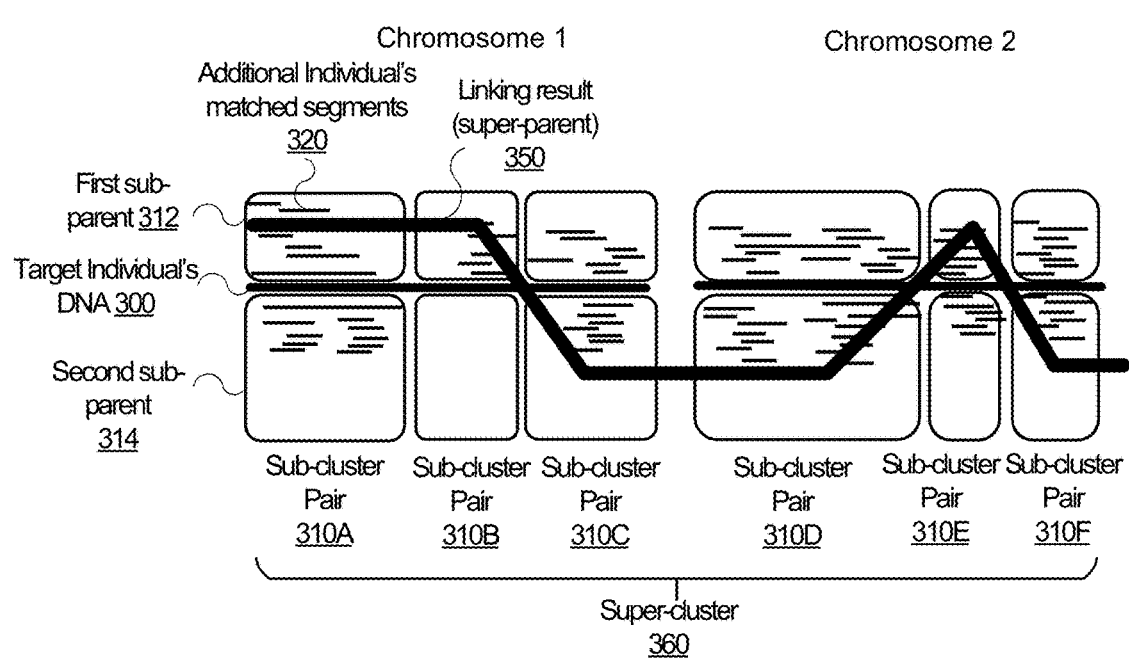

The computing server 130 may link the first parental groups 312 and the second parental groups 314 across multiple sub-cluster pairs 310 to generate at least one super-cluster of a parental side. In some embodiments, linking of the sub-clusters 310 may refer to classifying the parental groups in each sub-cluster 310 to one of the parental sides. For example, referring to FIG. 3E, while the computing server 130 classifies matched segments into one of the parental groups in each sub-cluster 310, without linking, the computing server 130 may not know if the top parental group 312 of the first sub-cluster pair 310A belong with the first parental side or the second parental side. The top parent group 312 of the second sub-cluster pair 310A, even though currently is placed on the north side of the parental side, may in fact belong to the south side of the parental side. There may be cases where the two lower parental groups may not belong to the same parental side. The reasons are that there are people who belong to the lower parental of the first sub-cluster 310A and also to the upper parental group of the another sub-cluster (e.g., third sub-cluster 310C) and/or there are many matches between the individuals belonging to the lower parental group of the first sub-cluster 310A and individuals belonging to the upper parental group of the third sub-cluster 310C. In some embodiments, the computing server 130 groups two or more sub-clusters 310 into a super-cluster based on any individuals who have multiple matched segments with the target individual in multiple sub-clusters 310 or based on matched segments among the relatives that may or may not be shared with the target individual. The linking of sub-clusters to super-cluster may be carried out using a heuristic scoring approach, a bipartite graph approach, or other suitable approaches. The linkage process may be based on similarities among the parental groups across the plurality of sub-cluster pairs. The similarities may be based on a number of common additional DNA datasets classified in different parental groups across the plurality of pairs. An example of a linking result of the linkage of sub-clusters into a super-cluster 360 is shown in FIG. 3E as a thick line 350. The linked parental groups by the linking result 350 may also be referred to as a super-parent group or simply super-parent 350. Each parental group 312 or 314 in a sub-cluster pair 310 may be referred to as a sub-parent group. A super-cluster that includes a pair of parental sides may be referred to as a pair of super-parents. Individuals whose DNA datasets are classified to one of the parental sides of the super-cluster are likely individuals that are related to the target individual on the parental side. The computing server 130 may identify one or more individuals who belong to a parental side of the target individual. The identified individuals have DNA datasets that belong to the parental side of the super-cluster.

By way of example, in some embodiments, linking of the sub-clusters 310 into one or more super-parents may include randomly assigning the super-parent groups to each sub-cluster 310, then switch the super-parent group assignment of a sub-cluster that increases the sum of similarity between all sub-parent groups in the same super-parent groups by the most, and continue switching until no switch increases the sum of similarity anymore. The process can be repeated over and over until with different random initial assignments in an attempt to find a better optimal super-parent group assignment for all sub-clusters. Sub-clusters that have sub-parent groups that have a nonzero similarity are linked together into the same super-cluster. There will be generally one or more super-clusters. Two different super-clusters remain disjoint because there is no nonzero similarity score linking any sub-parent group from one super-cluster to any sub-parent group of the other. Each super-cluster may be a phased haplotype with a long distance accuracy.

After one or more super-parent groups are identified, the computing server 130 may identify one or more additional individuals who belong to the parental side of the super-cluster as associated with a parental lineage of the target individual. The computing server 130 may assign metadata to additional individuals' DNA datasets to associate the dataset with a parental side of the target individual. For example, the computing server 130 may assign metadata to one or more additional individual datasets. The metadata may specify that the one or more additional individual datasets are connected to the target individual dataset by the parental side of the super-cluster.

In some cases, after linking sub-clusters 310, there are individuals whose matched segments 320 might belong to two sides of the family. There are a number of reasons why these individuals have matched segments 320 belonging to both parental groups: (1) the individuals might be descendants of the target individuals such as nieces or nephews; (2) the parents of the target individual might share IBD. The second reason can lead to individuals matching with the target individual as well as both of the target individual's parents. The method identifies individuals whose matched segments 320 belong to both sides of the family by finding individuals who have segments in both super-parents. These individuals may be removed from their sub-clusters 310 and the process of linking sub-clusters 310 into super-cluster 360 is repeated.

The computing server 130 may further identify whether a parental side (e.g., a super-parent 350) is the paternal side or maternal side. One or more approaches may be used to enable such identification. In one embodiment, the computing server 130 access genealogical data of the target individual to identify at least one individual in the genealogical data who belong to the super-parent 350. Based on the genealogical data, the identified individual belongs to either a paternal side or maternal side of the target individual. In another embodiment, the computing server 130 may transmit, to the target individual (e.g., a user of the computing system) or another user, an inquiry about a relationship between the target individual and one of the identified additional individuals belonging to the super-parent. For example, the computing server 130 may ask a user whether one or more close relatives belong to the maternal side or the paternal side. In yet another embodiment, the computing server 130 may examine the genetic locus of sex chromosomes or mitochondrial DNA in the super-parent to determine the parental side. For example, if a parental side of a super-parent includes some segment of the Y-chromosome, the computing server 130 may designate the parental side as the paternal side. Likewise, if a parental side of a super-parent includes some segment of mitochondrial DNA, the computing server 130 may designate the parental side as the maternal side. In another embodiment, the computing server 130 may determine an ethnicity of one or more identified additional individuals belonging to the super-parent. The server may also ask the target individual or another user if the user knows her parents' or grandparents' genetic communities. This information may also be used to identify the maternal side or parental side because a super-parent 350 may be clustered or otherwise classified into one of the genetic communities using community assignment engine 230 or ethnicity estimation engine 245.

In one embodiment, in determining a parental side, the computing server 130 may rely on genealogical data such as pedigree and family tree information. The computing server 130 may collect the number of matched segments 320 that can be assigned to the maternal/paternal side by the genealogical data to determine which side of the family a sub-cluster belongs to. A machine learning model may be trained to a sub-cluster level classifier to assign top/bottom sub-cluster to maternal/paternal side with a probability given the number of maternal/paternal segments found in top/bottom sub-cluster. The prediction result is the assignment of the maternal/paternal side of the family for a top/bottom sub-cluster, which can be determined to use or not based on its classification probability. Similarly, a machine learning model (e.g., logistic regression) may be trained as a super-cluster-level classifier to assign top/bottom super-cluster to the maternal/paternal side of the family.

In determining whether a DNA dataset has a matched segment that matches the target individual DNA dataset, the computing server 130 may use a predetermined number of consecutive sites as a threshold to determine which parental group the match belongs to. In one embodiment, the predetermined number may be set as a fixed number such as 30 allele sites. In another embodiment, the computing server 130 may determine the threshold amount based on validation data. For example, the computing server 130 may examine different threshold amounts to generate different sub-clusters and super-clusters to determine an appropriate level of threshold that leads to the best accuracy in identifying individuals into different parental sides.

Figure 3F:
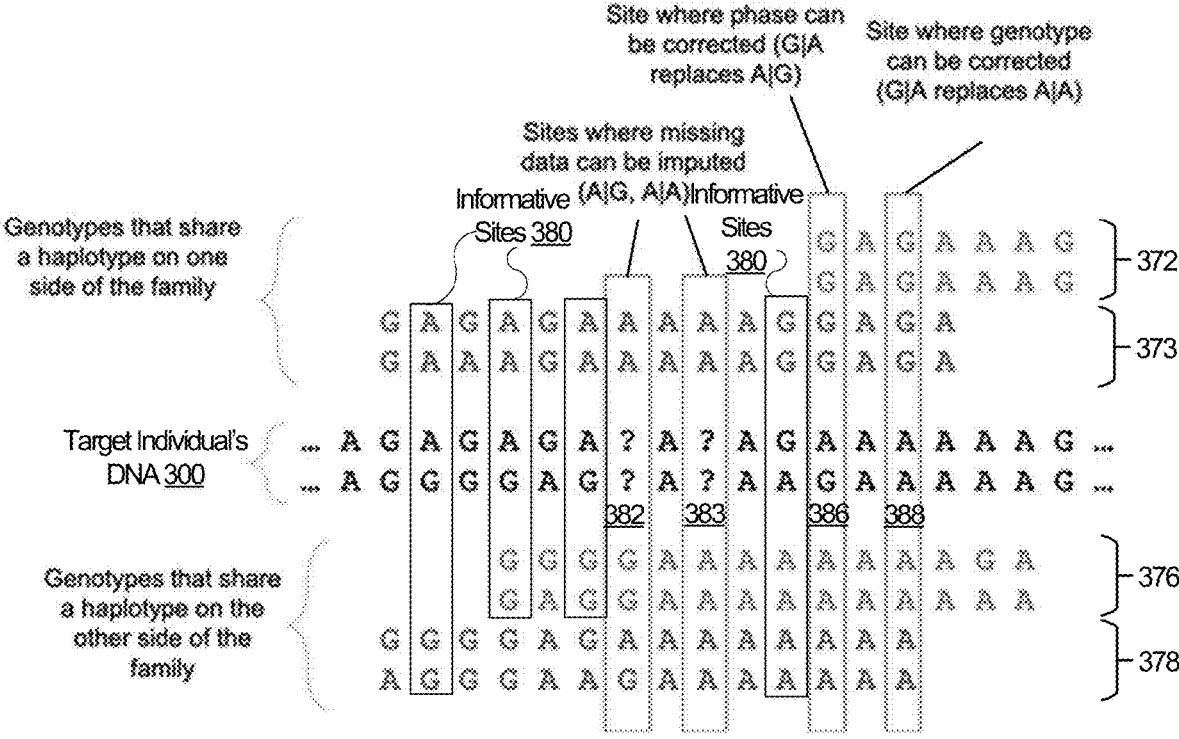

FIG. 3F is a conceptual diagram illustrating a process of haplotype phasing and imputation of missing values for the target individual, in accordance with some embodiments.

In generating at least a sub-cluster pair, the computing server 130 assigns matched segments to two parental groups. In FIG. 3C, the computing server 130 may identify heterozygous sites in the target individual's DNA 300. The computing server 130 identifies additional individuals' matched segments 372, 374, 376, and 378. Based on the heterozygous alleles of the target individual's DNA 300, the computing server 130 classifies the matched segments to one of the two sides of the family (e.g., one of the two parental groups). The computing server 130 may identify one or more informative sites 380 in which the target individual's DNA at those sites are heterozygous while the matched segments 372, 374, 376, or 378 at those sites are homozygous. In some cases, the computing server 130 may also identify homozygous sites of the target individual that match the additional individuals.

The computing server 130 may identify 390 target sites in the target individual's DNA dataset. By way of non-limiting example, the computing server 130 may select target sites based on a distance between a candidate site and another site that the computing server 130 deems as a high-confidence site. High-confidence sites may be informative sites 380 or homozygous sites in which both the target individual and the additional individuals have the same allele. Target sites are in the same proximity of the high-confidence sites, such as sites that are within a threshold distance from at least one information site 380 or sites that are belong to the same sub-cluster or the same genetic loci. The computing server 130 may perform 395 imputation of allele values, phasing of haplotype, and/or correction of genotype value at the target sites. For example, at the target individual's sites 382 and 384, the sequencing result does not provide a genotype value at those sites. Based on the matched segments 372, 374, 376, and/or 378 that are assigned to two different sides of the family, the computing server 130 imputes that the haplotype values at the first missing site 382 as AG by identifying homozygous matched segments at those sites. Likewise, the computing server 130 imputes the haplotype values at the second missing site 384 as A|A. The computing server 130 may also phase or correct phasing error performed by phasing engine 220 using the matched segments in the sub-cluster. For example, at the heterozygous site 386, the values A|G can be either unphased or phased with an error. The computing server 130 reviews the homozygous allele values of matched segments 372, 374, 376, and/or 378 at the site 386. The computing server 130 determines that the correct phasing should be G|A instead of A|G. The computing server 130 may also use the matched segments to correct a genotyping error. For example, at the site 388, the genotyping result produced by sequencing is A|A. However, the matched segments 372 and 374 suggest that the alleles should be G|A.

In any cases when genotyping or haplotype phasing errors are detected, the computing server 130 may choose to override the genotype in the original data, choose to override the genotype in the phased data (often the diploid data have missing calls and the phased data do not), or choose to override the genotype in both the original and phased data. The computing server 130 may determine the extent of overriding data based on one or more factors. For example, the factors may include the number of matched segments support the identification of error, the number of matched segments on either side of the family, the number of matched segments being homozygous at the site where an error is found, and which alleles the matched segments are homozygous. The factors may also include whether the computing server 130 is changing a genotype assignment or not and what the original genotype is. The factors may further include the confidence in the IBD segments (e.g., how certain the computing server 130 is that the segment shares a haplotype with the target individual). The confidence in the IBD segments may be based on genotype data and supporting information, including but not limited to the proximity of the SNP in question to either end of the segment, the length of the segment, and the estimated amount of DNA shared with the same individual as the IBD segment in other places on the genome.

The jib phasing technique can improve the phasing method used by the phasing engine 220 by at least 35%. The match-clustering based haplotype phasing can also improve the performance of genetic communities and ethnicities used in community assignment engine 230 and ethnicity estimation engine 245.

Example Heuristic Scoring Approach in Jig Phasing

In some embodiments, the computing server 130 generates one or more super-clusters and their linking using a heuristic scoring method. The computing server may calculate the similarity between sub-parents of different sub-clusters 310. Each matched segment 320 in a sub-cluster 310 corresponds to a different relative of the target individual. In some embodiments, the similarity between sub-parents of two sub-clusters 310 may be based on a number of matched segments 320 whose corresponding relatives are shared between the two sub-parents in two sub-clusters 310. In other words, it is based on the number of matched segments in the two sub-cluster-sub-parents whose corresponding relatives are the same. For example, if a person has 2 segments in the upper parental group of sub-cluster 1 ( $sub\_1\_p0$ ) and 5 segments in the lower parental group of sub-cluster 3 ( $sub\_3\_p1$ ), then the similarity score between these two sub-cluster-sub-parents groups (i.e. $sub\_1\_p0$ and $sub\_3\_p1$ ) is based on the 7 segments corresponding to this person. In some embodiments, the similarity between two sub-parents in sub-clusters 310 may be based on the number of matched segments 320 in one sub-parent whose corresponding relative is "a match" of the corresponding relative of a matched segment in the other sub-parents. In some embodiment, the similarity score is based on the number of matched segments in the two sub-parents whose corresponding relatives are matches of each other. For example, if a person A has segments in $sub\_1\_p0$ and a person B has segments in $sub\_3\_p1$, and persons A and B match each other on X segments, then the similarity score between these two sub-cluster-sub-parents groups (i.e. $sub\_1\_p0$ and $sub\_3\_p1$ ) is based on the X segments shared between person A and person B. In some embodiments, the similarity between two sub-parents may be based on a combination of the number of matched segments in the two sub-parents whose corresponding relatives are the same, and the number of matched segments in the two sub-parents whose corresponding relatives are matches of each other. In some embodiments, the result may be a similarity matrix Sim(i, j, k) where i, j are indices of sub-clusters. k=True if the computing server 130 compares sub-cluster i, top to sub-cluster j, top and sub-cluster i bottom to sub-cluster j bottom. k=False if the computing server 130 compares sub-cluster i, bottom to sub-cluster j, top and sub-cluster i top to sub-cluster j bottom.

The computing server 130 may link sub-clusters 310 into one or more super-clusters 360 based on the similarities between sub-clusters 310. As a result of this step a sub-cluster 310 is assigned to a super-cluster 360 and a target individual can have one or more super-clusters 360 depending on the similarity between their sub-clusters 310.

The computing server 130 may choose the best configuration (or one of the best) of super-cluster-super-parent for each of one or more super-clusters. A configuration of super-cluster-super-parent for a super-cluster represents a set of assignments of super-parents (e.g., first super-parent/second super-parent, 0/1, mother/father, true/false or any other appropriate values) to each of the sub-cluster-sub-parent groups within the super-cluster. The configuration indicates which sub-cluster-sub-parents correspond to a first super-parent and which ones correspond to a second super-parent. A sub-cluster 310 includes two sub-parent groups 312 and 314 (FIG. 3E), e.g., sub-cluster-sub-parent 0 and sub-cluster-sub-parent 1, wherein sub-cluster-sub-parent 0 is the part whose sub-parent is assigned (e.g., a first sub-parent), and wherein sub-cluster-sub-parent 1 is the part whose sub-parent is assigned (e.g., a second sub-parent). A super-cluster 360 may include two super-parent groups, such as super-parent 0 and super-parent 1, wherein super-parent 0 and super-parent 1 are the result of linking sub-clusters 310. A super-cluster 360 includes one or more sub-clusters 310. A super-parent 350 includes one or more sub-parents 312 or 314 that are linked. The similarity score of a super-cluster 360 is defined based on the sum of similarity scores between sub-clusters within each super-parent of the super-cluster 360.

To find the best configuration of the linking of a super-cluster 360, the computing server 130 chooses a group of candidate configurations of super-parents. The computing server 130 selects the candidate configuration from the group of candidate configurations which results in the highest similarity score of the super-cluster as the best configuration of super-cluster-super-parent.

To find a candidate configuration for a super-cluster 360, the computing server 130 randomly assigns a super-parent (e.g., first super-parent or second super-parent) to each sub-parent 312 or 312 in various sub-clusters 310. The computing server 130 switches the assignment of the super-parent label if switching increases the similarity score of the super-cluster 360, wherein all possible switching of super-parents are iterated through. The configuration corresponding to the highest similarity score of the super-cluster is chosen as the candidate configuration. Switching an assignment of the super-parent to a sub-parent means that if for a sub-cluster $sub\_i$ with two sub-parents $sub\_i\_p0$ and $sub\_i\_p1$, if initially a first super-parent is assigned to $sub\_i\_p0$ and a second super-parent is assigned to $sub\_i\_p1$, after switching the assignment, the second super-parent is assigned to $sub\_i\_p0$ and the first super-parent is assigned to $o\ sub\_i\_p1.$. Similarly, if initially a first super-parent is assigned to $sub\_i\_p1$ and a second super-parent is assigned to $o\ sub\_i\_p0$, after switching the assignment, the second super-parent is assigned to $sub\_i\_p1$ and the first super-parent is assigned to $sub\_i\_p0.$. Finding candidate configurations may be repeated for a predetermined number of times N (e.g., 1000 times) to have a group of candidate configurations. Each segment has a super-cluster and super-parent assignment. This step may be repeated multiple times: starting with a random configuration, switching the assignment until the best configuration is achieved. The best resulting configuration among the multiple random restarts is selected as the final super-cluster and super-parent assignment.

Example Bipartite Graph Approach in Jig Phasing

In some embodiments, the computing server 130 generates one or more super-clusters and their linking using a bipartite graph approach. Two sub-parent combinations in two different sub-clusters 310 can either be on the same parental side of a target individual or they are on two different parental sides of the target individual. There are cases where a person can have segments in a sub-parent that match both sides of the family (e.g., niece and nephew). In some embodiments, the computing server 130 may assume that a sub-parent can only be on one side of the target individual's family. Consider each sub-parent combination as a node in a graph and the computing server 130 may connect all pairs of nodes that are on two different parental sides of the family. The problem of assigning each sub-parent to one side of a family becomes a problem of coloring the nodes of the graph with two colors such that any two nodes connected by an edge are colored differently. In some embodiments, the computing server 130 represents a graph that could be colored with only two colors as a bipartite graph. The computing server 130 constructs a graph with sub-cluster-sub-parents combinations as nodes such that the graph is bipartite.

The computing server may calculate the similarities between all pairs of sub-parent combinations across two sub-clusters. Different embodiments may use various ways to calculate the similarity between sub-parents. In some embodiments, the similarity between two sub-parents may be based on a number of matched segments 320 whose corresponding relatives are shared between the two sub-parents. In other words, it is based on the number of matched segments in the two sub-parents whose corresponding relatives are the same. In some embodiments, the similarity between two sub-parents may be based on the number of matched segments 320 in one sub-parent whose corresponding relative is a match of the corresponding relative of a matched segment in the other sub-parents. In other words, it is based on the number of matched segments in the two sub-parents whose corresponding relatives are matches of each other. In some embodiments, the similarity between two sub-parents may be based on a combination of the number of matched segments in the two sub-parents whose corresponding relatives are the same, and the number of matched segments in the two sub-parents whose corresponding relatives are matches of each other.

Figure 3G:
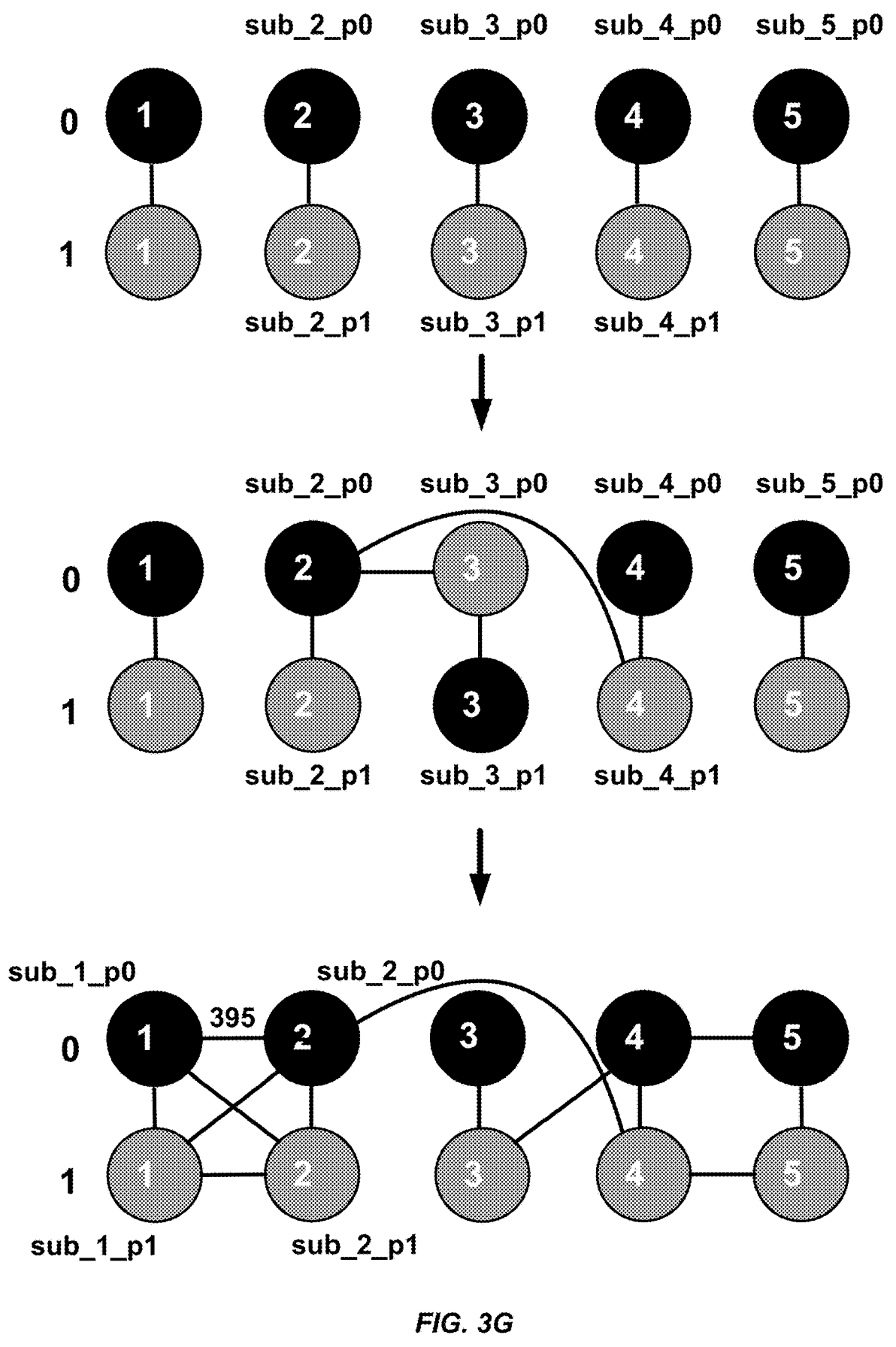

The computing server 130 may create an initial graph where each node represents a sub-parent and each edge connects two nodes whose corresponding sub-parents are on the opposite parental side. Each node has a label (e.g., color, 1/0, any suitable binary labels) which represents a parental side (paternal side or maternal side). FIG. 3G is a conceptual diagram illustrating how an example bipartite graph using colors (black and grey) as the parental side label may be built. The initial graph comprises nodes for sub-parents. For each sub-cluster *sub_i* with two sub-parents *sub_i_p0* and *sub_i_p1,*, *sub_i_p0* and *sub_i_p1* are on the opposite sides of the family. Thus, the initial graph comprises edges between nodes corresponding to such sub-parents (e.g., *sub_i_p0* and *sub_i_p1*) that are part of the same sub-cluster (e.g., *sub_i).*).

The computing server 130 may add edges between nodes of the initial graph based on the similarity between sub-parents in different sub-clusters 310 until the bipartite property is violated. The computing server 130 iterates through a list of pairs of nodes from the highest to lowest similarity for their corresponding sub-parents. The computing server 130 adds edges between pairs of nodes while bipartite property is not violated in the graph. The computing server 130 may start with the pairs of nodes with high similarity (the highest similarity). For example, if there is a high similarity between *sub_2_p0* and *sub_4_p0,*, then *sub_2_p0* and *sub_4_p1* are on the opposite side of the family and an edge will be added between *sub_2_p0* and *sub_4_p1.*. The computing server 130 may go down the list of the pairs of nodes from the highest to lowest similarity and continue to assign edges. If there is a high similarity between *sub_2_p0* and *sub_3_p1,*, then *sub_2_p0* and *sub_3_p0* are on the opposite side of the family and an edge will be added between *sub_2_p0* and *sub_3_p0.*. If the graph becomes non-bipartite (e.g., having an odd cycle), the computing server 130 may disconnect the most recently connected pairs.

Once all possible edges are added, the computing server 130 has completed a bipartite graph. The computing server 130 may assign a parental-side label (e.g., color) to each sub-parent. Each label corresponds to a side of the family.

In some embodiments, the computing server 130 generates two or more super-clusters using a bipartite graph applying backward formulation. The computing server 130 may calculate the similarities between all pairs of sub-parent combinations. Different embodiments may use various ways to calculate the similarity between sub-parents. This step may use various embodiments to calculate the similarity between sub-parents.

The computing server 130 may create an initial graph where each node represents a sub-parent. Edges are created between all pairs of nodes in the initial graph to represent the potential sub-parents that are on the opposite parental sides.

The computing server 130 may remove edges between nodes of the initial graph based on the similarity between sub-parents corresponding to the nodes. The computing server 130 may iterate through a list of pairs of nodes from highest to lowest similarity for their corresponding sub-parents. The computing server 130 may remove edges between the pair of nodes until bipartite property is established in the graph. At an instance during iteration through the list of pairs of nodes from highest to lowest similarity for their corresponding sub-cluster-sub-parents, the computing server 130 reaches the pair of nodes *sub_1_p0* and *sub_2_p0,*, as the one with the highest similarity. The computing server 130 then removes the edge 1010 between *sub_1_p0* and *sub_2_p0* because it violates bipartite property. In other words, because *sub_1_p0* and *sub_2_p0* are highly similar, their corresponding sub-cluster-sub-parents should be on the same side rather than the different side of the family, hence the edge 395 is removed.

Once all possible edges that cause violation of bipartite property in the graph are removed, the computing server 130 has completed a bipartite graph, in which each sub-cluster-sub-parent combination is assigned a parental-side label (e.g., color). Each label corresponds to a side of the family.

In some embodiments, the computing server 130 may generate two or more super-clusters using a combination of heuristic scoring and a bipartite graph. The computing server 130 runs the heuristic scoring method described above and calculates the similarity score of the resulting super-clusters. The computing server 130 also runs bipartite graph methods (forward formulation and/or backward formulation) and calculates the similarity score of the resulting super-clusters. The computing server 130 compares the calculated similarity scores and outputs the results corresponding to the best similarity score.

A Two-Step Approach to Label Assignment

After a pair of phased haplotype datasets are generated from an input sample genotype dataset X, the label determination system 270 assigns labels to the input genotype dataset X by using and constructing an inter-window hidden Markov model (inter-window HMM). The genetic data store 205 stores one or more pairs of phased haplotype datasets. The label determination system 270 may assign labels to the input sample genotype dataset X based on the pair of phased haplotype datasets. The inter-window HMM store 278 stores an inter-window HMM corresponding to the input sample genotype dataset X that is used to determine the labels. The inter-window HMM is computed or built by the inter-window HMM module 288. The inter-window HMM includes states for each window w.

While ethnicity labels are used as the primary example of a type of genotyping labels that may be assigned by HMMs, other types of genotyping labels that stand for a particular property of a segment of genetic data may also be used. For example, each label may represent, instead of ethnicity, phenotype assignment, disease assignment, variant assignment, and other trait assignment, observable or not. Hence, without the loss of generality, the use of ethnicity labels as an example can be expanded to other embodiments that use another type of genotyping label. In those embodiments that do not use ethnicity labels, the HMM 400 may be referred to as a full-label HMM. The composition determined may be referred to as genotyping label composition.

Figure 4A:
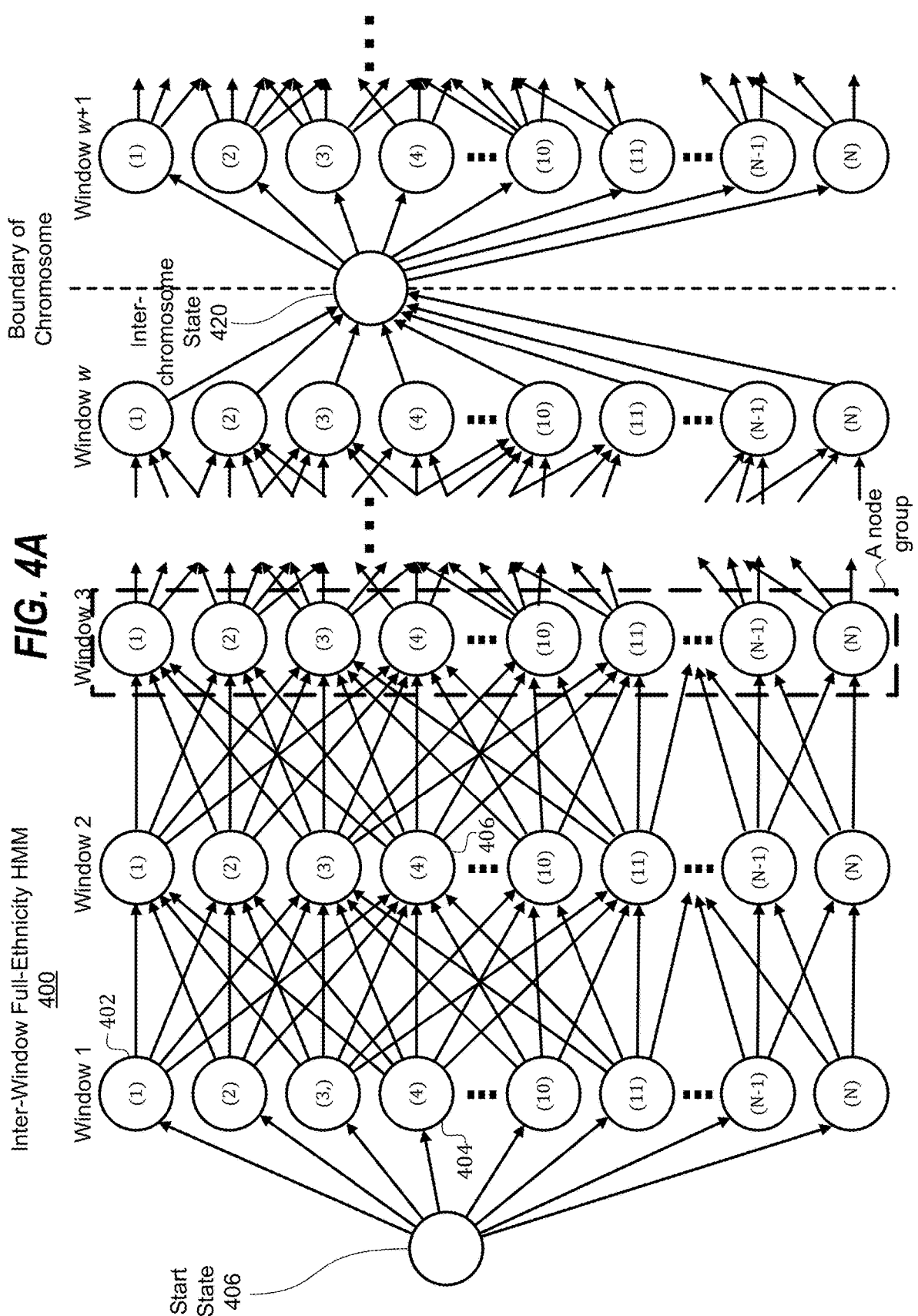
FIG. 4A and FIG. 4B are diagrams illustrating an inter-window of a hidden Markov model, in accordance with some embodiments.
Figure 4B:
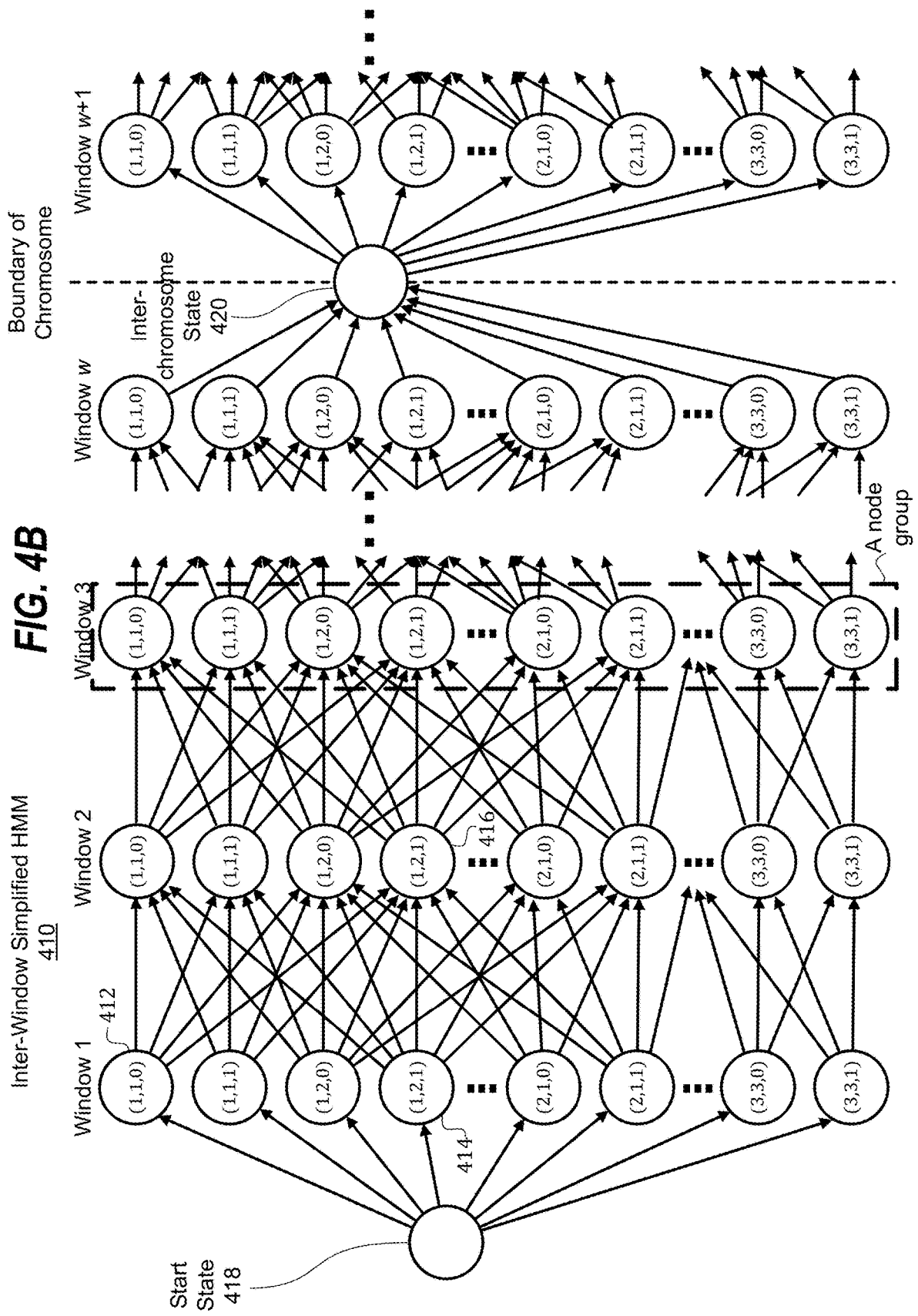

FIG. 4A and FIG. 4B illustrate a simplified example of an inter-window HMM 400 and 410, according to some embodiments. The inter-window HMM 400 and 410 may be a directed (e.g., in the direction from left to right as shown in FIG. 4A and FIG. 4B) acyclic graph that includes a plurality of node groups. The graph representing the inter-window HMM 400 and 410 may also be referred to as a trellis. Graphically, each node group in the trellis may also be referred to as a level, a slot, a graph window, or a layer. Each node group represents a window w that corresponds to a genetic segment such as a set of SNPs. A plurality of nodes (represented by the circles in FIGS. 4A and 4B) are arranged in each node group. Each node represents a possible state of the window w. Each node is associated with an emission probability representing a likelihood of the window is observed as having a particular pair of phased haplotype datasets given the window is having the hidden state (i.e., the window is assigned with a particular pair of labels). In other words, the particular pair of phased haplotype datasets may be an observation in a hidden Markov model while the state that is labeled may be the "hidden" state of the hidden Markov model because the labels are not apparent given only the genotype dataset or the phased haplotype dataset. The inter-window HMMs 400 and 410 also include a plurality of edges. Each edge connects a first node of a first node group to a second node of a second node group. Each edge represents a transition from the first node of the first node group to the second node of the second node group.

Each edge is associated with a transition probability that represents the likelihood of transition from the first node to the second node.

In the first stage, an inter-window full-ethnicity HMM 400 may be used. The inter-window full-ethnicity HMM 400 may take the form of a haploid model that is configured to receive haplotypes as inputs. A state (represented by a node) in the inter-window full-ethnicity HMM 400 includes one label. The label is representative of an ethnicity from the computing server 130. Every node in a node group receives a label. Each of the labels in a state is represented by an integer value. For example, both the first parent label and the second parent label are selected from a set of K possible labels. A label is a classification of genetic data. Since ethnic origins are used as classification, the set of N possible labels may be African, Asian, European, etc. or be German, Korean, Mexican, etc., depending on the granularity of the classification. A particular integral value represents one of the labels. For example, 1 may represent European while 2 may represent Asian. The computing server 130 may maintain a set of N possible ethnicity labels and the inter-window full-ethnicity haploid HMM 400 may include N possible labels for each window. While the HMM 400 is described as full-ethnicity HMM, in some embodiments the HMM 400 does include each and every possible ethnicity label that is maintained by the computing server 130. However, in some embodiments, the full ethnicity is merely a reference to a set of ethnicity labels and the HMM 400 includes every label in that set. However, the set does not necessarily include each and every possible ethnicity known in the world. For example, in some embodiments, the computing server 130 may develop an HMM specifically to a continent (e.g., an Asia HMM) and the set of ethnicity labels includes only Asian ethnicity. In that case, the full ethnicity HMM includes all labels that are relevant to the Asian set.

The inter-window full-ethnicity HMM 400 is initiated by the computer server 130 for a haplotype sequence of a target individual that is phased. Since each individual has a pair of haplotype sequences, two inter-window full-ethnicity HMMs 400 may be initiated, one for each haplotype in the phased genotype. In other words, the computing server 130 runs a full-ethnicity HMM for each of the first haplotype and the second haplotype, with each haplotype representative of a parent of the target individual. The haplotype sequences used may be determined by a phasing algorithm that has a long distance (e.g., cross-chromosome) accuracy, such as the jig algorithm discussed above in FIG. 3C through FIG. 3G. Another phasing algorithm may be used but the accuracy may be significantly improved the more the phasing is accurate in a global scale.

Using node 402 as an example to explain the concept of emission probability in the inter-window full-ethnicity HMM 400, the emission probabilities here represent the likelihood that Window 1 is observed in a haplotype sequence of the target individual to have a particular haplotype sequence given the Window 1 should be labeled as having a particular ethnicity origin labeled as (1). Likewise, the transition probability from the node 402 to the node 406 represents the likelihood that the first segment of the haplotype of SNPs (corresponding to Window 1) transitions to the second segment of the haplotype of SNPs (corresponding to Window 2) that should be labeled as ethnicity origin (4). Likewise, the transition probability of the node 404 to the node 406 represents the likelihood that the two segments have no change in ethnicity origin and the ethnicity origin label remains to be (4).

The computing server 130 trains the HMM 400 to determine converged emission probability values and transition probability values. The computing server 130 applies a path determination dynamic programming algorithm such as a Viterbi algorithm to determine a probability most likely path for each HMM 400 using the input of a haplotype sequence of the target individual. From the two haplotype sequences, the computing server 130 determines two subsets of ethnicity labels. For example, the computer server 130 uses the inter-window full-ethnicity HMM to determine a first subset of ethnicity labels that matches the first haplotype and a second subset of ethnicity labels that matches the second haplotype. The computing server 130 combines the two subsets to create a candidate subset of ethnicity labels. The candidate subset of ethnicity labels may be considered a candidate ethnicity composition for the target individual. A path may start from the start state 406 and traverse one node per window until the entire HMM is traversed.

With the candidate subset of ethnicity labels determined, the computing server 130 may move to the second stage and initiate a simplified diploid inter-window HMM 410. The HMM 410 is simplified in the sense that it includes only the ethnicity labels determined to match each haplotype for the target individual. However, the diploid inter-window HMM 410 may include an ordered label of haplotype ethnicity assignment and a switching label. For example, a state (represented by a node) in the inter-window simplified HMM 410 includes three different labels. In the particular embodiments shown in FIG. 4B, the three labels are orderly presented as a first parent label, a second parent label, and a switch label that represents a switch of the order between the first parent label and the second parent label in the particular window, where the switching may be associated with phasing errors. While the order of presentation in the embodiment is shown in FIG. 4B is the first parent label, the second parent label, and the switch label, other orders of presentation are also possible.

Each of the three labels in a state is represented by an integer value in the simplified HMM 410. Both the first parent label and the second parent label are selected from the candidate subset of ethnicity labels, instead of all N possible labels in the full-ethnicity inter-window HMM 400. For example, if N possible labels in the full-ethnicity HMM 400 include German, French, Korean, Japanese, etc. and in the first stage where the full-ethnicity HMM 400 determines that only German, Korean, and Japanese are in the candidate set, the simplified HMM 410 contains labels for only German, Korean, and Japanese, but not French. Since the labels used in the simplified HMM 410 are based on the possible ethnicity candidate labels for the target individual, the simplified HMM 410 initiated is tailored to the target individual based on the first stage. For each node in the simplified HMM 410, the first two labels are ordered labels of ethnicity labels with respect to the pair of haplotypes. The phased genotype (both haplotypes in the pair) is inputted into the simplified HMM 410.

The third label of a node, which is the switch label, may take a binary value (e.g., 1 or 0). The first binary value (e.g., 1) may represent that there is a switching of order of the first parent label and the second parent label while the second binary value (e.g., 0) may represent that there is no switching of order. A switch label represents a switching of order of the first parent label and the second parent label. In other words, a switch label represents that, for a particular state, the order of the first parent label and second parent label in the simplified HMM 410 is switched compared to the actual labels in the sample. Using the examples discussed in this paragraph as an illustration, the first node 412 of Window 1 in FIG. 4B, which takes the values (1, 1, 0), may represent the state that Window 1 is labeled as having the first label (e.g., the first label is assigned to German) for both the first parent label and second parent label and there is no switching of order between the two labels.

Likewise, the fourth node 414 of Window 1 in FIG. 4B, which takes the values of (1, 2, 1), may represent the state that Window 1 is labeled as German for the first parent label and Korean (e.g., the second label is assigned to Korean) for second parent label but there is a switching of order between the two labels. In other words, due to one or more possible, but unobserved reasons such as a phasing error, the fourth node 414 represents the ground truth that Window 1 has Korean as the first parent label and German as the second parent label but for some reasons such as phasing error that the model assigns German as the first parent label and Korean as the second parent label.

Using node 412 as an example to explain the concept of emission probability in the inter-window simplified HMM 410, the emission probabilities here represent the likelihoods that, based on the phased genotype (a pair of haplotypes) of the target individual, the window 1 is observed to have that particular pair of haplotype sequences given the Window 1 should be labeled as having German and German for both haplotypes. The third label represents that the phasing is correct with respect to window 1. The transition probability from the node 412 to the node 416 represents the likelihood that a first segment of SNPs (corresponding to Window 1), which should be labeled as having German origin for both first and second parents, transitions to a second segment of SNPs (corresponding to Window 2) that should be labeled as having German origin for the first parent and Korean origin for the second parent, and also there is a switching of first parent label and second parent label.

The plurality of nodes in each node group represents permutations of different possible first parent labels, second parent labels, and switch labels that can be assigned to a window. For each window, the inter-window simplified HMM 410 may include a set of states corresponding to every ordered set of labels. Hence, the total number of states (T) can be K*K*2 (first parent labels K*second parent labels K*binary switch labels) for each window. For illustration purposes, only some of the states are shown in FIG. 4B for each window.

The computing server 130 uses the full-ethnicity HMM 410 to narrow the possible set of ethnicity labels from hundreds to a subset of candidate ethnicity labels determined to match one or both of the target individual's haplotypes. For example, K is generally smaller (usually much smaller) than N which is used in the HMM 400. For the particular embodiment shown in FIG. 4B, there are three possible values of classification labels (i.e., K=3) and the switch label takes the value of either 1 or 0. Hence, there are 3*3*2=18 possible states (i.e., T=18). Whereas for the set of possible ethnicity labels N maintained by the computing server, the N may equal any number but can be around 100. As such, without simplification, the possible states in a diploid switch-accounted HMM is about 100*100*2=20,000. As such, the complexity of the simplified HMM 410 is significantly reduced and the computation is sped up. By using the candidate ethnicity labels to initiate the simplified HMM, the computing server 130 decreases the number of possible states (T). The states for a window w are denoted as $U_w(p,q,z)$ where p is the value of the first parent label (e.g., $p \in (1,2, \ldots, K)$), q is the value of the second parent label (e.g., $0.7 \in (1,2, \ldots, K)$), and z is the value of the switch label (e.g., $z \in (0,1)$). In this way, the set of labels (p,q,z) uniquely refers to each of the possible states T. Although FIG. 4B depicts K=3 labels, the number of candidate labels K can be any natural integer.

The inter-window simplified HMM 410 is a directional graph that represents a transition from a start state to an end state (not shown in FIG. 4B) through a plurality of node groups that represent a plurality of windows. The start state 418 transitions to one of the T possible states of window 1 as illustrated by the arrows between the start state 418 and the respective T states of window 1. Each state in window 1 may transition to one of the possible states in window 2. A state $U_w(p,q,z)$ in window w may transition to a state $U_{w+1}(p',q',z')$ in window w+1. The chromosome that corresponds to the window w is denoted as C(w) while the chromosome that corresponds to the window w+1 is denoted as C(w+1). If the window w and the window w+1 correspond to the same chromosome (i.e., C(w)=C(w+1)), then a state $U_w(p,q,z)$ may be more likely to transition to a state $U_{w+1}(p',q',z')$ in window w+1 that corresponds to the same pair of labels (i.e., (p',q')=(p,q)) without switching than to a state in window w+1 that corresponds to a different pair of labels or to a state in window w+1 that corresponds to switching of labels. This is because it is biologically unlikely that the sequences of SNPs in adjacent windows will correspond to different labels (e.g., correspond to different ancestral origin groups).

In some embodiments, the transition probability $P(U_w(p, q,z), U_{w+1}(p',q',z'))$ from a state $U_w(p,q,z)$ to a state $U_{w+1}(p',q',z)$ is given by equation (1) below:

$$P(U_w(p, q, z) \rightarrow U_{w+1}(p', q', z')) =$$

$$\begin{cases} \dfrac{\pi_{p'}^m \times \pi_{q'}^f}{2} \text{ if } C(w) \neq C(w+1) \\ (1-\tau^m) \times (1-\tau^f) \times (1-\tau^z) \text{ if } C(w) = C(w+1), p = p', q = q', z = z' \\ (1-\tau^m) \times (1-\tau^f) \times \tau^z \text{ if } C(w) = C(w+1), p = p', q = q', z \neq z' \\ \tau^m \times (1-\tau^f) \times (1-\tau^z) \times \dfrac{\pi_{p'}^m}{\sum_1^{p'-1} \pi_k^m + \sum_{p'+1}^K \pi_k^m} \text{ if } C(w) = C(w+1), p \neq p', q = q', z = z' \\ \tau^m \times (1-\tau^f) \times \tau^z \times \dfrac{\pi_{p'}^m}{\sum_1^{p'-1} \pi_k^m + \sum_{p'+1}^K \pi_k^m} \text{ if } C(w) = C(w+1), p \neq p', q = q', z = z' \\ (1-\tau^m) \times \tau^f \times (1-\tau^z) \times \dfrac{\pi_{q'}^m}{\sum_1^{q'-1} \pi_k^f + \sum_{q'+1}^K \pi_k^f} \text{ if } C(w) = C(w+1), p = p', q \neq q', z = z' \\ (1-\tau^m) \times \tau^f \times \tau^z \times \dfrac{\pi_{q'}^m}{\sum_1^{q'-1} \pi_k^f + \sum_{q'+1}^K \pi_k^f} \text{ if } C(w) = C(w+1), p = p', q \neq q', z \neq z' \\ 0 \text{ if } C(w) = C(w+1), p \neq p', q \neq q' \end{cases}$$

The symbol $$\pi_k^m$$

represents the label probability distribution of first parent label k over N different labels while $$\pi_k^f$$

represents the label probability distribution of second parent label k over N different labels. In some embodiments the label probability distributions may each correspond to a genome-wide distribution, but in other embodiments the distributions may correspond to a portion of the genome. In some cases, the label probabilities over all different labels sum to unity (i.e., $$\sum_{k \in K} \pi_k^m = \sum_{k \in K} \pi_k^f = 1).$$

The label probability distributions $$\pi_k^m \text{ and } \pi_k^f$$

indicates the preference of parent 1 and parent 2, respectively, for N different labels. For example, $$\pi_{p'}^m,$$

is the probability of first parent label of window w+1 taking the value k=p' over other possible values of labels K. C(w)=C(w+1) represents that the two windows correspond to the same chromosome. The label change probability $\tau^m$ represents the probability that first parent label will transition to a different label from window w to window w+1 (e.g., window w has a label of Geman while window w+1 has a label of Korean). In the embodiment that uses the equation above, the change of label depends on label probability $$\pi_k^m \text{ and } \pi_f^m.$$

The label change probability $\tau^f$ represents the probability that second parent label will transition to a different label from window w to window w+1. The label switch probability $\tau^z$ represents the probability that the order of first parent label and the second parent label is switched (e.g., the state will transition to the opposite z assignment between two windows.)

Hence, in the above equation, the first scenario represents that two windows are located in different chromosomes and the transition probability $P(U_w(p,q,z), U_{w+1}(p',q',z'))$ is equal to the first parent label probability of k=p' times the second parent label probability of k=q' divided by 2. The second scenario represents that the two windows are located in the same chromosome and there is no change in label or switch of label order. The transition probability in this scenario is equal to one minus the first parent label change probability $\tau^m$ (because the label either changes or does not change) times one minus the second parent label change probability $\tau^f$ times one minus label switch probability $\tau^z$. Other scenarios are modeled similarly in the equation above.

The values of label probabilities $$\left(\pi_k^m \text{ and } \pi_k^f\right),$$

label change probabilities ($\tau^m$ and $\tau^f$), and the label switch probability ($\tau^z$) are determined by the training of the inter-window HMM 400 based on a set of training data and, in some embodiments, additionally with the pair of haplotype datasets derived from an input sample genotype dataset X The values of label probabilities $$\left(\pi_k^m \text{ and } \pi_k^f\right)$$

of different k may be represented in a vector form (also referred to as label probability vector). In some embodiments, the values of the label probability vector and the label change probabilities are calculated with a Baum-Welch algorithm. In some embodiments, it may be assumed that a transition from a state $U_w(p,q,z)$ to another state $U_{w+1}(p',q',z')$ without any of the same labels p, q (i.e., both values of first parent label and second parent label change in a transition) are impossible. Hence, the transition probability for the last scenario in the equation above is zero in some embodiments. By omitting a transition for these low-probability transitions, the complexity of any inter-window simplified HMM (whether 400 or 410) may be reduced, thereby producing significant savings in time and computer processing requirements needed to determine labels.

If the window w+1 corresponds to a different chromosome than window w, then the state $U_w(p,q,z)$ may transition to an inter-chromosome state 420, which, in turn, transitions to a state $U_{w+1}(p',q',z)$ in the next window w+1. Thus, if the window w+1 corresponds to a different chromosome than window w, the state $U_w(p,q,z)$ may transition to a state $U_{w+1}(p',q',z)$ with a probability that is independent of the state $U_w(p,q,z)$ at window w (i.e., independent of (p,q)) because of the intervening inter-chromosome state 420.

If window w is the final window (i.e., w=W), then the state $U_w(p,q,z)$ in the window w transitions to an end state (not shown in FIG. 4B). Each state $U_w(p,q,z)$ in window w transitions to either a state $U_{w+1}(p',q',z)$ in window w+1, an inter-chromosome state 420, or an end state. FIG. 4B illustrates the possible outgoing transitions for each state $U_w(p,q,z)$ with arrows. For example, in window 2 (and in all windows w in which the window w+1 is on the same chromosome), the state 416 $U_2(1,2,1)$ may transition to the states $U_3(1,1,0)$, $U_3(1,1,1)$, $U_3(1,2,0)$, $U_3(1,2,1)$, etc. However, the state 416 $U_2(1,2,1)$ may not transition to state $U_3(3,3,0)$ because of both the first parent label and second parent label change in the transition. As such, no arrow connects the state 416 $U_2(1,2,1)$ to the state $U_3(3,3,0)$ in FIG. 4B.

In some embodiments, the transition probabilities are determined by reference panels from the reference panel sample store 240. Each reference panel is representative of a collection of genotypes from individuals with known ethnicities. Reference panel samples may include two different types, depending on whether a population is unadmixed or admixed. For a non-admixed population, an entire genetic dataset of an individual may constitute a reference panel sample. For example, for population A, which is assumed to be a non-admixed population, genetic datasets of individual 1, individual 2, and individual 3 may be three different reference panel samples that represent the genetic data of the population A. For population B, which is assumed to be an admixed population, a genetic dataset of an individual includes genetic segments that are inherited from different possible ethnic origins. For example, for a Hispanic population, the genetic dataset may include genetic segments of Native American origin, European origin, African origin, etc. For a particular ethnicity, various admixed individuals may have different genetic segments that are inherited from a particular ethnic origin. The online system may combine genetic segments of multiple admixed individuals to form a synthetic genetic dataset. For example, a reference panel sample for an admixed population may include a first genetic segment from a first admixed individual, a second genetic segment from a second admixed individual, etc. The first genetic segment and the second genetic segment are different segments. The full-ethnicity HMM may use an admixed reference panel. The admixed panel may include genetic segments inherited from multiple ethnic origins.

The reference panel sample store 240 may include different reference panel samples for various ethnic origins of admixed individuals originated from the same geographical region. A synthetic reference panel formed by combining genetic segments from various individuals may be associated with a geographical region and an ethnic origin. For example, a synthetic genetic dataset representing Native American origin for a Hispanic population from Mexico may be associated with both Mexico (a geographical region) and Native American (an ethnic origin). The reference panel sample store 240 may include another synthetic genetic dataset representing European origin for the same Hispanic population from Mexico. This reference panel may be associated with Mexico and European. Likewise, a synthetic genetic dataset associated with Brazil (a geographical region) and European (ethnic origin) may also be a different reference panel. Put differently, for an admixed population from a particular geographical region, multiple reference panels representing different ethnic origins may be stored.

The computing server 130 trains the HMM 410 to determine converged emission probability values and transition probability values. The computing server 130 apply a path determination dynamic programming algorithm such as a Viterbi algorithm to determine a probability most likely path for each HMM 410 using the input of a phased genotype dataset of the target individual. From the two haplotype sequences, the computing server 130 uses the HMM 410 to determine a path may start from the start state 416 and traverse one node per window until the entire HMM is traversed. After the path is determined, the ethnicity composition of the target individuals may be determined by counting the numbers of labels for each ethnicity along the path. The counting may be performed by including both the first labels that correspond to the first parent and the second labels that correspond to the second parent so that an overall label composition of the target individual is determined. The counting may also be performed separately for each haplotype as the HMM 410 includes separate and ordered labels for each haplotype.

The two-stage approach using a haploid full-ethnicity HMM 400 and a diploid simplified HMM 410 significantly reduces the complexity of the label determination pipeline and speeds up the computation process when compared to using a diploid and full-ethnicity HMM in a single-stage approach. For example, in a diploid and full-ethnicity HMM, the complexity is $O(N^2)$. In the haploid full-ethnicity HMM 400, the complexity is only $O(N)$. Since the complexity only scales linearly with the increase of N, the complexity of the haploid full-ethnicity HMM 400 is much lower than a diploid and full-ethnicity HMM. The complexity in a diploid simplified HMM 410 is also $O(N^2)$. However, since the complexity scales quadratically, the reduction of the number of ethnicity labels from N to K significantly reduces the complexity of the diploid simplified HMM 410. The simplification and speeding up using the two-stage approach are also supported by experimental results. Genotype datasets of 100 samples are run using the two-stage approach and the single-stage approach using a diploid and full-ethnicity HMM, the result shows that the two-stage approach significantly improves the computation time and also has a slightly improved accuracy. The accuracy estimate is the average correct assignment among 82 populations (regions, or possible ethnicity assignment labels) where the truth is measured as the actual proportion of DNA from each population that was included in the samples. The table below shows the experiment results.

| | 100 Samples | | |
| --- | --- | --- | --- |
| | User Time (s) | Real Time (20 threads) | Accuracy Estimate |
| Two-stage approach | 6833.2 | 12 m 18 s | 0.734651 |
| Fully diploid | 235837.24 | 4 h 22 m 33 s | 0.733339 |

A Method for Determining a Target Individual's Genotyping Labels

FIG. 5A and FIG. 5B are flowcharts depicting an example process 500 for determining a target individual's label compositions (e.g., ethnicity composition), in accordance with some embodiments. The process may be performed by one or more engines of the computing server 130 illustrated in FIG. 2A, such as the phasing engine 220, sample preprocessing engine 215, and ethnicity estimation engine 245. The process 500 may be embodied as a software algorithm that may be stored as computer instructions that are executable by one or more processors. The instructions, when executed by the processors, cause the processors to perform various steps in the process 500. In various embodiments, the process may include additional, fewer, or different steps. While various steps in process 500 may be discussed with the use of computing server 130, each step may be performed by a different computing device.

with reference to FIG. 5A, in some embodiments, a process 500 may include the receiving a phased genotype of a target individual (step 510). The phasing engine 220 may be used to phase a genotype for the target individual, such as by using a jig phasing algorithm. The target individual's genotype is phased to produce a first haplotype and a second haplotype, each haplotype corresponding to one parent of the target individual. The target individual's genotype may be pulled from the genetic data store 205 or supplied by the target individual to a company operating the computing server 130 for analysis. The phased genotype may comprise cross-chromosome haplotypes. The cross-chromosome haplotypes both include a sequence that has a span of genetic loci in a plurality of chromosomes. The computing server 130 may divide the phased genotype into a plurality of windows, each window comprising a set of single nucleotide polymorphisms (SNPs). In some embodiments, the pair of haplotype sequences are pre-determined and stored in genetic data store 205. The computing server 130 only retrieves the haplotype sequences instead of performing phasing as part of the label assignment process.

Continuing with reference to FIG. 5A, in some embodiments, process 500 includes initiating 520 a full-ethnicity hidden Markov model (HMM). As described in FIG. 4A, the full-ethnicity HMM includes a state for each ethnicity in the computing server 130. Each node in the full-ethnicity HMM represents a haplotype ethnicity from the set of ethnicity labels. An ethnicity label is produced for every ethnicity in the genealogy data store 205. The computing server 130 inputs 530 the first haplotype to the full-ethnicity HMM to determine a first subset of ethnicity labels that match the first haplotype. The computing server additionally inputs 540 the second haplotype to the full-ethnicity HMM to determine a second subset of ethnicity labels that match the second haplotype. The computing server 130 combines 550 the first and second subset of ethnicity labels as a candidate subset of ethnicity labels of the target individual. The candidate subset of ethnicity labels may represent a set of the target individual's ethnic origins.

Turning to FIG. 5B, the computing server 130 initiates 560 a simplified HMM specific to the target individual. The simplified HMM, as described in FIG. 4B, comprises nodes that are simplified from the set of ethnicity labels to the candidate subset of ethnicity labels. The computing server 130 uses the label determination system 270 to assign three labels to each state in the simplified HMM, as described in FIG. 4B. Each node in the simplified HMM represents permutations of different first parent ethnicity labels, second parent ethnicity labels, and switch labels. The switch labels represent a phasing error, the phasing error representative of switching the first and second parent ethnicity labels from one node group to a next node group. The computing server 130 inputs 570 the phased genotype of the target individual to the simplified HMM. Using the simplified HMM, the computing server 130 determines 580 an ethnicity composition of the target individual.

To determine the ethnicity composition of the target individual, the computing server 130 determines a path between the nodes in each window of the simplified HMM, as described in FIG. 4B. The computing server 130 generates paths based on a likelihood of the phased genotype of the target individual traversing nodes along the path. To calculate the likelihood, the computing server determines a label probability, a label switch probability, and a transition probability. The label probability represents a probability of each haplotype state having certain ethnicity labels. The label switch probability represents the likelihood of a phasing error between the labeling of each haplotype. The transition probability is associated with a particular edge in the path and represents a likelihood of the path being correct between nodes. In other words, the transition probability represents a likelihood of the first node connected by the path from one window transitioning to a second node connected by the path form another window. The computing server 130 connects each node between windows with edges. Each edge corresponds to a determined transition probability. The edges with the greatest probabilities may be used to form a path from the start of the HMM to an end, effectively producing a path mapping the target individual's ethnicity composition.

The computing server 130 counts a number of a particular label corresponding to a particular ethnicity label in the path. Based on the count of the particular label, the computing server 130 determines an ethnicity composition of the target individual with respect to the particular ethnicity label. This process may be repeated for each ethnicity label in the candidate ethnicity label subset. The computing server 130 determines the target individual's ethnicity composition by counting the number of ethnicity labels corresponding to each candidate ethnicity.

Example Graphical Results

Figure 6A:
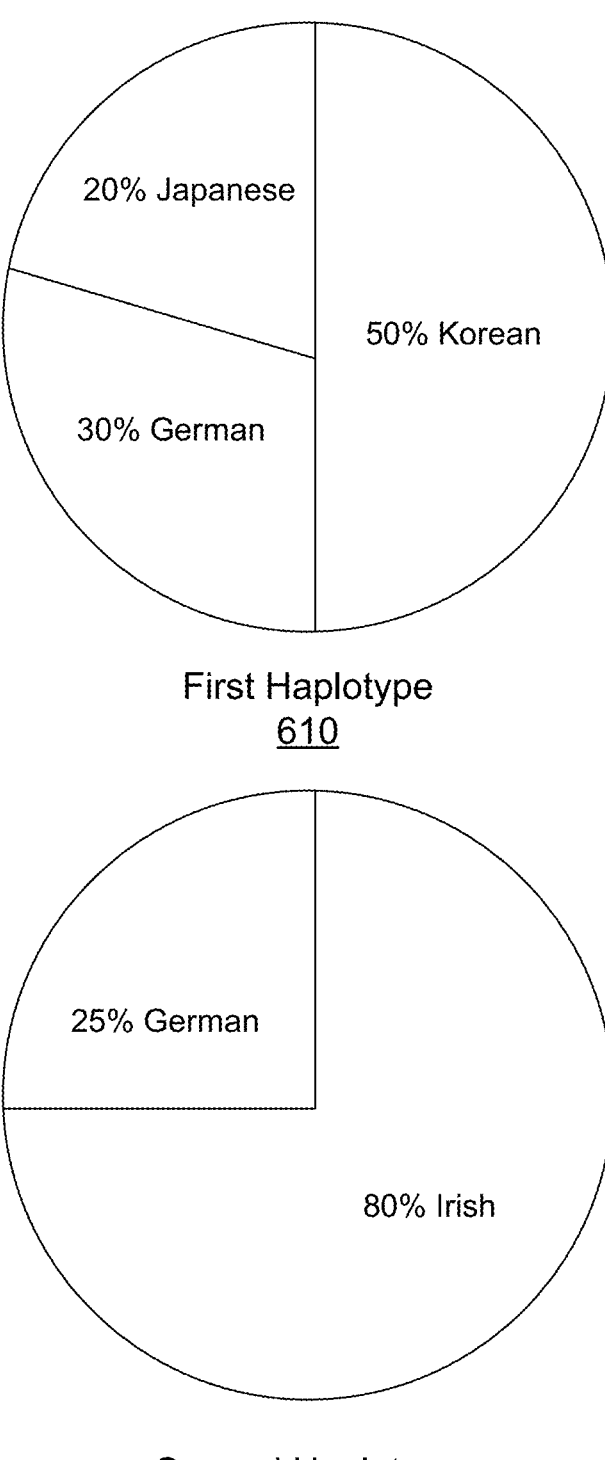
FIG. 6A is an example graphic describing the ethnicity composition for one or more individuals, in accordance with some embodiments.

Turning to FIG. 6A, the computing server 130 may additionally display the likelihood of the target individual having a particular ethnic origin. In some embodiments, the computing server 130 displays a first pie chart with a set of possible ethnic origins of the first haplotype and percentage compositions for each ethnic origin. The computing server 130 further displays a second pie chart comprising a set of possible ethnic origins of the second haplotype and percentage compositions of the set of possible ethnic origins. In the example embodiment illustrated by FIG. 6A, the target individual's first haplotype 610 is represented by a pie chart including Korean, Japanese, and German ethnicities. The pie chart illustrates percentage compositions for each ethnic origin, from 20-50%. The target individual's second haplotype 620 includes Irish and German ethnicities, with proportional shares of the "pie" for each ethnicity's percentage composition. In other embodiments, each haplotype may be labeled as a "First Parent" and "Second Parent." The pie charts may be generated for display on a user interface 115.

Figure 6B:
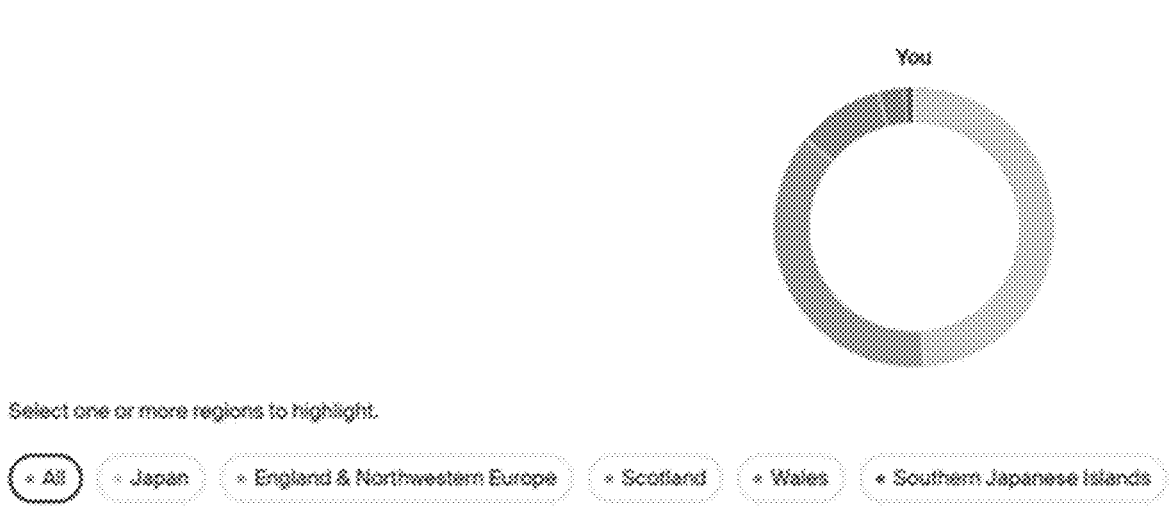
FIGS. 6B, 6C, and 6D are additional examples of graphical results that may be generated by the computing server, in accordance with some embodiments.
Figure 6C:
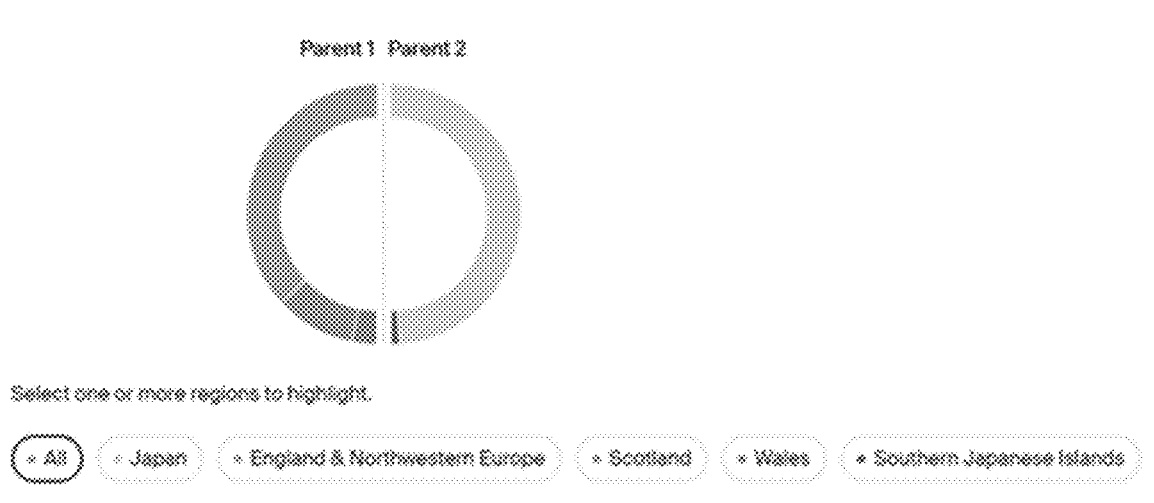
Figure 6D:

FIGS. 6B, 6C, and 6D are additional examples of graphical results that may be generated by the computing server 130, in accordance with some embodiments. As seen in FIGS. 6B and 6C, the user may have an overall ethnicity estimate (FIG. 6B). This may show ethnicities from which determined portions of the user's genome are descended. The user's overall ethnicity estimate may indicate 49% Japan, 1% Southern Japanese Islands, 37% England & Northwestern Europe, 10% Scotland, and 3% Wales, for example.

By contrast, embodiments may allow for discretizing the user's overall ethnicity estimate into estimate corresponding to each of the user's parents, with the 37% England & Northwestern Europe, 10% Scotland, and 3% Wales attributable to parent 1, and the 49% Japan and 1% Southern Japanese Islands being attributable to parent 2. This is shown further in FIG. 6D.

This discretization of a user's ethnicity to two parents without genetic samples from either parent may be facilitated by the provision and use of a long-distance phasing engine, such as a jig phasing algorithm. The phasing engine may be configured to phase diploid genetic dataset into a pair of haploid genetic datasets and may perform imputation of SNP values at certain sites whose alleles are missing. An individual's haplotype may refer to a collection of alleles (e.g., a sequence of alleles) that are inherited from a parent. The phasing engine may be configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's genetic datasets. The haplotype-cluster model may be generated iteratively along with the phasing process with a large number of unphased genotype datasets. The haplotype-cluster model may also be used to impute one or more missing data.

Further Detail on Label Assignment

Figure 7:
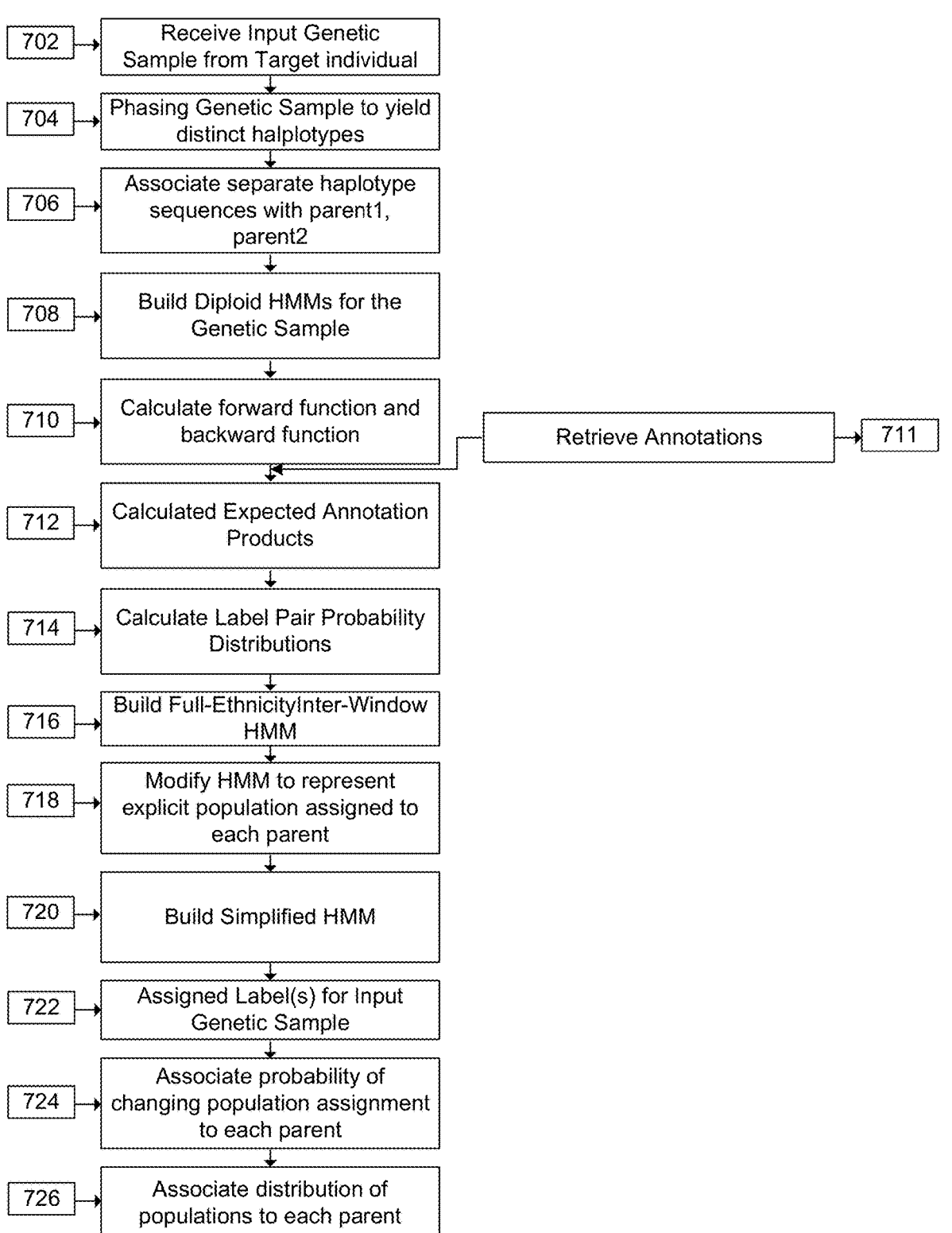
FIG. 7 is a flowchart depicting an example process for assigning labels for a genotype dataset of a target individual, in accordance with some embodiments.

FIG. 7 is a flowchart depicting an example process for assigning labels for a genotype dataset of a target individual, in accordance with some embodiments. The process may be performed by one or more engines of the computing server 130 illustrated in FIG. 2, such as the ethnicity estimation engine 245. The process 700 may be embodied as a software algorithm that may be stored as computer instructions that are executable by one or more processors. The instructions, when executed by the processors, cause the processors to perform various steps in the process 700. In various embodiments, the process may include additional, fewer, or different steps. For example, phasing may be predetermined and may not need to be performed in real time. While various steps in process 700 may be discussed with the use of computing server 130, each step may be performed by a different computing device.

In step 702, the computing server 130 may receive input genetic sample from a target individual. In step 704, the computing server 130 may phase genetic sample to yield distinct haplotypes. In step 706, the computing server 130 may associate the haplotype sequences with the first parent and the second parent. In step 708, the computing server 130 may build diploid HMMs for the genetic sample. An example of a diploid HMM for a particular window is illustrated in FIG. 3B. In step 710, The computing server 130 may calculate forward function and backward function. A forward function and backward function may be calculated so as to determine annotations for the windows. In parallel, in step 711, previously, or subsequently, annotations may be accessed from a set of annotations. The accessed annotations may correspond to a haploid state from a window and a label from a set of ethnicity labels.

In step 712, expected annotation products may be determined and, in turn, label pair probability distributions may be determined. This facilitates building an inter-window HMM, which may be used to assign ethnicity labels to the windows of the input genetic sample using, e.g., a Viterbi algorithm to navigate a plurality of stochastic paths for the inter-window HMM. In step 714, the computing server 130 may calculate label pair probability distributions.

In step 716, the computing server 130 may build a full-ethnicity and haploid inter-window HMM. The detail is described in FIG. 4A. With a certain probability, the state can change phase so that parent1 corresponds to the opposite sequence in the phased data compared to the previous window (either both parents change or neither does, thus the explicit enumeration of all the possible outcomes). In some embodiments, phased data may have two copies of the genome, e.g., haplotype 1 and haplotype 2. One parent/haplotype assignment may be designated as a preferred haplotype, meaning that the preferred haplotype is preferred for explaining DNA inherited from parent1l, whereas haplotype 2 is preferred for explaining DNA inherited from parent2. There may be two change-phase parameters instead of one: one to change from the preferred haplotype/parent assignment, and one to change back to the preferred assignment. Additionally, change-phase parameters may be predetermined. In other embodiments, the change-phase parameters are machine learned or otherwise determined from data. In some embodiments, the preferred haplotype/parent assignment is assumed to persist throughout the genome, such that each parent is separately analyzed with the inter-window full-ethnicity haploid HMM 400. The HMM 400 assigns one population to each window across the genome of a parent. Each parent may still have an overall population distribution and a parameter dictating the probability of changing population assignment from window to window. There only one state per population per window, representing the probability that the DNA inherited from one the one parent came from that population.

In step 718, the computing server 130 modifies a full-ethnicity diploid HMM to a simplified HMM 410 to represent explicit population assigned to each parent of the target individual. The step 720, the computing server 130 builds the simplified HMM 410. In step 722, the computing server 130 assigns labels for the input genetic sample. In step 724, the computing server 130 associates probability of changing population assignment to each parent. In step 726, the computing server 130 associates distribution of populations to each parent.

Annotations and Emission Probability

In FIG. 4A and FIG. 4B, each node (representing a state of a window) is associated with an emission probability that represents a likelihood of the window is observed as having a particular pair of phased haplotype datasets (or a particular haplotype in the case of a haploid HMM) given the window is in the hidden state represented by the node. The determination of the emission probability is based on genotype data of different reference panels and the input genotype dataset X through one or more intermediate steps that may include determinations of annotations, annotation products, and label pair probabilities. The details of the determination of the emission probability is discussed below.

The computing server 130 stores a set of reference panel samples of genotype datasets for each of the K labels. A reference panel for kth label is a collection of representative genetic datasets that belong to a community corresponding to kth label. For example, if the kth label represents a community of individual of an Asian reference panel, the reference panel samples in the kth-label reference panel are representative Asian genotype datasets. The set of reference panel samples corresponding to the kth label (for $k \in \{1, \ldots, K\}$) is referred to herein as $R_k$. Each reference panel sample $R \in R_k$ may be phased diploid genotype dataset of L SNPs, $R = (R_1, \ldots, R_L)$, where each $R_i$ (for $i \in \{1, \ldots, L\}$) is an SNP that is an ordered pair of binary alleles (i.e., (0,0), (0,1), (1,0) or (1,1)). At some sites of SNPs, there may be missing data. The labels may each correspond to a different origin population (e.g., an ethnic group), in which case each reference panel sample R may be a genotype data with a single origin from the kth origin population.

The possible labels may include both unadmixed labels and admixed labels. A collection of reference panel samples may be retrieved. The collection may include a plurality of unadmixed genetic datasets and a plurality of admixed synthetic genetic datasets. An admixed synthetic genetic dataset may be associated with both an ethnic origin and a geographical origin. For an admixed population, the same ethnic origin but with different geographical origins may be regarded as a different label. For labeling an admixed individuals, at least some of the nodes in an inter-window HMM may be labeled with a particular ethnic origin associated with an admixed population from a geographical origin. Other nodes in the inter-window HMM may be labeled with another ethnic origin associated with the admixed population from the geographical origin. For example, in FIG. 4B shown, label 1 may be associated with Mexico-Native American while label 2 may be associated with Mexico-European.

The label determination system receives haplotype data of a training set. The haplotype data may be a sequence of alleles corresponding to individuals. Each sequence of haplotype data may include alleles corresponding to the L SNPs of the genotypes stored in the genetic data store 205, or some subset thereof. The reference panel sample store 240 stores a set of reference samples for each of the K labels. The set of reference panel samples corresponding to the kth label (for k∈{1, . . . , K}) is referred to herein as $\boldsymbol{R}_k$. Each reference panel sample R∈ $\boldsymbol{R}_k$ in the store 240 may be an unphased diploid genotype of L SNPs, R=(R$_1$, . . . , R$_L$), where each R$_i$ (for i∈{1, . . . , L}) is an SNP that is either an unordered pair of binary alleles (i.e., (0,0), (0,1), or (1,1)) or missing data. The labels may each correspond to a different origin (e.g., an ethnic group), in which case each reference panel sample R may be a genotype from the kth origin population.

The label determination system 270 also receives a set of reference panel samples $\boldsymbol{R}_k$ for each label k (for 1<k<K). The set of reference panel samples $\boldsymbol{R}_k$ may be accessed from the reference panel sample store 240. Based on the set of reference panel samples $\boldsymbol{R}_k$ for label k and the haploid MMs for window w, the label determination system 270 calculates a set of annotations A$_w$(k,u) of every label k and every state u in the window w. The annotations A$_w$ may be stored in the annotation store 276. The label determination system 270 calculates annotation products L$_w$(d, p) based on the annotations. Based on the annotation products L$_w$(d, p), the label determination system 270 calculates label probability distributions. Based on the label pair probability distributions E$_{x,w}$(p,q), the label determination system 270 calculates the emission probability for each node. For an admixed individual, at least some of the nodes in the inter-window HMM may be assigned with probabilities that are calculated based on one or more synthetic genetic datasets.

Annotation Determination

The discussion in this subsection is related to calculation of annotation in association with the calculation of emission probabilities. The annotation A$_w$(k,u) is based on a calculation of the conditional probability of the haploid state u given the SNP sequence in the window w for the reference panel sample R that belongs to the set of reference panel samples $\boldsymbol{R}_k$ of the kth label. The calculation of the probability of the state u given reference panel sample R is based on the haploid MM for window w. For a given window w, label k, and state u, the annotation A$_w$(k,u) is equal to or positively correlated with the probability that a haplotype corresponding to label k includes the haploid state u in its path through window w. Equivalently, the annotation A$_w$(k, u) may be or may represent the expected proportion of haplotypes that include haploid state u in their corresponding paths for genotypes datasets selected from the set of reference panel samples $\boldsymbol{R}_k$.

In one embodiment, annotations are determined using a forward—backward algorithm. For a reference panel sample R∈ $\boldsymbol{R}_k$, the forward—backward algorithm may be used to calculate a forward function $f_{R,w}$ and a backward function $b_{R,w}$. The forward function $f_{R,w}$(u,v) may map the diploid state (u,v) at level d to the joint probability of the first d SNPs in window w of the reference panel sample R and the diploid state (u,v). That is, the output of the forward function $f_{R,w}$(u,v) is the probability, based on the haploid MM for the window w, that a genotype dataset has the first d SNPs of R and that R corresponds to the state (u,v) at level d. Similarly, the backward function $b_{R,w}$(u,v) may map the diploid state (u,v) at level d to the joint probability of the last (D-d) SNPs in window w of the reference panel sample R and the state (u,v). The forward—backwards product, $f_{R,w}$(u,v)×$b_{R,w}$(u, v), may be the joint probability of all the SNPs of the reference panel sample R in window w and the corresponding state (u,v). In some embodiments, the outputs of the forward function $f_{R,w}$ and the backward function $b_{R,w}$ are proportional, but not necessarily equal to the probabilities of their respective diploid states.

The annotation A$_w$(k,u) for the label k and state u may be given by:

$$A_w(k,\, u) = \frac{1}{|R_k|} \sum_{R \in R_k} \frac{1}{b_{R,w}(\mathbb{S}_w,\, \mathbb{S}_w)} \sum_{v \in \text{States In Level}_w(u)} f_{R,w}(u,\, v) \times b_{R,w}(u,\, v) \quad (1)$$

where | $R_k$| denotes the cardinality of the set $\boldsymbol{R}_k$ (i.e., the number of reference panel samples in $\boldsymbol{R}_k$) and where StatesInLevel$_w$(u) refers to the set of haploid states in the same level as u (i.e., if u is in level d, then StatesInLevel$_w$(u) is the set of all states at level d). Because ( $\mathbb{S}_w$, $\mathbb{S}_w$) is the start state of the diploid HMM 300 for window w, $b_{R,w}$( $\mathbb{S}_w$, $\mathbb{S}_w$) is equal to the likelihood of the reference panel sample R.

By the definition of the conditional probability, $f_{R,w}$(u, v)×$b_{R,w}$(u,v)/$b_{R,w}$( $\mathbb{S}_w$, $\mathbb{S}_w$) is the diploid state probability, i.e., the conditional probability that the path of a genotype dataset includes the state (u,v) in the diploid HMM 302 for window w given that the genotype dataset is a reference panel sample R. In some embodiments, the forward—backwards product $f_{R,w}$(u,v)×$b_{R,w}$(u,v) and $b_{R,w}$( $\mathbb{S}_w$, $\mathbb{S}_w$) are calculated to be proportional, but not necessarily equivalent, to the likelihood of their respective diploid states. In such an embodiment, the diploid state probability $f_{R,w}$(u,v)×$b_{R,w}$(u, v)/$b_{R,w}$( $\mathbb{S}_w$, $\mathbb{S}_w$) for reference panel sample R is still equivalent to the conditional probability that the path of the genotype includes the state (u,v) in the diploid HMM 302 given the genotype R.

The summation of the diploid state $f_{R,w}$(u,v)×$b_{R,w}$(u,v)/$b_{R,w}$( $\mathbb{S}_w$, $\mathbb{S}_w$) over all haploid states v in level d produces the marginal probability that the first haplotype (e.g., paternal, or maternal) is in haploid state u at level d given the reference panel sample R. The diploid state probabilities for a reference panel sample R may be summed over the set of diploid states that include the haploid state u (i.e., diploid states (u,v) and (v,u) for all haploid states v at the same level as the haploid state u) to produce a probability that the reference panel sample R corresponds to the haploid state u. Finally, the probabilities of u for each reference panel sample R may be combined to produce the annotation A$_w$(k,u). For example, A$_w$(k,u) may be the arithmetic average of the probabilities of the haploid state u for each reference panel sample R, therefore representing the expected proportion of reference panel samples in the set of reference panel samples $\boldsymbol{R}_k$ that include the state u in their respective paths. Stated differently, the annotation A$_w$(k,u) is the probability that the haploid state of a haplotype at a level d is haploid state u given that the haplotype corresponds to label k. In other alternatives, a different mathematical formulation other than arithmetic average may be used.

The annotations in the annotation store 276 may be calculated prior to determining labels for potentially admixed genotype datasets. In some embodiments, the annotations are updated based on labels determined for phased potentially admixed genotype datasets that are input to the system through the process described herein. In some embodiments, the annotations A$_w$(k,u) for a label k and window w may be iteratively improved by determining a probability that an admixed genotype dataset corresponds to a label k in window w and modifying the annotations A$_w$(k,u) accordingly.

Annotation Product Determination

The discussion in this subsection is related to calculation of annotation products in association with the calculation of emission probabilities.

Based on the annotations $A_w(k,u)$ and the input sample genotype dataset X, which is divided into two phased haplotypes, $x_{1,w}$ and $x_{2,w}$, each a sequence of alleles $\in \{0,1\}$ corresponding to the subsequence of SNPs in window w, the haploid MM module 284 may calculate a label probability $E_{x,w}(p)$ for each haplotype $x \in \{x_{1,w}, x_{2,w}\}$, and each label $p \in \{1, 2, \ldots, K\}$, where K is the number of possible labels. If window w is a subsequence of $D_w$ SNPs, the haploid MM module 284 determines a unique set of states $\{u_{x,w,0}, u_{x,w,1}, u_2, \ldots, u_{x,w,D_w}\}$ for a haplotype subsequence x in window w and the label probability for label p for a haplotype x is given by $$E_{x,w}(p) = \frac{1}{D_w}\sum_{d=0}^{D_w} \frac{A_w(p, u_{x,w,d})}{\sum_{k=1}^{K} A_w(k, u_{x,w,d})}$$

The annotation product corresponds to haplotype $x_1$ (one of the phased haplotypes) at window w. $E_{x1,w}(p)$ represents the likelihood that the window w corresponds to label p given that the haplotype is $x_1$. Another annotation product $E_{x2,w}(p)$ is calculated similarly for the other phased haplotype $x_2$.

Based on the label pair probability distributions for each window w, an inter-window HMM may be builted. The transition probabilities between states in the inter-window HMM may be based on the label pair probability distribution. Also, the inter-window HMM module may use the label pair probability distribution as the probability distribution of the states in window w given the SNPs in the window w. That is, the label pair probability distribution may be used in the inter-window HMM as the probability of the state $U_w(p,q,z)$ in window w given the observation (i.e., the sequence of SNPs of the phased datasets in the window w). Computing the inter-window HMM 400 for the phased datasets may include determining a label probability vector and label change probabilities for the inter-window HMM.

In some embodiments, the label pair probability distribution is used to calculate the emission probabilities for states in window w. That is, the label pair probability may be an estimate of the probability of the sequence of SNPs in window w given that the state for window w is $U_w(p,q,z)$. Here $x_1$ and $x_2$ are two phased haplotypes. The emission probability is determined based on the following equation:

$$E_{x,w}(p, q, z) = \begin{cases} E_{x1,w}(p) \times E_{x2,w}(q) & \text{if } z = 0 \\ E_{x1,w}(q) \times E_{x2,w}(p) & \text{if } z = 1 \end{cases}$$

Alternatively, based on the annotations $A_w(k,u)$ and the input sample genotype dataset X, a label pair probability $E_{x,w}(p,q,z)$ may be calculated as an estimate of the probability of the sequence of SNPs in window w given that the state for window w is $U_w(p,q,z)$ as $$E_{x,w}(p, q, z) = \sum_{d=0}^{D_w} \frac{L_{x,w}(p, q)}{\sum_{p',q'} L_{x,w}(p', q')}$$

where $L_{x,w}(p,q)$ is the expected annotation product given by $$L_{x,w}(p, q) = \sum_{u,v \in \alpha_d} \frac{f_{x,w}(u, v) \times b_{x,w}(u, v)}{b_{x,w}(\mathbb{S}_w, \mathbb{S}_w)} \times \frac{A_w(p, u) \times A_w(q, v) + A_w(q, u) \times A_w(p, v)}{2}$$

And $f_{x,w}(u,v) \times b_{x,w}(u,v)/b_{x,w}(\mathbb{S}_w, \mathbb{S}_w)$ is the diploid state probability, e.g., the conditional probability that the path of a genotype dataset x includes the state (u,v) in the diploid HMM 302 for window w. $\mathbb{S}_w$ is the distinguished starte state in the diploid HMM 302, and ad is the set of states in the diploid HMM 302 at level d. Note that when using the diploid HMM this way to determine the label pair probability, $E_{x,w}(p, q, z)$ does not depend on z.

Label Assignment

Using a set of training samples such as those obtained from different reference panels, the label determination system 270 calculates transition probabilities for different possible transitions for an inter-window HMM in the training of the inter-window HMM. Based on the reference panel samples and the input sample genotype dataset X, the label determination system 270 calculates the emission probabilities for different hidden states in the inter-window HMM. The label determination system 270 updates and builds (e.g., computes) an inter-window HMM using the pair of phased haplotype datasets derived from the input sample genotype dataset X. The computation may include generating data representing a directed acyclic graph that may include the structure of an inter-window HMM. The label determination system 270 uses Viterbi algorithm to estimate the label change probabilities and the label switch probability in the updated inter-window HMM. Based on the Viterbi path, the labels corresponding to the input sample genotype dataset X are determined. The determined Viterbi path may be used as one of the samples of a new set of training samples (which include the selected training samples from reference panels and the determined Viterbi path as an additional sample) to update and re-build the inter-window HMM. The training may be repeated for a predetermined number of iterations (e.g., 10 times) and/or repeated until the label changes probabilities and the label switch probability converge. The label determination system 270 uses the Viterbi algorithm one more time to determine the Viterbi path corresponding to the input sample genotype dataset X to assign the value of labels p, q and z in each window. A final path may be determined after repeating the Viterbi algorithm multiple times. The final path may traverse the directed acyclic path and may represent the a statistically likely path among other possible paths in traversing the directed acyclic graph.

In some embodiments, the label assignment may involve determining a proportion of the input sample genotype dataset X that corresponds to each label. For example, the label determination system 270 may determine that 25% of the input sample genotype dataset X corresponds to label 1, 0% corresponds to label 2, 50% corresponds to label 3, and 25% corresponds to label 4. The proportion of each label may be based on the states in the Viterbi path, based on the probability of being in each state (e.g., as calculated with the forward-backward algorithm), or otherwise based on the inter-window HMM. The determination of these proportions may also be based on a weight assigned to each window w. The weight of each window w may be based on the size of the window (e.g., in the number of bases). The weighting of each window w may be adjusted based on portions of the windows w that overlaps with other windows.

In some embodiments, the label assignment module 292 assigns a pair of ordered classification labels to each window w of the input sample genotype dataset X. In some embodiments, the label assignment module 292 determines the Viterbi path through the inter-window HMM 400. In alternate embodiments, the label assignment module 292 computes a number (e.g., 2700) of stochastic paths through the inter-window HMM and determines a range of each label's proportion based on the states taken by the stochastic process. For example, the label assignment module 292 may determine that 18-30% of the input sample genotype dataset X corresponds to a particular label. The range may be based on the maximum and minimum proportion of the genotype dataset X that corresponds to a label in the stochastic paths. Alternately, the range may be based on percentiles of the proportions of the input sample genotype dataset X that corresponds to a label in the stochastic paths. For example, the upper bound of a range for label k may be based on a 95th percentile of the proportions of the states that correspond to label k in the stochastic paths and the lower bound may be based on the 5th percentile. The most probable path or one of 95th percentile (or another suitable percentile) likely stochastic paths among other possible paths in traversing the directed acyclic graph may be referred to as a statistically likely path. Further details regarding determining different paths and range are discussed with reference to the Section below entitled "Range Determination."

In some embodiments, the label assignment module 292 assigns labels to specific portions of the input sample genotype dataset X. The label assignment module 292 may specifically assign labels to a portion of the input sample genotype dataset X that corresponds to one or more overlapping regions with a second genotype. For example, if the input sample genotype and the second genotype dataset are the genotypes of related individuals (e.g., first cousins), then the one or more overlapping regions are the regions of genetic information that correspond to one or more shared ancestors (e.g., a grandmother and a grandfather shared by the cousins). If, in an overlapping region, there is only one haplotype (in each genotype) that overlaps between the input sample genotype dataset X and the second genotype dataset, the label assignment module 292 may assign labels specifically to the overlapping haplotype.

For an admixed individual, the label determination and assignment may be similar but each label may include an ethnic origin and a geographical region. For example, a label for a particular window may be labeled with the ethnic origin Native America and with the geographical region of Mexico. A genetic segment that includes one or more consecutive windows may be assigned with the same label having the same ethnic-origin-geographical-region pair. The genetic segment may be added to one of the synthetic genetic datasets as part of a reference panel sample for an admixed population.

Phasing Operation Scaling Embodiments

Figure 8:
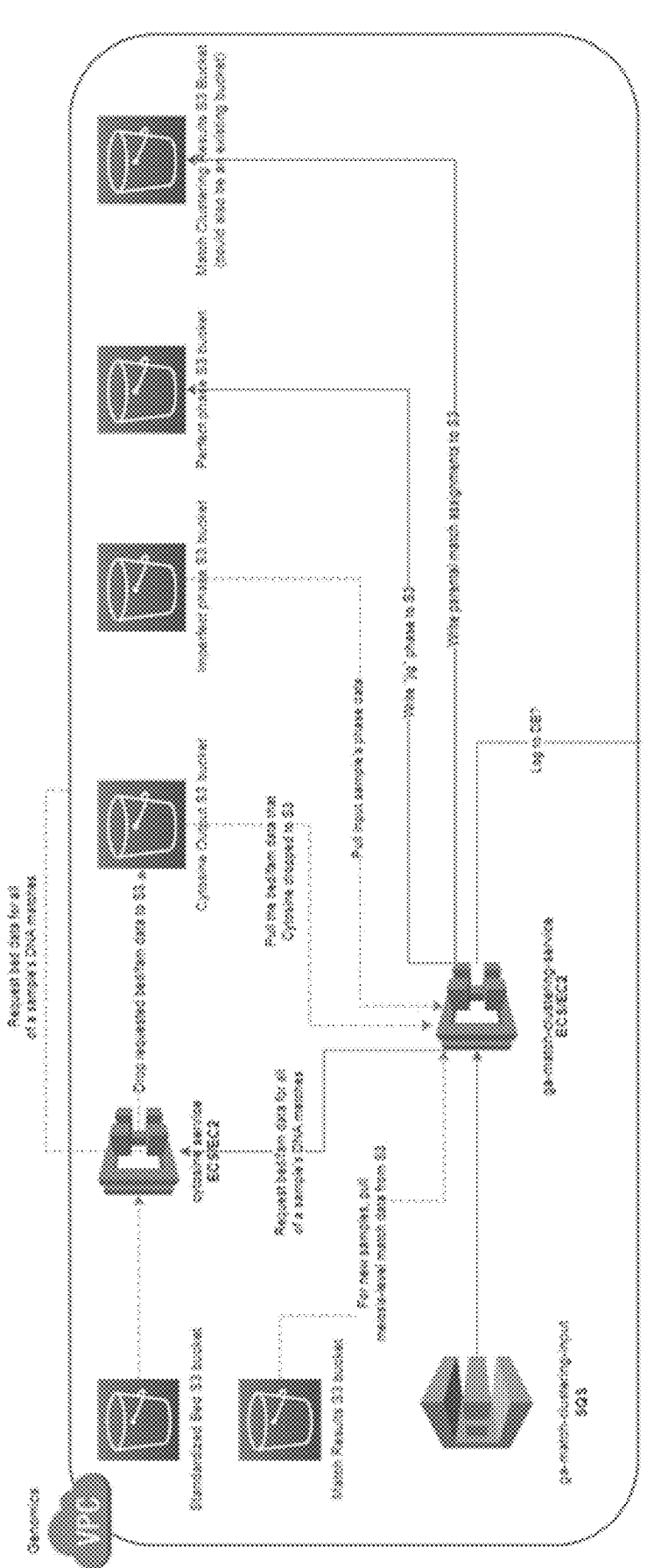
FIG. 8 is a block diagram illustrating example computer architecture of running a genotype analysis pipeline, in accordance with some embodiments.

FIG. 8 is a block diagram illustrating example computer architecture of running a genotype analysis pipeline, in accordance with some embodiments. A genotype analysis pipeline, as discussed above, may be performed to facilitate determination of parental ethnicities. A genotype analysis pipeline infrastructure may be provided and configured for phasing genomes. This advantageously allows for determining a user's parental ethnicities. As shown in FIG. 8, a customer genetic sample data may be retrieved from or through a service or server. In parallel, a customer's genetic matches and corresponding data may likewise be retrieved. These match data may be retrieved from the same or a separate service or server.

In some embodiments, parental ethnicities may be determined for many users in a relatively short period of time, e.g., 22 million customers within 10 days. Given that each customer may have 30,000 matches (corresponding to approximately 3 GB of data), a plurality of instances of a parental ethnicity determination system or component(s) thereof may be provided or utilized. Thousands (e.g., 4,000) such instances may be utilized in parallel.

It has been found that each instance, if configured to pull the entire genomic database onto its disc, would pull an untenably large volume of data. An autoscaling group service may be configured to retrieve only the segments of match data that are relevant to a particular customer's genetic sample to reduce the amount of data retrieved and stored. In response to a request for genetic data of matches for a customer sample, the relevant data is retrieved and utilized for phasing, with outputs including assigning matches to a particular cluster, phased haplotypes, and so on. The phased haplotypes may be used as described herein to determine parental ethnicity.

Because the phasing algorithm may take, In some embodiments, between two and four minutes per customer, an appropriate number of services may be provided to facilitate the processing of a predetermined number of customers within a predetermined timeframe, e.g., 22 million customers within 10 days will require, e.g., 4,000 instantiations of a phasing engine may be provided or utilized, each of which may be configured to cooperate with a group of 100 autoscaling group services. Each autoscaling group service may comprise, e.g., 100 "workers." Each worker is configured to host $1/100^{th}$ of the genomic data in the database.

It has been found that running these instantiations in parallel creates limits in a cloud computing environment such as AMAZON WEB SERVICES. The autoscaling group service downloads the raw genomic data and caches the same on disk for quick retrieval for phasing. 100 services, each with a plurality of workers, downloading the entirety of the genomic database (some 4.4 billion S3 downloads) results in some autoscaling group services getting stuck while downloading for unknown reasons. It has been surprisingly found that adding an async timeout on the download operation mitigates TimeOut errors and/or throttling errors.

It has similarly been found that cloud computing resources attempt to scale up partitioning systems behind the scenes to become responsive to high request rates. However, while this scales up, there are inevitably errors observed. It has been found that hitting this service as hard as possible and as fast as possible, early in the process, advantageously decreases errors as the partitioning systems scale up faster than otherwise.

Similarly, spot instances of cloud computing resources may be quickly depleted in an aggressive or fast process such as processing 22 million customers' data using 4,000 distinct instances of a phasing engine as described herein. A list of different instance types, with different priorities, may be determined and coordinated with the cloud computing resource so as to facilitate backfilling of instances.

Ethnicity Rounding Logic Embodiments

In some embodiments, the determining ethnicity labels may, at times, return estimates or labels that fall below a predetermined threshold for statistical significance. These labels may be removed or filtered to remove low-percentage regions, e.g., 0.4% or lower. This presents a challenge for users who are highly admixed with many ethnicities/regions represented. Removing all of the statistically insignificant data for these users often results in removing many regions or labels, which makes the task of rounding up the remaining regions to whole numbers that cumulatively equal 100% highly challenging. This is rounding procedure is important because users do not respond favorably to estimates that extend into several decimal places.

In some users, the remaining labels/ethnicities (after removal of statistically insignificant labels) are sorted in descending order of percentage (e.g., highest to lowest), and the delta between the sum of the remaining labels and 100 is determined. In some embodiments, each of the remaining labels is rounded up to the nearest whole number (e.g., from 72.66% to 73%). 1% is added to the topmost label and then to each descending label until the delta is zero, or in other words, the total of the labels is 100. This advantageously minimizes the percentage change to any one of the labels.

In some embodiments in which ethnicity data is discretized by parent1 and parent2, with percentages within each of parent1 and parent2, the task of rectifying the removal of low-percentage (i.e. statistically insignificant) regions is complicated further by the need to ensure that not only does the total ethnicity equal 100%, but also that both parents equal 50% and that each ethnicity region, represented as subtotals for one or both of the parents, matches. That is, if a user is 37% Scottish, the subtotal for Scottish in both parents must total 37%.

There is further a difficulty in cases where one parent contributes an ethnicity but the other parent does not; in these cases, it would be misleading and confusing to round up a zero region for the originally zero parent. For example, one parent may have Greek ethnicity but the other does not, imposing a requirement that the non-Greek parent's estimates are not padded or rounded up such that they appear to be partly Greek. Yet further, there is a challenge when one parent has an even number of statistically significant regions and the other has an odd number of statistically significant regions.

It has been found that by determining a parent1 delta and a parent2 delta, in addition to a total ethnicity delta, while tracking the list of parent1 and parent2 results that were originally zero, an effective one-pass correction may be made. In a first loop, parent1 and/or parent2 with a zero region are rounded up to the requisite 50% (after the removal of statistically insignificant labels) by sorting the parent-specific ethnicity labels in descending order, rounding each to the nearest whole number, and adding 1% starting with the top-most label until 50% is reached.

In some circumstances, a second loop is required. For some users, an imbalance is observed between the first and second parents wherein a negative delta is obtained. That is, in some circumstances the rounding up process may overfill a parent such that their delta is negative, in other words they now total more than 50%. A second loop is instantiated to determine which parent should be subtracted from (i.e. to reduce a negative delta or exceeding 50%) and which parent should be correspondingly added to. This may advantageously balance the two parents such that there is an even split therebetween. The subtraction and addition may be performed on the top-most labels for each of the parents.

Finally, a third loop is instantiated to finally adjust any remaining samples. For example, users without parents that have zero regions, the ethnicity labels may be rounded up to a nearest whole number, and then adding one percent starting with the top-most label and continuing therefrom, until a total of 50% for each parent and 100% total is attained.

This advantageously facilitates an effective single pass approach, comprising up to three loops or procedures, for adjusting the ethnicity labels for statistical significance. This reduces processing requirements and latency while maintaining acceptable results.

Data Compression and Transformation Embodiments

Determining parental ethnicities presents further challenges in that the data requirements for determining and presenting parental ethnicities, including windows for each parent (e.g., 2,002 windows), is daunting, particularly on a scale of millions of customers. Embodiments are configured to compress data and to render the data digestible for downstream clients.

Parental ethnicity data or metadata may be received as a plurality of windows within each of which an ethnicity label for each parent is provided. Each window may be separately mapped in a file to a particular chromosome and location thereon. A challenge is how to a) reduce the size of the data and b) combine and transform the ethnicity label data and the chromosome map data.

In some embodiments, the data is compressed to separate the two parents and to separate each chromosome. Windows may be separated into groups of windows, e.g., windows 1-100, 101-200, and so on. This facilitates compression of the data in the group of windows. The windows may further be linked with location data. This advantageously reduces the number of windows from 2,002 to, e.g., 22 chromosomes for each parent divided out by clusters of windows representing ethnicities.

Unprocessed, raw data for an average user may be approximately 41-45 kb, but in compressed form according to the disclosed embodiments the data file is reduced to approximately 6-8 kb. For individuals with few regions, the unprocessed data may be approximately 48 kb, but compressed it is less than 4 kb, an order of magnitude reduction. Not only has the data been compressed by an order of magnitude, they also include additional, location-specific data, which in an unprocessed form may be approximately 50 kb.

The provision of data compression and transformation modalities as described herein advantageously reduce storage and processing requirements and time. The additional storage that would be required for the unprocessed data is avoided, processing time and costs are reduced, and network time and costs are reduced.

Computing Machine Architecture

Figure 9:
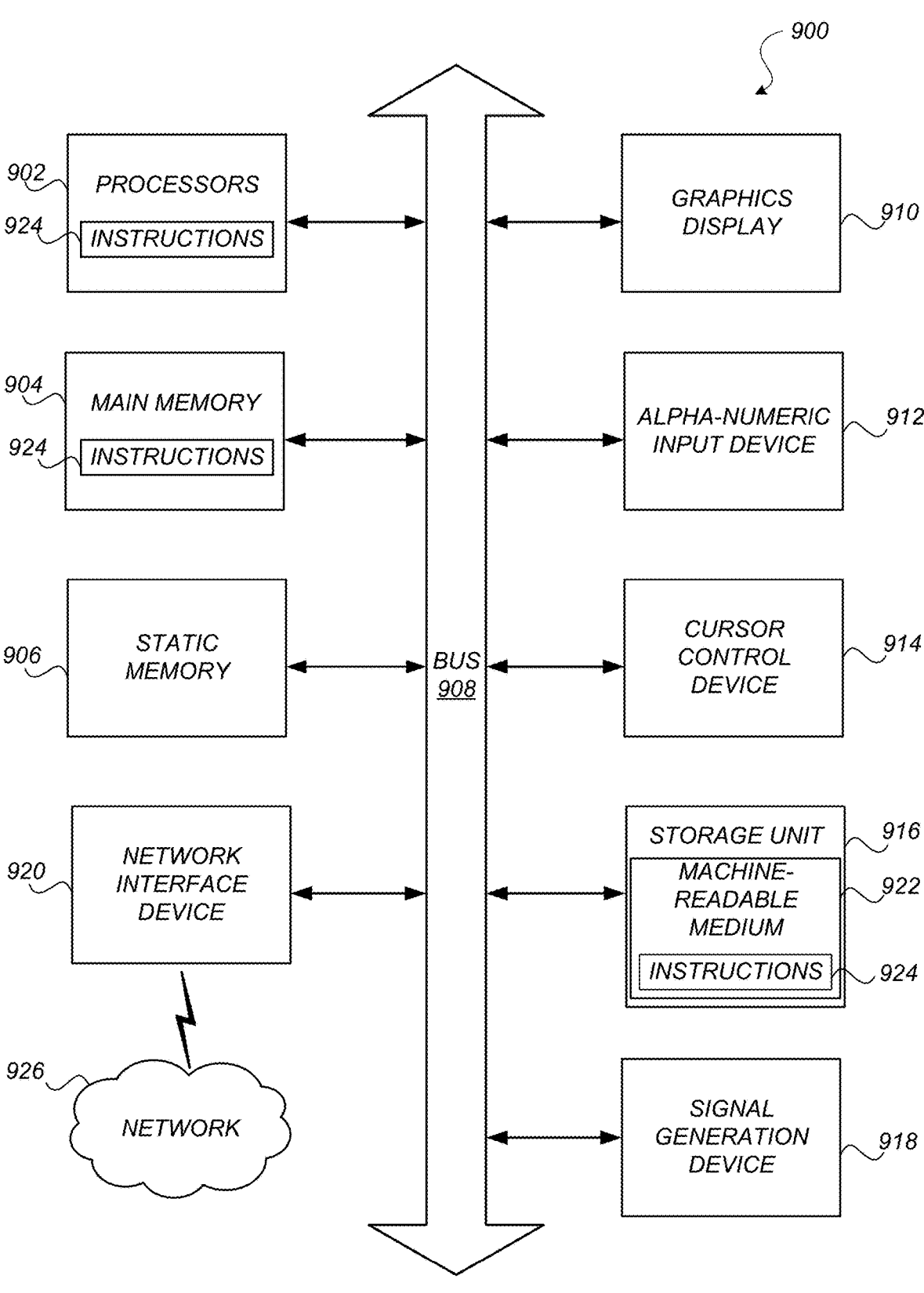
FIG. 9 is a block diagram of an example computing device, in accordance with some embodiments.

FIG. 9 is a block diagram illustrating components of an example computing machine that is capable of reading instructions from a computer-readable medium and execute them in a processor (or controller). A computer described herein may include a single computing machine shown in FIG. 9, a virtual machine, a distributed computing system that includes multiple nodes of computing machines shown in FIG. 9, or any other suitable arrangement of computing devices.

By way of example, FIG. 9 shows a diagrammatic representation of a computing machine in the example form of a computer system 900 within which instructions 924 (e.g., software, source code, program code, expanded code, object code, assembly code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 9 may correspond to any software, hardware, or combined components shown in FIGS. 1 and 2, including but not limited to, the client device 110, the computing server 130, the label determination system 270 and various engines, interfaces, terminals, and machines shown in FIG. 2. While FIG. 9 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 924 that specify actions to be taken by that machine. Further, while only a single machine is illustrated, the term "machine" and "computer" may also be taken to include any collection of machines that individually or jointly execute instructions 924 to perform any one or more of the methodologies discussed herein.

The example computer system 900 includes one or more processors 902 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 900 may also include a memory 904 that store computer code including instructions 924 that may cause the processors 902 to perform certain actions when the instructions are executed, directly or indirectly by the processors 902. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 902 and reduces the space required for the memory 904. For example, the database processing techniques and machine learning methods described herein reduce the complexity of the computation of the processors 902 by applying one or more novel techniques that simplify the steps in training, reaching convergence, and generating results of the processors 902. The algorithms described herein also reduces the size of the models (e.g., HMMs) and datasets to reduce the storage space requirement for memory 904.

The performance of certain operations may be distributed among more than one processor, not only residing within a single machine, but deployed across a number of machines. In some example embodiments, the one or more processors or processor-implemented modules may be located in a single geographic location (e.g., within a home environment, an office environment, or a server farm). In other example embodiments, one or more processors or processor-implemented modules may be distributed across a number of geographic locations. Even though in the specification or the claims may refer some processes to be performed by a processor, this should be construed to include a joint operation of multiple distributed processors.

The computer system 900 may include a main memory 904, and a static memory 906, which are configured to communicate with each other via a bus 908. The computer system 900 may further include a graphics display unit 910 (e.g., a plasma display panel (PDP), a liquid crystal display (LCD), a projector, or a cathode ray tube (CRT)). The graphics display unit 910, controlled by the processors 902, displays a graphical user interface (GUI) to display one or more results and data generated by the processes described herein. The computer system 900 may also include alpha-numeric input device 912 (e.g., a keyboard), a cursor control device 914 (e.g., a mouse, a trackball, a joystick, a motion sensor, or other pointing instruments), a storage unit 916 (a hard drive, a solid-state drive, a hybrid drive, a memory disk, etc.), a signal generation device 918 (e.g., a speaker), and a network interface device 920, which also are configured to communicate via the bus 908.

The storage unit 916 includes a computer-readable medium 922 on which is stored instructions 924 embodying any one or more of the methodologies or functions described herein. The instructions 924 may also reside, completely or at least partially, within the main memory 904 or within the processor 902 (e.g., within a processor's cache memory) during execution thereof by the computer system 900, the main memory 904 and the processor 902 also constituting computer-readable media. The instructions 924 may be transmitted or received over a network 926 via the network interface device 920.

While computer-readable medium 922 is shown in an example embodiment to be a single medium, the term "computer-readable medium" should be taken to include a single medium or multiple media (e.g., a centralized or distributed database, or associated caches and servers) able to store instructions (e.g., instructions 924). The computer-readable medium may include any medium that is capable of storing instructions (e.g., instructions 924) for execution by the processors (e.g., processors 902) and that cause the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

ADDITIONAL CONSIDERATIONS

In some aspects, the techniques described herein relate to a computer-implemented method including: receiving a phased genotype of a target individual, the phased genotype including a first haplotype and a second haplotype; initiating a full-ethnicity hidden Markov model (HMM), the full-ethnicity HMM including nodes that have a set of ethnicity labels; inputting the first haplotype to the full-ethnicity HMM to determine a first subset of ethnicity labels that match the first haplotype; inputting the second haplotype to the full-ethnicity HMM to determine a second subset of ethnicity labels that match the second haplotype; combining the first and second subsets of ethnicity labels as a candidate subset of ethnicity labels of the target individual; initiating a simplified HMM specific to the target individual, the simplified HMM including nodes that are simplified from the set of ethnicity labels to the candidate subset of ethnicity labels of the target individual; inputting the phased genotype of the target individual to the simplified HMM; and determining an ethnicity composition of the target individual using the simplified HMM.

In some aspects, the techniques described herein relate to a computer-implemented method, wherein the nodes in the simplified HMM represent permutations of different first parent ethnicity labels, second parent ethnicity labels, and switch labels.

In some aspects, the techniques described herein relate to a computer-implemented method, wherein the switch labels represent a phasing error, the phasing error representative of switching the first and second parent ethnicity labels from one node group to a next node group.

In some aspects, the techniques described herein relate to a computer-implemented method, wherein the nodes in the full-ethnicity HMM each represent a haplotype ethnicity from the set of ethnicity labels.

In some aspects, the techniques described herein relate to a computer-implemented method, wherein the phased genotype includes cross-chromosome haplotypes, and wherein the first haplotype and the second haplotype both include a sequence that has span of genetic loci in a plurality of chromosomes.

In some aspects, the techniques described herein relate to a computer-implemented method, wherein receiving the phased genotype further includes: dividing the phased genotype into a plurality of windows, each window including a set of single nucleotide polymorphisms (SNPs).

In some aspects, the techniques described herein relate to a computer-implemented method, wherein determining the ethnicity composition further includes: determining a path between the nodes in each window of the simplified HMM based on a likelihood of the phased genotype of the target individual traversing nodes along the path; counting a number of a particular label corresponding to a particular ethnicity label in the path; and determining an ethnicity composition of the target individual with respect to the particular ethnicity label based on the number of the particular label counted in the path.

In some aspects, the techniques described herein relate to a computer-implemented method, wherein determining the likelihood further includes: determining a label probability, a label switch probability, and a transition probability, the transition probability associated with a particular edge in the path and representing a likelihood of the first node connected by the path from one window transitioning to the second node connected by the path from another window; connecting the nodes with edges, each edge corresponding to a determined transition probability.

In some aspects, the techniques described herein relate to a computer-implemented method, wherein determining the ethnicity composition further includes: displaying the likelihood of the target individual having the particular ethnic origin.

In some aspects, the techniques described herein relate to a computer-implemented method, wherein displaying the likelihood of the target individual having the particular ethnic origin further includes: determining a minimum label threshold value; filtering ethnicity labels below the determined minimum label threshold value; sorting the filtered ethnicity labels in descending order; determining a delta between the sum of the filtered ethnicity labels and a total number of ethnicity label; and adding a predetermined value to one of the filtered ethnicity labels at a time until the delta is zero.

In some aspects, the techniques described herein relate to a computer-implemented method, wherein the phased genotype is generated with a global phasing algorithm.

In some aspects, the techniques described herein relate to a computer-implemented method, wherein the full-ethnicity HMM transition probabilities are determined by reference panels, the reference panel representative of a collection of genotypes from individuals with known ethnicities.

In some aspects, the techniques described herein relate to a computer-implemented method, wherein one of the reference panels is an admixed panel, the admixed panels including genetic segments inherited from multiple ethnic origins.

In some aspects, the techniques described herein relate to a non-transitory computer readable medium storing computer code including instructions that, when executed by one or more processors, causing the one or more processors to perform steps including: receiving a phased genotype of a target individual, the phased genotype including a first haplotype and a second haplotype; initiating a full-ethnicity hidden Markov model (HMM), the full-ethnicity HMM including nodes that have a set of ethnicity labels; inputting the first haplotype to the full-ethnicity HMM to determine a first subset of ethnicity labels that match the first haplotype; inputting the second haplotype to the full-ethnicity HMM to determine a second subset of ethnicity labels that match the second haplotype; combining the first and second subsets of ethnicity labels as a candidate subset of ethnicity labels of the target individual; initiating a simplified HMM specific to the target individual, the simplified HMM including nodes that are simplified from the set of ethnicity labels to the candidate subset of ethnicity labels of the target individual; inputting the phased genotype of the target individual to the simplified HMM; and determining an ethnicity composition of the target individual using the simplified HMM.

In some aspects, the techniques described herein relate to a non-transitory computer readable medium, wherein the nodes in the simplified HMM represent permutations of different first parent ethnicity labels, second parent ethnicity labels, and switch labels.

In some aspects, the techniques described herein relate to a non-transitory computer readable medium, wherein the switch labels represent a phasing error, the phasing error representative of switching the first and second parent ethnicity labels from one node group to a next node group.

In some aspects, the techniques described herein relate to a non-transitory computer readable medium, wherein the phased genotype includes cross-chromosome haplotypes, and wherein the first haplotype and the second haplotype both include a sequence that has span of genetic loci in a plurality of chromosomes.

In some aspects, the techniques described herein relate to a non-transitory computer readable medium, wherein receiving the phased genotype further includes: dividing the phased genotype into a plurality of windows, each window including a set of single nucleotide polymorphisms (SNPs).

In some aspects, the techniques described herein relate to a computer-implemented method, wherein determining the ethnicity composition further includes: determining a path between the nodes in each window of the simplified HMM based on a likelihood of the phased genotype of the target individual traversing nodes along the path; counting a number of a particular label corresponding to a particular ethnicity label in the path; and determining an ethnicity composition of the target individual with respect to the particular ethnicity label based on the number of the particular label counted in the path.

In some aspects, the techniques described herein relate to a system including: one or more processors; and a memory configured to store computer code including instructions, the instructions, when executed by one or more processors, cause the one or more processors to perform steps including: receiving a phased genotype of a target individual, the phased genotype including a first haplotype and a second haplotype; initiating a full-ethnicity hidden Markov model (HMM), the full-ethnicity HMM including nodes that have a set of ethnicity labels; inputting the first haplotype to the full-ethnicity HMM to determine a first subset of ethnicity labels that match the first haplotype; inputting the second haplotype to the full-ethnicity HMM to determine a second subset of ethnicity labels that match the second haplotype; combining the first and second subsets of ethnicity labels as a candidate subset of ethnicity labels of the target individual; initiating a simplified HMM specific to the target individual, the simplified HMM including nodes that are simplified from the set of ethnicity labels to the candidate subset of ethnicity labels of the target individual; inputting the phased genotype of the target individual to the simplified HMM; and determining an ethnicity composition of the target individual using the simplified HMM.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g., method, can be claimed in another claim category, e.g., computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In some embodiments, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed in the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. Pat. No. 10,679,729, entitled "Haplotype Phasing Models," granted on Jun. 9, 2700, (2) U.S. Pat. No. 10,223,498, entitled "Discovering Population Structure from Patterns of Identity-By-Descent," granted on Mar. 5, 2019, (3) U.S. Pat. No. 10,720,229, entitled "Reducing Error in Predicted Genetic Relationships," granted on Jul. 21, 2700, (4) U.S. Pat. No. 10,558,930, entitled "Local Genetic Ethnicity Determination System," granted on Feb. 11, 2700, (5) U.S. Pat. No. 10,114,922, entitled "Identifying Ancestral Relationships Using a Continuous Stream of Input," granted on Oct. 30, 2018, (6) U.S. Pat. No. 11,429,615, entitled "Linking Individual Datasets to a Database," granted on Aug. 30, 2022, (7) U.S. Pat. No. 10,692,587, entitled "Global Ancestry Determination System," granted on Jun. 23, 2700, and (8) U.S. Patent Application Publication No. US 2701/0034647, entitled "Clustering of Matched Saaegments to Determine Linkage of Dataset in a Database," published on Feb. 4, 2701.

What is claimed is:

1. A computer-implemented method comprising:

receiving a phased genotype of a target individual, the phased genotype comprising a first haplotype and a second haplotype;

initiating a full-ethnicity hidden Markov model (HMM), the full-ethnicity HMM comprising nodes that have a set of ethnicity labels;

inputting the first haplotype to the full-ethnicity HMM to determine a first subset of ethnicity labels that match the first haplotype;

inputting the second haplotype to the full-ethnicity HMM to determine a second subset of ethnicity labels that match the second haplotype;

combining the first and second subsets of ethnicity labels as a candidate subset of ethnicity labels of the target individual;

initiating a simplified HMM specific to the target individual, the simplified HMM comprising nodes that are simplified from the set of ethnicity labels to the candidate subset of ethnicity labels of the target individual;

inputting the phased genotype of the target individual to the simplified HMM; and determining an ethnicity composition of the target individual using the simplified HMM.

2. The computer-implemented method of claim 1, wherein the nodes in the simplified HMM represent permutations of different first parent ethnicity labels, second parent ethnicity labels, and switch labels.

3. The computer-implemented method of claim 2, wherein the switch labels represent a phasing error, the phasing error representative of switching the first and second parent ethnicity labels from one node group to a next node group.

4. The computer-implemented method of claim 1, wherein the nodes in the full-ethnicity HMM each represent a haplotype ethnicity from the set of ethnicity labels.

5. The computer-implemented method of claim 1, wherein the phased genotype comprises cross-chromosome haplotypes, and wherein the first haplotype and the second haplotype both include a sequence that has span of genetic loci in a plurality of chromosomes.

6. The computer-implemented method of claim 1, wherein receiving the phased genotype further comprises:

dividing the phased genotype into a plurality of windows, each window comprising a set of single nucleotide polymorphisms (SNPs).

7. The computer-implemented method of claim 6, wherein determining the ethnicity composition further comprises:

determining a path between the nodes in each window of the simplified HMM based on a likelihood of the phased genotype of the target individual traversing nodes along the path;

counting a number of a particular label corresponding to a particular ethnicity label in the path; and determining an ethnicity composition of the target individual with respect to the particular ethnicity label based on the number of the particular label counted in the path.

8. The computer-implemented method of claim 7, wherein determining the likelihood further comprises:

determining a label probability, a label switch probability, and a transition probability, the transition probability associated with a particular edge in the path and representing a likelihood of the first node connected by the path from one window transitioning to the second node connected by the path from another window;

connecting the nodes with edges, each edge corresponding to a determined transition probability.

9. The computer-implemented method of claim 6, wherein determining the ethnicity composition further comprises:

displaying the likelihood of the target individual having the particular ethnic origin.

10. The computer-implemented method of claim 7, wherein displaying the likelihood of the target individual having the particular ethnic origin further comprises:

determining a minimum label threshold value;

filtering ethnicity labels below the determined minimum label threshold value;

sorting the filtered ethnicity labels in descending order;

determining a delta between the sum of the filtered ethnicity labels and a total number of ethnicity label; and adding a predetermined value to one of the filtered ethnicity labels at a time until the delta is zero.

11. The computer-implemented method of claim 1, wherein the phased genotype is generated with a global phasing algorithm.

12. The computer-implemented method of claim 1, wherein the full-ethnicity HMM transition probabilities are determined by reference panels, the reference panel representative of a collection of genotypes from individuals with known ethnicities.

13. The computer-implemented method of claim 12, wherein one of the reference panels is an admixed panel, the admixed panels including genetic segments inherited from multiple ethnic origins.

14. A non-transitory computer readable medium storing computer code comprising instructions that, when executed by one or more processors, causing the one or more processors to perform steps comprising:

receiving a phased genotype of a target individual, the phased genotype comprising a first haplotype and a second haplotype;

initiating a full-ethnicity hidden Markov model (HMM), the full-ethnicity HMM comprising nodes that have a set of ethnicity labels;

inputting the first haplotype to the full-ethnicity HMM to determine a first subset of ethnicity labels that match the first haplotype;

inputting the second haplotype to the full-ethnicity HMM to determine a second subset of ethnicity labels that match the second haplotype;

combining the first and second subsets of ethnicity labels as a candidate subset of ethnicity labels of the target individual;

initiating a simplified HMM specific to the target individual, the simplified HMM comprising nodes that are simplified from the set of ethnicity labels to the candidate subset of ethnicity labels of the target individual;

inputting the phased genotype of the target individual to the simplified HMM; and determining an ethnicity composition of the target individual using the simplified HMM.

15. The non-transitory computer readable medium of claim 14, wherein the nodes in the simplified HMM represent permutations of different first parent ethnicity labels, second parent ethnicity labels, and switch labels.

16. The non-transitory computer readable medium of claim 15, wherein the switch labels represent a phasing error, the phasing error representative of switching the first and second parent ethnicity labels from one node group to a next node group.

17. The non-transitory computer readable medium of claim 14, wherein the phased genotype comprises cross-chromosome haplotypes, and wherein the first haplotype and the second haplotype both include a sequence that has span of genetic loci in a plurality of chromosomes.

18. The non-transitory computer readable medium of claim 14, wherein receiving the phased genotype further comprises:

dividing the phased genotype into a plurality of windows, each window comprising a set of single nucleotide polymorphisms (SNPs).

19. The non-transitory computer readable medium of claim 18, wherein determining the ethnicity composition further comprises:

determining a path between the nodes in each window of the simplified HMM based on a likelihood of the phased genotype of the target individual traversing nodes along the path;

counting a number of a particular label corresponding to a particular ethnicity label in the path; and determining an ethnicity composition of the target individual with respect to the particular ethnicity label based on the number of the particular label counted in the path.

20. A system comprising:

one or more processors; and a memory configured to store computer code comprising instructions, the instructions, when executed by one or more processors, cause the one or more processors to perform steps comprising:

receiving a phased genotype of a target individual, the phased genotype comprising a first haplotype and a second haplotype;

initiating a full-ethnicity hidden Markov model (HMM), the full-ethnicity HMM comprising nodes that have a set of ethnicity labels;

inputting the first haplotype to the full-ethnicity HMM to determine a first subset of ethnicity labels that match the first haplotype;

inputting the second haplotype to the full-ethnicity HMM to determine a second subset of ethnicity labels that match the second haplotype;

combining the first and second subsets of ethnicity labels as a candidate subset of ethnicity labels of the target individual;

initiating a simplified HMM specific to the target individual, the simplified HMM comprising nodes that are simplified from the set of ethnicity labels to the candidate subset of ethnicity labels of the target individual;

inputting the phased genotype of the target individual to the simplified HMM; and determining an ethnicity composition of the target individual using the simplified HMM.

* * * * *